United States Patent [19]

Demerson et al.

[11] 4,056,538

[45] Nov. 1, 1977

[54] PROCESS FOR PREPARING PYRANO- AND THIOPYRANOINDOLE DERIVATIVES

[75] Inventors: Christopher A. Demerson; Leslie G. Humber, both of Montreal; André A. Asselin, Lemoyne; Ivo Jirkovsky; Thomas A. Dobson, both of Montreal, all of Canada

[73] Assignee: Ayerst, McKenna & Harrison Limited, Montreal, Canada

[21] Appl. No.: 733,834

[22] Filed: Oct. 18, 1976

Related U.S. Application Data

[62] Division of Ser. No. 507,085, Sept. 18, 1974, abandoned, which is a division of Ser. No. 217,627, Jan. 13, 1972, Pat. No. 3,852,285.

[51] Int. Cl.$^2$ ............................................. C07D 491/04
[52] U.S. Cl. ...................... 260/326.5 B; 260/268 TR; 260/293.57; 260/293.58; 260/326.34; 260/326.5 SA; 260/326.82; 260/326.9; 544/142; 544/121; 544/129; 544/130; 544/80
[58] Field of Search .................... 260/247.16, 247.2 B, 260/247.5 FD, 247.5 D, 246 B, 268 TR, 293.57, 293.58, 326.34, 326.55 A, 326.5 B, 326.82, 326.9

[56] References Cited

U.S. PATENT DOCUMENTS 3,852,285  12/1954  Demerson et al. ........... 260/247.1 L

*Primary Examiner*—Henry R. Jiles
*Assistant Examiner*—R. W. Ramsuer
*Attorney, Agent, or Firm*—Adley F. Mandel

[57] ABSTRACT

Pyranoindole and thiopyranoindole derivatives characterized by having an amino(lower)alkyl radical attached to either or both the 1 and 9 position of a pyrano[3,4-b]indole or thiopyrano[3,4-b]indole nucleus are disclosed. The amino position of the amino(lower)alkyl radical may be further substituted with one or two lower alkyl groups or incorporated into a heterocyclic amine radical. The derivatives having the amino(lower)alkyl radical only at position 1 are further substituted at position 1 and may be optionally substituted at positions 3, 4, 5, 6, 7, 8, and 9. The derivatives having the amino (lower)alkyl radical only at position 9 posses two substituents at position 1 and may be optionally substituted at position 3, 4, 5, 6, 7, and 8. The derivatives having an amino(lower)alkyl radical at both positions 1 and 9 are further substituted at position 1 and may be optionally substituted at positions 3, 4, 5, 6, 7, and 8. The pyranoand thiopyranoindole derivatives of this invention are useful antidepressant and antiulcer agents. Methods for the preparation and use of these derivatives are also disclosed.

10 Claims, No Drawings

PROCESS FOR PREPARING PYRANO- AND THIOPYRANOINDOLE DERIVATIVES

This is a division of application Ser. No. 507,085, filed Sept. 18, 1974, now abandoned, which in turn is a division of Ser. No. 217,627 filed Jan. 13, 1972 and now U.S. Pat. No. 3,852,285, issued Dec. 3, 1974.

BACKGROUND OF THE INVENTION

1. Field of Invention

This invention relates to novel pyranoindole and thiopyranoindole derivatives, to processes for their preparation and to intermediates used in these processes.

More specifically, the present invention relates to novel pyranoindole and thiopyranoindole derivatives possessing valuable pharmacologic properties. For example, these derivatives exhibit useful antidepressant properties at dosages which do not elicit undesirable side effects. Furthermore the present derivatives exhibit properties useful for the treatment and prevention of ulcers. The combination of these pharmacologic properties together with a low order of toxicity render the pyranoindoles and thiopyranoindoles of the invention therapeutically useful.

2. Description of the Prior Art

Only a rather limited number of reports dealing with pyrano[3,4-b]indole derivatives are available. In the few that do exist, pyranoindoles are treated more in the manner of chemical curiosities. For the most part these reports discuss the preparation of pyranoindoles in which the pyran portion thereof exists as a lactone. For example, see H. Plieninger, Chem. Ber., 83, 271 (1950) and S. Sakurai and T. Ito, Nippon Kagaku Zasshi, 78, 1665 (1957); [Chem Abstr., 54, 1488f (1960)].

The thiopyranoindoles of the prior art, for example, 5-(3-aminopropyl)-1,3,4,5-tetrahydrothiopyrano[4,3-b]indole, M. E. Freed, et al., J. Med. Chem., 7, 628 (1964) are distinguished from the present compounds of this invention by having a different ring structure and by lacking substituents on the thiopyran ring.

SUMMARY OF THE INVENTION

The pyranoindole and thiopyranoindole derivatives of this invention are characterized by having an amino(-lower)alkyl radical attached to a pyrano[3,4-b]indole or thiopyrano[3,4-b]indole nucleus. The preferred derivatives of this invention are represented by formula I,

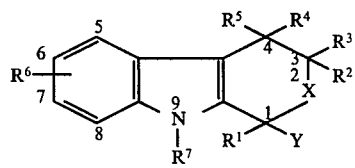

in which $R^1$ is lower alkyl or lower cycloalkyl; $R^2$, $R^3$, $R^4$ and $R^5$ are the same or different selected from the group consisting of hydrogen and lower alkyl; $R^6$ is hydrogen, lower alkyl, hydroxy, lower alkoxy, lower alkanoyloxy, nitro or halo; $R^7$ is hydrogen, lower alkyl, lower alkenyl, propargyl, phenyl(lower)alkyl or an amino(lower)alkyl radical of formula —Alk—$NR^8R^9$ wherein Alk is an alkylene selected from the group consisting of $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ wherein $R^{10}$, $R^{11}$, $R^{12}$, $R^{13}$, $R^{14}$, $R^{15}$, $R^{16}$ and $R^{17}$ are hydrogen or lower alkyl and $R^8$ and $R^9$ are either the same or different selected from the group consisting of hydrogen and lower alkyl, or $R^8$ and $R^9$ together with the nitrogen atom to which they are joined form a heterocyclic amine radical selected from the group consisting of 1-pyrrolidinyl, piperidino, morpholino, piperazino, 4-(lower alkyl)-1-piperazinyl and 4-[hydroxy(lower)alkyl]-1-piperazinyl; X is oxy or thio; and Y is lower alkyl, phenyl(lower)alkyl or an amino(lower)alkyl radical of formula —Alk—$NU^8R^9$ wherein Alk is an alkylene selected from the group consisting of $CR^{10}R^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ wherein $R^{10}$, $R^{11}$, $R^{12}$, $R^{13}$, $R^{14}$, $R^{15}$, $R^{16}$ and $R^{17}$ are hydrogen or lower alkyl and $R^8$ and $R^9$ are as defined herein; with the proviso that at least one of $R^7$ and Y is —Alk—$NR^8R^9$.

In the above definitions it is understood that Alk, $R^8$ and $R^9$ in each case are entitled to the full range of their definitions as listed above, so that Alk, $R^8$ and $R^9$ of Alk—$NR^8R^9$ linked to position 9 need not necessarily be the same as Alk, $R^8$ and $R^9$ of Alk—$NR^8R^9$ linked to position 1.

DETAILED DESCRIPTION OF THE INVENTION

The term "lower alkyl" as used herein contemplates both straight and branched chain alkyl radicals containing from one to six carbon atoms and includes methyl, ethyl, propyl, isopropyl, butyl, isobutyl, 2-methylpentyl and the like.

The term "lower alkenyl" as used herein contemplates both straight and branched chain alkenyl radicals containing from two to six carbon atoms and includes vinyl, allyl, 1-propenyl, methallyl, 2-ethyl-3-butenyl and the like.

The term "phenyl(lower)alkyl" as used herein contemplates a phenylalkyl radical in which the alkyl portion thereof contains from one to four carbon atoms and includes benzyl, phenethyl, α-methylphenethyl and the like.

The term "lower cycloalkyl" as used herein contemplates saturated cyclic hydrocarbon radicals containing from three to six carbon atoms and includes cyclopropyl, cyclobutyl, cyclopentyl and the like.

The term "lower alkoxy" as used herein contemplates both straight and branched chain alkoxy radicals containing from one to four carbon atoms and includes methoxy, ethoxy, isopropoxy and the like.

The term "lower alkanoyloxy" as used herein contemplates both straight and branched chain alkanoyloxy radicals containing from two to six carbon atoms and includes acetoxy, propionyloxy, hexanoyloxy and the like.

The term "halo" as used herein contemplates halogens and includes fluorine, chlorine, bromine and iodine.

The compounds of formula I are capable of forming acid addition salts with pharmaceutically acceptable acids. Such acid addition salts are included within the scope of this invention.

The acid addition salts are prepared by reacting the base form of the appropriate compound of Formula I with either one to four equivalents, depending on the number of basic nitrogens in the compound, or preferably with an excess of the approprite acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formula I which result from asymmetric centers, contained therein. These isomeric forms are prepared by different methods and are purified readily by crystallization or chromatography.

Individual optical isomers, which might be separated by fractional crystallization of the diastereoisomeric salts formed thereof, for instance, with d- or l- tartaric acid or D-(+)-α-bromocamphor sulfonic acid, are also included.

Antidepressant Activity

The useful antidepressant activity of the compounds of formula I and their acid addition salts with pharmaceutically acceptable acids are demonstrated in standard pharmacologic tests, such as, for example, the tests described by F. Hafliger and V. Burckhart in "Psychopharmacological Agents", M. Gordon, Ed., Academic Press, New York and London, 1964, pp. 75 - 83.

More specifically, as noted in the latter reference the antidepressant properties of a compound may be demonstrated by its capacity to antagonize the depresssant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 100 mg/kg. Several of the preferred compounds, for instance, 1-[(2-dimethylamino)ethyl]-1-methyl-1,3,4,9-tetrahydropyrano 3,4-b]indole oxalate (Example 309), 1-methyl-[3-(methylamino)propyl]-1,3,4,9-tetrahydropyrano-[ 3,4-b]indole oxalate (Example 310), 1-[3-(dimethylamino)propyl]-1-methyl-1,3,4,9-tetrahydropyrano-[ 3,4-b]indole oxalate (Example 312), 1-[2-(dimethylamino)ethyl]-1-propyl-1,3,4,9-tetrahydropyrano-[ 3,4-b]indole maleate (Example 330), and 1-[2-(dimethylaminoethyl]-1-methyl-9-propyl-1,3,4,9-tetrahydropyrano-[ 3,4-b]indole maleate (Example 683), antagonize the effects of reserpine in mice at dose ranges from about 1 to 15 mg/kg.

When the compounds of this invention are used as antidepressants in warm-blooded mammals, e.g. rats and mice, they may be used alone or in combination with pharmacologically acceptable carriers, the proportion of which is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generaly, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.1 mg to about 50 mg per kilo per day, although as aforementioned variations will occur. However, a dosage level that is in the range of from about 0.5 mg to about 25 mg per kilo per day is most desirably employed in order to achieve effective results.

Antiulcer Activity

The compounds of formula I of this invention possess another useful pharmacologic property; that is, they are useful antiulcer agents. More particularly, the said compounds of this invention exhibit antiulcer activity in standard pharmacologic tests, for example, the test described by D. A. Brodie and L. S. Valitski, Proc. Soc. Exptl. Biol. Med., 113, 998 (1963), based on the prevention of stress-induced ulcers.

When the compounds of formula I are employed as antiulcer agents, they may be formulated and administered in the same manner as described above for their use as antidepressant agents.

Processes

For the preparation of the pyranoindole and thipyranoindole derivatives of this invention we prefer to use as starting materials the compounds of general formula II,

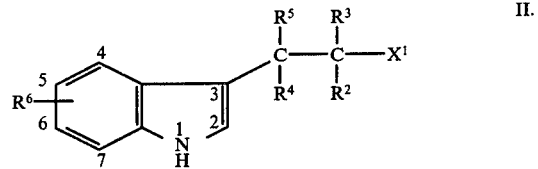

in which $R^2$, $R^3$, $R^4$, $R^5$ and $R^6$ are as defined in the first instance and $X^1$ is hydroxy or mercapto.

The starting materials of formula II in which $X^1$ is hydroxy are either known, for example, tryptophol, described by H. R. Snyder and F. J. Pilgrim, J. Am. Chem. Soc. 70, 3770 (1948), or they are obtained by the following process:

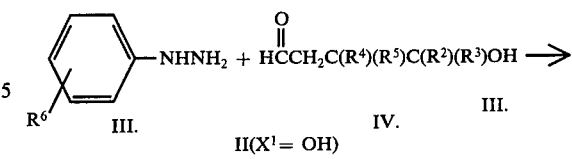

With reference to this process phenylhydrazines of formula III and the hydroxyaldehyde of formula IV are reacted together according to the conditions of the "Fischer Indole Synthesis", for example, see P. L. Julian, E. N. Myer and H. C. Printy, "Heterocyclic Compounds", R. C. Elderfield, Ed., Vol. 3, John Wiley and Sons, Inc., New York, 1952, pp. 8 - 11, to form the desired starting material (II, $X^1$ = OH).

The phenylhydrazines of formula III are either known or are prepared according to known methods. A convenient method involves the diazotization of the appropriately substituted aniline to give the corresponding diazo derivative. The latter compound is then reduced with stannous chloride or sodium sulfite to give the corresponding phenylhydrazine, see L. F. Fieser and M. Fieser, "Advanced Organic Chemistry", Reinhold Publishing Corporation, New York, 1961, p. 734.

The hydroxyaldehydes of formula IV are either known, see for example, "Rodd's Chemistry of Carbon Compounds", S. Coffey, Ed., Vol. I d, 2nd ed., Elsevier Publishing Co., Amsterdam, 1965, pp. 44 – 49, or they are prepared according to known methods. A convenient method involves reduction of an appropriate lactone of formula

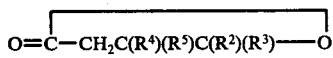

with bis-(3-methyl-2-butyl)borane, H. G. Brown and D. B. Bigley, J. Am. Chem. Soc., 83, 486 (1961), diisobutyl aluminum hydride, L. I. Zakharkkin and I. M. Khorlina, Tetrahedron Letters, 619 (1962) or sodium aluminum hydride, L. I. Zakharkin et al., Tetrahedron Letters, 2087 (1963). The appropriate lactones utilized in this condensation are either commercially available, for example, δ-valerolactone, α-methyl-butyrolactone, or they are described with a variety of methods for their preparation in organic chemistry textbooks; such as the textbooks, "Methoden der Organischen Chemie", Houben-Weyl, E. Muller, Ed., Vol. VI/2, Georg Thieme Verlag, Stuttgart, 1963, pp. 561 – 852 or L. F. Fieser and M. Fieser, "Advanced Organic Chemistry", cited above.

Alternatively, the starting materials of formula II in which $R^2$, $R^3$ and $R^4$ are hydrogen and $X^1$ is hydroxy are prepared by lithium aluminum hydride reduction (N. G. Gaylord, "Reduction with Complex Metal Hydrides", Interscience Publishers, Inc., New York, 1956, pp. 322 – 370) of compounds of formula V described by T. Y. Shen, U.S. Pat. No. 3,161,654, Dec. 15, 1964:

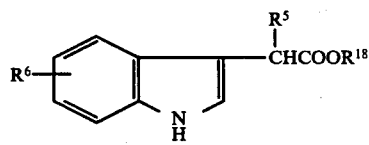

wherein $R^{18}$ is lower alkyl and $R^5$ and $R^6$ are as defined in the first instance.

In addition, convenient processes are available for the specific synthesis of certain starting materials of formula II. For example, starting materials of formula II in which $R^2$, $R^3$, $R^4$ and $R^5$ are hydrogen and $X^1$ is hydroxy are obtained by reduction of the appropriate ethyl 3-indoleglyoxylate with lithium aluminum hydride, British Patent 778,823 and T. Nogrady and T. W. Doyle, Can. J. Chem., 42, 485 (1964). Starting materials of formula II in which $R^2$ and $R^4$ are hydrogen, $R^3$ and $R^5$ are hydrogen or lower alkyl and $X^1$ is hydroxy are obtained by reacting indole or an appropriately substituted indole with ethylene oxide or lower alkyl substituted ethylene oxide according to the process of M. Julia et al., Bull. Soc. Chim. Fr., 2291 (1966).

The starting materials of formula II in which $X^1$ is mercapto and $R^2$, $R^3$, $R^4$, $R^5$ and $R^6$ are as defined in the first instance are obtained by the following process: The appropriate compound of formula II ($X^1 =$ OH) described above, is treated with phosphorus tribromide in an inert solvent, for example, ether or carbon tetrachloride, to afford the corresponding 3-(2-bromoethyl)-indole derivative. The latter compound is then converted to the desired starting material of formula II ($X^1$ = SH) by a procedure similar to that described by N. N. Suvorov and V. N. Buyanov, Khim.-Farm. Zh., 1, (1967), [Chem. Abstr. 67, 73474a (1967)], for converting 3-(2-bromoethyl)indole to indole-3-ethanethiol (II; $R^2$, $R^3$, $R^4$, $R^5$ and $R^6$ = H and $X^1$ = SH). Accordingly, the appropriate 3-(2-bromoethyl)-indole derivative is treated with sodium or potassium thiosulfate to afford the corresponding sodium or potassium β-(3-indolyl)ethyl thiosulfate derivative, respectively, which on treatment with strong alkali for example, sodium or potassium hydroxide, is transformed into the corresponding bis-[ω-(3-indolyl)ethyl]disulfide derivative. Reduction of the latter compound with lithium aluminum hydride gives the desired compounds of formula II.

It should be noted that the preceding process may not be entirely practical for the preparation of the compounds of formula II in which $X^1$ is mercapto and $R^6$ is hydroxy or loer alkanoyloxy. For this reason, the preferred starting materials or formula II for the ultimate preparation of the compounds of formula I in which $R^6$ is hydroxy or lower alkanoyloxy and X is thio are the corresponding compounds of formula II in which $R^6$ is benzyloxy, i.e., a hydroxyl with a protecting benzyl group or other suitable protecting group, see J. F. McOmie, "Advances in Organic Chemistry," Vol. 3, R. A. Raphael, et al, Ed., Interscience Publishers, New York, 1963, pp. 191 – 294. When the latter compounds are used as starting materials in this manner, they are first subjected to the process (II + VI→VII), described below. Subsequently, the benzyloxy group is removed by hydrogenation, in the presence of a catalyst, for example, 10% palladium on carbon, just prior to affording the desired corresponding compound of formula I in which $R^6$ is hydroxy. The latter are converted, if desired, to the corresponding compound of formula I in which $R^6$ is lower alkanoyloxy by conventional means, for example, by treatment with the appropriate lower alkanoic anhydride preferably in the presence of pyridine. Likewise, it should be noted that similar use of the starting materials of formula II in which $X^1$ is hydroxy and $R^6$ is benzyloxy to obtain the corresponding compound of formula I in which $R^6$ is hydroxy or lower alkanoyloxy is also preferred.

The above described starting materials of formula II in which $R^2$, $R^3$, $R^4$, $R^5$, $R^6$ and $X^1$ are as defined in the first instance are now subjected to a key reaction comprising the treatment of said starting materials with a compound of formula

in which $R^1$ is as defined in the first instance and Z is selected from the group consisting of:

a. COOR$^{19}$ and Alk$^1$— COOR$^{19}$ in which R$^{19}$ is hydrogen or lower alkyl and Alk$^1$ is an alkylene selected from the group consisting of CR$^{10}$R$^{11}$, CR$^{10}$R$^{11}$CR$^{12}$R$^{13}$ and CR$^{10}$R$^{11}$CR$^{12}$R$^{13}$CR$^{14}$R$^{15}$ wherein R$^{10}$, R$^{11}$, R$^{12}$, R$^{13}$, R$^{14}$ and R$^{15}$ are hydrogen or lower alkyl, b. $CONR^8R^9$ and $Alk^1$—$CONR^8R^9$ in which $Alk^1$, $R^8$ and $R^9$ are as defined above, c. $CH_2OCOR^{20}$ and $Alk^1$—$CH_2OCOR^{20}$ in which $R^{20}$ is hydrogen or lower alkyl and $Alk^1$ is as defined above, d. $Alk^2$—L in which $Alk^2$ is an alkylene selected from the group consisting of $CR^{10}R^{11}CHR^{12}$, $CR^{10}R^{11}CR^{12}R^{13}CHR^{14}$ and $CR^{10}R^{11}CR^{12}R^{13}CR^{14}R^{15}CHR^{16}$ wherein $R^{10}$, $R^{11}$, $R^{12}$, $R^{13}$, $R^{14}$, $R^{15}$ and $R^{16}$ are as defined above and L is halo, e. $Alk\ NR^8COR^{21}$ in which Alk and $R^8$ are as defined in the first instance and $R^{21}$ is hydrogen or lower alkyl containing from one to five carbon atoms, f. $Alk - NO_2$ in which Alk is as defined in the first instance, and g. Lower alkyl and phenyl(lower)alkyl, in the presence of an acid catalyst to yield the compounds of formula VII in which $R^1$, $R^2$, $R^3$, $R^4$, $R^5$, $R^6$, X and Z are as defined above and $R^7$ is hydrogen.

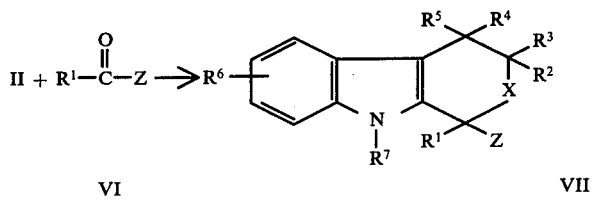

VI            VII

Thereafter the appropriate compound of formula VII ($R^7 = H$) is converted to the desired pyranoindole of formula I according to the processes described hereinafter.

In practising the condensation (II + Vi →VI) we have found it preferable to use a solvent as a reaction medium. Any solvent inert to the reaction conditions may be used. Suitable solvents includes aromatic hydrocarbon, for example benzene, or toluene, ethers and cyclic ethers, for example diethyl ether, dioxan, or tetrahydrofuran, halogenated hydrocarbons, for example methylene dichloride, or carbon tetrachloride and the like. Benzene and tetrahydrofuran are especially convenient and practical for this use. A variety of suitable acid catalysts may be used for this condensation, for example, the type of catalyst used in a Friedel-Crafts reaction, i.e. p-toluenesulfonic acid, aluminum chloride, phosphorus pentoxide, boron trifluoride, zinc chloride, hydrochloric acid, perchloric acid, trifluoroacetic acid, sulfuric acid and the like. p-Toluenesulfonic acid, aluminum chloride, boron trifluoride and phosphorus pentoxide are included among the preferred acid catalysts. The amount of acid catalysts used is not especially critical and may range from 0.01 molar equivalents to 100 molar equivalents; however, a range of from 0.1 to 10 molar equivalents is generally preferred. The time of the reaction may range from 10 minutes to 60 hours, with the preferred range being from one-half to 24 hours. The temperature of the reaction may range from 20° C. to the boiling point of the reaction mixture. Preferred temperature ranges include 20° to 120° C.

A more detailed description of the preparation of the above intermediate compounds of formula VII and a description of their subsequent conversion to pyranoindole and thiopyranoindole derivatives of formula I are disclosed below. For convenience these descriptions are catagorized into sections according to the group selected for Z for the intermediate.

A. Preparation and Conversion of Intermediates of Formula VII (Z = $COOR^{19}$ and $Alk^1$—$COOR^{19}$)

Intermediates of formula VII (Z = $COOR^{19}$ and $Alk^1$— $COOR^{19}$ in which $R^{19}$ is hydrogen or lower alkyl and $Alk^1$ is as defined in the first instance, $R^7$ is hydrogen and $R^1$, $R^2$, $R^3$, $R^4$, $R^5$, $R^6$ and X are as defined in the first instance) are readily obtained by the condensation (II + VI→VII) by using ketoacids or ketoesters of formula

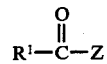

in which $R^1$ is as defined in the first instance and Z is $COOR^{19}$ or $Alk^1$ — $COOR^{19}$ as defined above together with the starting material of formula II.

Generally comparable yields of product are obtained in this process when either the ketoacid or the corresponding ketoester is used. However, in the case where it is desired to prepare an acid compound of formula VII($R^7$ = H) in which Z is $Alk^1COOR^{19}$ wherein $Alk^1$ is $CR^{10}R^{11}$ and $R^{19}$ is hydrogen (i.e., an acid intermediate of formula VII), it is preferable to first condense the appropriate β-ketoester of formula VI rather than the corresponding β-ketoacid and then hydrolyze the resulting ester product to give the desired acid compound.

Moreover, in the general practise of this invention it is often more convenient to prepare the acid compounds of formula VII($R^7$=H) by using the ketoester instead of the ketoacid in this process and then hydrolyze the resulting ester product to the desired acid, the reason being simply that the ketoesters are generally more readily available either commercially or by synthesis.

The hydrolysis of compounds of formula VII($R^7$=H) in which Z is $COOR^{19}$ or $Alk^1\ COOR^{19}$ wherein $Alk^1$ is as defined in the first instance and $R^{19}$ is lower alkyl, i.e. ester intermediates of formula VII($R^7$=H), to their corresponding acids of formula VII ($R^7$ = H) is readily effected by treatment with a suitable alkali, for example, potassium hydroxide or sodium carbonate, in aqueous methanol or aqueous ethanol or by treatment with lithium iodide in a suitable organic solvent, for example, collidene, see L. F. Fieser and M. Fieser, "Reagents for Organic Synthesis," John Wiley and Sons, Inc., New York, 1967, pp. 615 - 617.

The α-, β-, γ- and δ-ketoacids and -ketoesters of formula VI are either known, for example, ethyl pyruvate, levulinic acid, ethyl α,α-dimethylacetoacetate, and β,β-dimethyllevulic acid or they are prepared by known methods described in general organic chemistry textbooks. For example, a comprehensive review on the properties and preparation of such α-, β-, γ- and δ-ketoacids and -ketoesters may be found in "Rodd's Chemistry of the Carbon Compounds," cited above, Vol. Id, pp. 226 - 274.

Thereafter these intermediate acids and esters of formula VII($R^7$ = H) are converted to compounds of formula I in which $R^1$, $R^2$, $R^3$, $R^4$, $R^5$, $R^6$, $R^7$ and X are as defined in the first instance and Y is -$Alk-NR^8R^9$ in which Alk is $CH_2$ or $Alk^1$—$CH_2$ wherein $Alk^1$ is as defined in the first instance and $R^8$ and $R^9$ are as defined in the first instance. This conversion is accomplished by amidation, reduction and if desired N-alkylation of the indolic nitrogen. The order of these steps is not critical.

However, we have found the following sequence of these steps to be both convenient and practical.

First, when it is desired to prepare the derivatives of the latter group of compounds of formula I in which $R^7$ is H, i.e., N-alkylation of the indolic nitrogen is not desired, either the above acid intermediate or ester intermediate may be employed.

In the case where the acid intermediate of formula VII($R^7 =$ H) is employed, said acid is subjected to amidation by treatment with a lower alkyl chloroformate, preferably ethyl chloroformate, in the presence of triethylamine, affording the corresponding mixed anhydride, which is converted by treatment with the appropriate amine of formula $HNR^8R^9$ in which $R^8$ and $R^9$ are as defined in the first instance, for example, ammonia, methylamine or dimethylamine, to yield the corresponding amide of formula VII in which Z is $CONR^8R^9$ or $Alk^1CONR^8R^9$ in which $Alk^1$, $R^8$ and $R^9$ are as described in the first instance.

Alternatively, the latter amides are also obtained by treating the ester intermediates of formula VII ($R^7 =$ H) with the appropriate amine according to known amidation methods, for example, see A. L. F. Beckwith in "The Chemistry of Amides", J. Zalicky, Ed., Interscience Publishers, New York, 1970, pp. 96 – 105.

Secondly, the amides so obtained are reduced with a suitable complex metal hydride to yield the desired pyranoindoles and thiopyranoindoles. Examples of suitable complex metal hydrides are lithium aluminum hydride, lithium aluminum hydride-aluminum chloride, aluminum hydride-aluminum chloride, diborane and sodium borohydride-aluminum chloride. Lithium aluminum hydride is preferred.

On the other hand when it is desired to prepare the compounds of formula I of the above group in which $R^1$, $R^2$, $R^3$, $R^4$, $R^5$, $R^6$ and X are as defined in the first instance, $R^7$ is lower alkyl, or lower alkenyl, propargyl, phenyl(lower)alkyl or amino(lower)alkyl and Y is $-Alk-N\ R^8R^9$ in which Alk is $CH_2$ or $Alk^1CH_2$ wherein $Alk^1$ is as defined in the first instance and $R^8$ and $R^9$ are as defined in the first instance, the acid or ester intermediate of formula VII($R^7 =$ H) are first subjected to N-alkylation by treatment with a molar excess of the appropriate organic halide, namely a lower alkyl halide, lower alkenyl halide, propargyl halide, phenyl(lower)alkyl halide or amino(lower)alkyl halide, respectively, in an inert solvent in the presence of a proton acceptor. Suitable inert solvent include tetrahydrofuran, benzene, toluene and dimethylformamide. Suitable proton acceptors include sodium hydride, alkali metal carbonate and triethylamine. Preferred conditions for effecting this N-alkylation include the use of sodium hydride as a proton acceptor and tetrahydrofuran as an inert solvent. Although the optimum temperature and reaction time will vary depending on the reactants employed, the reaction is generally performed at the boiling point of the reaction mixture for a period of 30 minutes to 48 hours.

The lower alkyl halides, lower alkenyl halides, propargyl halide, phenyl(lower)alkyl halides and aminoalkyl(lower)halides employed herein are either known, for example, ethyl bromide, allyl bromide and dimethylaminoethyl chloride, or they are prepared by known methods, usually by the treatment of the corresponding alcohols with a halogenating agent, for instance, thionyl chloride, see D. J. Collins and J. J. Hobbs, Aust. J. Chem., 20, 1413 (1967) and R. B. Moffett, J. Org. Chem., 14, 862 (1949).

In this manner, the corresponding N-alkylated derivatives of the above acid and ester derivatives of formula VII are obtained. Thereafter these derivatives are subjected to the amidation and reduction steps according to the conditions described hereinabove in this section, to afford the desired compounds of formula I in which $R^7$ is lower alkyl, lower alkenyl, propargyl, phenyl(lower)alkyl, or amino(lower)alkyl.

Although the above sequence of steps for the conversion of the acid and ester intermediates of formula VII ($R^7 =$ H) to the above desired pyranoindoles is convenient and efficacious, a change in the order of the steps whereby the amides of formula VII ($R^7 =$ H) are treated with the appropriate organic halide according to the N-alkylation conditions described above, followed by reduction with a complex metal hydride, as described above, also affords the above desired compounds of formula I, in which $R^7$ is lower alkyl, lower alkenyl, propargyl, phenyl(lower)alkyl or amino(lower)alkyl, described above, of the resulting corresponding amide derivative in which the indolic nitrogen is alkylated, also affords the above desired compounds of formula I, in which $R^7$ is lower alkyl, lower alkenyl, propargyl, phenyl(lower) alkyl or amino(lower)alkyl.

Furthermore, another change in the order of the steps for preparing the latter compounds of formula I is realized by N-alkylation, as described above, of the corresponding compounds of formula I in which $R^7$ is hydrogen, described above. In this case when the starting material employed is a pyranoindole or thiopyranoindole of formula I in which Y is $-Alk-NR^8R^9$ in which Alk is $CH_2$ or $Alk^1CH_2$ wherein $Alk^1$ is as defined in the first instance and $R^8$ is hydrogen and $R^9$ is hydrogen or lower alkyl, i.e., a primary or secondary amine function is present in the molecule in addition to the indolic nitrogen, it is expedient to use only one molar equivalent of the appropriate organic halide to avoid alkylation of the primary or secondary amine if so desired.

Another aspect of the present intermediates of formula VII relates to their conversion to compounds of formula I in which $R^1$, $R^2$, $R^3$, $R^4$, $R^5$, $R^6$, $R^7$ and X are as described in the first instance and Y is $-Alk-NR^8R^9$ in which Alk is $CH_2$ or $Alk^1CH_2$ wherein $Alk^1$ is as defined in the first instance and $R^8$ is hydrogen and $R^9$ is lower alkyl, i.e. secondary amines. When it is desired to prepare the latter compounds a modification involving the protection of the secondary amine with a benzyl group or other suitable protecting group, see J. F. McOmie, cited below is especially convenient. For example, the aforementioned acid or ester intermediate of formula VII is reacted with an amine of formula $HNR^8R^9$ in which $R^8$ is benzyl and $R^9$ is lower alkyl according to the amidation step described above. The resulting amide is N-alkylated on the indolic nitrogen, if desired, and then reduced with a complex metal hydride according to the above procedures. Thereafter the benzyl group is removed by hydrogenolysis in the presence of a catalyst, preferably 10% palladium on carbon, to afford the desired secondary amine compounds of formula I.

Still another modification relates to a more general reduction of the above amides of formula VII in which Z is $CONR^8R^9$ or $Alk^1$-$CONR^8R^9$ wherein $Alk^1$, $R^8$ and $R^9$ are as defined in the first instance. In other words this modification is applicable to the reduction of tertiary, secondary and primary amides, described herein, and is a preferred modification for the reduction of the latter two. In practising this modification, the aforementioned amide of formula VII is treated with triethyloxonium fluoroborate or dimethyl sulfate, see H. Bredereck, et al., Chem. Ber., 98, 2754 (1965), in an inert solvent, for example, methylene dichloride, whereby the corresponding iminoether fluoroborate or methyl sulfate salt is obtained, respectively. Subsequent reduction of the salt thus obtained with a complex metal hydride, similar to the reduction described previously for the amides, yields the corresponding compounds of formula I. Alternatively, the above fluoroborate or methyl sulfate salt derived from a secondary or primary amide is decomposed by base treatment, for example, with 10% sodium hydroxide or triethylamine, to give the corresponding iminoether which is then reduced in a like manner to the desired compound of formula I.

When applying the aforementioned steps in the preparation of compounds of formula I in which $R^6$ is hydroxy or lower alkanoyloxy, it is preferable to use corresponding intermediates in which $R^6$ is benzyloxy followed by the appropriate transformations as noted previously to yield the desired compounds of formula I.

b. Preparation and Conversion of Intermediates of Formula VII (Z = $CONR^8R^9$ and $Alk^1$—$CONR^8R^9$).

The intermediates of formula VII in which $R^7$ is hydrogen and Z is $CONR^8R^9$ and $Alk^1$—$CONR^8R^9$ wherein $R^8$, $R^9$ and $Alk^1$ are as defined in the first instance, described in the previous section, are also obtained directly by utilizing the appropriate starting materials of Formula II and α-, β-, γ- or δ-ketoamides of formula

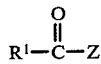

in which $R^1$ is as defined above and Z is $CONR^8R^9$ or $Alk^1$—$CONR^8R^9$ in which $Alk^1$, $R^8$ and $R^9$ are as defined above. The ketoamides required for this condensation are either known, for example, pyruvamide or α,α-dimethylacetoacetamide, or they are prepared by known methods, for instance, see "Rodd's Chemistry of the Carbon Compounds," cited above, Vol. 1d, pp. 226-274.

Thereafter these amides are converted by the reduction process, described above, to the compounds of formula I in which $R^1$, $R^2$, $R^3$, $R^4$, $R^5$, $R^6$, and X are as defined in the first instance, $R^7$ is hydrogen and Y is —Alk—$NR^8R^9$ in which Alk is $CH_2$ or $Alk^1$—$Ch_2$ wherein $Alk^1$ is as defined in the first instance and $R^8$ and $R^9$ are as defined in the first instance.

c. Preparation and Conversion of Intermediates of Formula VII (Z = $CH_2OCOR^{20}$ and $Alk^1$—$CH_2OCOR^{20}$)

Intermediates of formula VII in which $R^7$ is hydrogen and Z is $CH_2OCOR^{20}$ and $Alk^1$—$CH_2OCOR^{20}$ in which $Alk^1$ and $R^{20}$ are as defined in the first instance, are obtained when a starting material of formula II is condensed with a ketoalcohol lower alkanoic acid ester of formula $R^1COCH_2OCOR^{20}$ or $R^1CO$—$Alk^1$—$CH_2OCOR^{20}$ in which $R^1$, $Alk^1$ and $R^{20}$ are as defined in the first instance in the presence of a suitable acid catalyst according to the conditions described above for the condensation (II+VI→VII). The ketoalcohol lower alkyl esters are either known, for example, acetonyl acetate or 5-acetoxypentan-2-one, or are prepared by known methods, for instance, see "Rodd's Chemistry of the Carbon Compounds," cited above, Vol. 1d, pp. 49-54.

These intermediates of formula VII may then be utilized for the preparation of compounds of formula I of this invention in the following manner. The intermediate is hydrolyzed with an aqueous alcoholic solution of a suitable alkali, for example, sodium hydroxide in aqueous methanol to afford the corresponding primary alcohol. The primary alcohol is then oxidized to the corresponding aldehyde. Although a variety of methods are known for the oxidation of a primary alcohol to its corresponding aldehyde, see for example, "Rodd's Chemistry of the Carbon Compounds", cited above, Vol. 1c, pp. 4 - 10, we have found that the method of K. E. Pfitzner and J. G. Moffat, J. Am. Chem. Soc., 87, 5670 (1965), using N,N-dicyclohexylcarbodimide and dimethyl sulfoxide in the presence of a suitable acid, for example, trifluoroacetic acid, is both efficacious and convenient. Thereafter the aldehyde is reacted with an amine of formula $HNR^8R^9$ in which $R^8$ and $R^9$ are as defined in the first instance to give the corresponding Schiff base, which is reduced with sodium borohydride, see E. Schenker, Angew. Chem., 73, 81 (1961), to yield compounds of formula I in which $R^1$, $R^2$, $R^3$, $R^4$, $R^5$, $R^6$ and X are as defined in the first instance, $R^7$ is hydrogen and Y is —Alk—$NR^8R^9$ in which Alk is $CH_2$ or $Alk^1$—$CH_2$ and $R^8$ and $R^9$ are as defined in the first instance.

Alternatively, the latter compounds of formula I are obtained by converting the above corresponding alcohol to a reactive intermediate such as the corresponding halide, mesylate or tosylate, which are then reacted with a two molar excess of an amine of formula $HNR^8R^9$ in which $R^8$ and $R^9$ are as defined in the first instance. Preferably this reaction is performed in a suitable inert solvent, for example, tetrahydrofuran, at the boiling point of the reaction mixture for a period of 8 to 24 hours. In connection with alkylations of amines of formula $HNR^8R^9$ in which $R^9$ is hydrogen and $R^9$ is lower alkyl as disclosed herein, it is generally preferable to perform the alkylation with the corresponding N-benzyl derivative of said amine, i.e., an amine of formula $NHR^8R^9$ in which $R^8$ is benzyl and $R^9$ is lower alkyl. Thereafter, when all appropriate transformation have been performed, the N-benzyl group is removed by hydrogenolysis with a catalyst, preferably 10% palladium on carbon, to give the desired compounds of formula I.

Thereafter, and if desired, these latter compounds of formula I are converted to their corresponding derivatives in which $R^7$ lower alkyl, lower alkenyl, propargyl, phenyl(lower)allyl or amino(lower)alkyl by N-alkylation with one molar equivalent of the appropriate or organic halide in the manner described for the N-alkylation in section (a).

Alternatively, the above aldehyde is oxidized with a suitable oxidizing agent to yield the corresponding acid intermediates of formula VII ($R^7$ = H) described in section (a). Although a variety of suitable oxidizing agents may be used for this purpose, for example, silver oxide, alkaline permanganate, hydrogen peroxide, we prefer to use silver oxide according to the method of M. Delepine and P. Bonnet, Compt. rend., 149, 39 (1909).

Again alternatively, the above aldehyde is converted to its oxime which on reduction with a complex metal hydride yields the corresponding primary amine of formula I in which $R^1$, $R^2$, $R^3$, $R^4$, $R^5$, $R^6$ and X are as defined in the first instance, $R^7$ is hydrogen and Y is —Alk—$NR^8R^9$ in which Alk is $CH_2$ or Alk—$^1CH_2$ wherein Alk$^1$ is as defined in the first instance and R$^8$ and R$^9$ are hydrogen.

If desired those latter primary amine compounds of formula I may be N-alkylated on the indolic nitrogen in the manner described above with a molar equivalent of the appropriate organic halide to give the corresponding compounds of formula I in which R$^7$ is lower alkyl, lower alkenyl, propargyl, phenyl(lower)alkyl or Alk—NR$^8$R$^9$ wherein Alk, R$^8$ and R$^9$ are as defined in the first instance.

In turn these latter compounds of formula I may be further N-alkylated on the nitrogen of the primary amine with the appropriate lower alkyl halide to the corresponding compounds of formula I in which Y is —Alk—NR$^8$R$^9$ wherein Alk is CH$_2$ or Alk$^1$—CH$_2$ wherein Alk$^1$ is as defined in the first instance and R$^8$ is hydrogen or lower alkyl and R$^9$ is lower alkyl (i.e. secondary or tertiary amines with respect to Y). In this case depending on the particular derivative desired the N-alkylation is effected with one or two moles of the alkyl halide to give respectively the secondary (R$^8$ = H and R$^9$ = lower alkyl with respect to Y)or tertiary amine (R$^8$ = R$^9$ = lower alkyl with respect to Y). On the other hand the N-alkylation may be effected in two steps introducing a different alkyl group each time to afford the corresponding tetiary amine in which R$^8$ and R$^9$ are different lower alkyls with respect to Y.

When it is desired to prepare the above tertiary amine compounds in which R$^8$ or R$^9$ are either or both methyl, an alternative alkylation method comprises reacting the appropriate corresponding primary or secondary amine with an aqueous mixture of a substantial excess of formaldehyde and formic acid according to the conditions of the Eschweiler-Clarke reaction, see M. L. Moore, Organic Reactions, 5, 301 (1949), whereby N-methylation is effected.

Another N-alkylation method which is applied to the above primary and secondary amines involves acylation with a lower alkanoic anhydride or acid halide and subsequent reduction of the resulting amide.

Furthermore, the above primary amines are used to prepare compounds of formula I in which Y is —Alk—NR$^8$R$^9$ wherein Alk is CH$_2$ or Alk$^1$—CH$_2$ and R$^8$ and R$^9$ together with the nitrogen atom to which they are joined from a heterocyclic amine radical as defined in the first instance. When used in this manner the primary amines are subjected to known N-alkylation methods, for example, see method J in Moffett, cited above, with the appropriate α,ω-dibromides, for example, tetramethylene dibromide, pentamethylene dibromide, bis(2-chloroethyl)ether, bis(2-chloroethyl)benzylamine followed by hydrogenation in the presence of 10% palladium on carbon to remove the protecting benzyl group, a bis(2-chloroethyl)lower alkylamine or a bis(2-chloroethyl)-N-[hydroxy(lower)alkyl]amine, to give the corresponding, desired compound of formula I wherein Y is an amino(lower)alkyl in which the amino portion thereof is pyrrolidino, piperidino, morpholino, piperazino, 4-(lower)alkyl-1-piperazinyl or 4-[hydroxy(lower-)alkyl]-1-piperazinyl, respectively.

If during the above N-alkylations it is desired to protect primary or secondary amine functions that are present in the R$^7$ portion of compounds of formula I, such protection may be afforded by the use of appropriate protecting groups, for example, a benzyl group; see also, J. F. W. McOmie in "Advances in Organic Chemistry," Vol. 3, R. A. Raphael, et al., Ed., Interscinece Publishers, New York, 1963, pp. 191–294.

d. Preparation and Conversion of Intermediates of Formula VII (Z = Alk$^2$—L).

Intermediates of formula VII in which R$^7$ is hydrogen and Z is Alk$^2$—L wherein Alk$^2$ and L are as defined in the first instance, are obtained when a starting material of formula II is condensed with a β,γ- or δ-haloketone of formula R$^1$CO—Alk$^2$—L in which R$^1$, Alk$^2$ and L are as defined in the first instance in the presence of a suitable acid catalyst according to the conditions described above for the condensation (II+VI→VII). The haloketones are either known, for example, 4-chlorobutan-2-one, or they are prepared by known methods, for instance, see "Rodd's Chemistry of Carbon Compounds," cited above, Vol. 1c, pp. 70–71 and "Methoden der Organischen Chemie," Houben-Weyl, E. Müller, Ed., Vol. V/3, Georg Thieme Verlag, Stuttgart, 1962, pp. 511–1076.

Thereafter these intermedates of formula VII are treated with a two molar excess of an amine of formula HNR$^8$R$^9$ in which R$^8$ and R$^9$ are as defined in the first instance to yield the compounds of formula I in which R$^1$, R$^2$, R$^3$, R$^4$, R$^5$, R$^6$ and X are as described in the first instance, R$^7$ is hydrogen and Y is —Alk—NR$^8$R$^9$ in which Alk is Alk$^2$ as defined in the first instance and R$^8$ and R$^9$ are as defined in the first instance. Preferred conditions for this reaction include the use of a suitable inert solvent, for example, tetrahydrofuran, temperatures ranging from 40°–100° C. or at the boiling point of the reaction mixture and a reaction time of from 8 to 24 hours.

If desired the latter pyranoindoles and thiopyranoindoles may be N-alkylated on the indolic nitrogen with an appropriate lower alkyl halide or aminoalkyl halide according to the method described for the N-alkylation of the pyranoindoles and thiopyranoindoles in section (a).

e. Preparation and Conversion of Intermediates of Formula VII (Z = AlkNR$^8$COR$^{21}$)

Intermediates of formula VII in which R$^7$ is hydrogen and Z is AlkNR$^8$COR$^{21}$ wherein Alk, R$^8$ and R$^{21}$ are as defined in the first instance are readily obtained by the condenation (II+VI→VII) by using ketoamides of formula

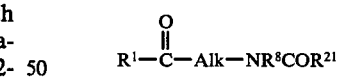

in which R$^1$, Alk, R$^8$ and R$^{21}$ are as defined in the first instance together with the appropriate starting material of formula II.

The ketoamides used herein are either known, for example, formamidoacetone [A. Treibs and W. Sutter, Chem. Ber., 84, 96 (1951)] and see [R. H. Wiley and O. H. Borum, J. Amer. Chem. Soc., 70, 2005 (1948)] or they are prepared by known procedures, for example, see "Methoden der Organischen Chemie", cited above, Vol. XI/1, 1957, especially pp. 58–62, 285–289 and 508–509, and F. F. Blicke, Organic Reactions, 1, 303 (1942).

Thereafter, reduction with a complex metal hydride and if desired N-alkylation of the indolic nitrogen as described in section (a) converts the instant intermediates of formula VII to pyranoindoles of formula I in which R$^1$, R$^2$, R$^3$, R$^4$, R$^5$, R$^6$, R$^7$, X are as defined in the first instance and Y is AlkNR⁸R⁹ in which Alk and R⁸ are as defined in the first instance and R⁹ is lower alkyl.

f. Preparation and Conversion of Intermediates of Formula VII (Z = Alk — NO₂)

Intermediates of formula VII in which R⁷ is hydrogen and Z is Alk-NO₂ wherein Alk is as defined in the first instance, are obtained by the condensation (II+VI→·VII) when the starting materials of formula II and appropriate α-, β-, γ- , and δ-nitroketones of formula

in which R¹ and Alk are as defined in the first instance are employed therein in the presence of a suitable acid catalyst. In this case trifluoroacetic acid is the preferred acid catalyst.

The nitroketones used herein are either known, for example, 1-nitro-2-propanone, N. Levy and C. W. Scaife, J. Chem. Soc., 1100, (1946) and 5-nitro-2-hexanone, H. Shechter, et al., J. Amer. Chem. Soc. 74, 3664 (1952) or they are prepared by known methods, for example, see Levy, and Scaife, cited above, Shechter, et al. cited above, "Rodd's Chemistry of Carbon Compounds," cited above, Vol. 1c, pp. 71–72 and "Methoden der Organischen Chemie," cited above, Vol. X/1, 1971, p. 203.

Thereafter, these intermediates of formula VII are reduced with a complex metal hydride, preferably lithium aluminum hydride, to afford the pyranoindoles of formula I in which R¹, R², R³, R⁴, R⁵, R⁶ and X are as defined in the first instance, Y is hydrogen and Z is —Alk—NR⁸R⁹ in which Alk is defined in the first instance and R⁸ and R⁹ are hydrogen.

If desired the latter compounds may be N-alkylated according to the methods described in section (c) to give the compounds of formula I in which R¹, R², R³, R⁴, R⁵, R⁶, R⁷ and X are as defined in the first instance and Y is Alk-NR⁸R⁹ in which Alk, R⁸ and R⁹ are as defined in the first instance.

g. Preparation and Conversion of Intermediates of Formula VII (Z = lower alkyl or phenyl(lower)alkyl)

Intermediates of formula VII (Z = lower alkyl or phenyl(lower)alkyl, R⁷ is hydrogen and R¹, R², R³, R⁴, R⁵, R⁶ and X are as defined in the first instance) are readily obtained by the condensation (II+VI→VII) by using the starting materials of formula II and the ketones of formula

in which R¹ is as defined in the first instance and Z is lower alkyl or phenyl(lower)alkyl.

The ketones used herein are either available commercially, for example, acetone or phenylacetone, or they are prepared by conventional methods, for example, see P. Karrer, "Organic Chemistry," 2nd. ed., Elsevier Publishing Co., Inc., New York, 1946, pp. 149–169 and V. Migrdichian, "Organic Synthesis," Vol. 1, Reinhold Publishing Corp., New York, 1957, pp. 100–129.

These intermediates of formula VII are converted to the compounds of formula I in which R¹, R², R³, R⁴, R⁵, R⁶ and X are as defined in the first instance, R⁷ is —(Alk)—NR⁸R⁹ in which Alk, R⁸ and R⁹ are defined in the first instance and Y is lower alkyl or phenyl(lower)alkyl by N-alkylation of the indolic nitrogen with the appropriate amino(lower)alkyl halide according to the method of N-alkylation described in section (a).

Finally, it is the intention to cover all changes and modifications of the embodiment of the invention herein chosen for the purpose of disclosure which are within the scope and spirit of this invention. Such changes and modification include those variations which depend on well known interconversions of amines, amides, acids and esters of alternation of the order of the steps in the processes disclosed herein.

For example, the act of subjecting the corresponding derivative of the starting material of formula II in which the indolic nitrogen is alkylated with a lower alkyl, lower alkenyl, propargyl, phenyl(lower)alkyl or amino(lower)alkyl, to condensation with an appropriate compound of formula VI according to the conditions of the key reaction taught in this present disclosure to yield the corresponding intermediate compound of formula VII in which the indolic nitrogen is so alkylated would not depart from the scope or spirit of this invention.

The following examples illustrate further this invention.

EXAMPLE I

1-METHYL-1,3,4,9-TETRAHYDROPYRANO[3,4-b]INDOLE-1-ACETIC ACID (VII; R¹ = CH₃, R², R³, R⁴, R⁵, R⁶ AND R⁷ = H, X = O and Z = CH₂COOH)

Ethyl acetoacetate (23.4 g., 0.18 moles) is added to a solution of the starting material of formula II, tryptophol (10.0 g., 0.06 moles), in 200 ml. of benzene. After standing for 10 minutes, p-toluenesulfonic acid (1.3 g.) and about 5 g. of hydrated alkali-aluminum silicate (Molecular Sieves No. 4) are added. The mixture is subjected to reflux for thirty minutes, 600 mg. more of p-toluenesulfonic acid is added and refluxing continued for 2½ hours. The molecular sieves are collected and the benzene solution washed successively with 5% sodium bicarbonate and water, dried over sodium sulfate, and evaporated under reduced pressure to dryness affording an oil. The oil is subjected to chromatography on silica gel. Elution with 5% ether in benzene yields the ester, 1-methyl-1,3,4,9-tetrahydropyrano[3,4-b]indole-1-acetic acid ethyl ester, as an oil, $\nu_{max}^{CHCl_3}$ 1715 cm⁻¹.

Hydrolysis of this ester to the title compound is effected as follows: The ester is dissolved in 230 ml. of methanol. To this is added 10 g. of KOH in 30 ml. of H₂O and the solution is allowed to stand at room temperature overnight. The methanol is evaporated, water added and the solution washed with benzene. The aqueous phase is acidified with 6N HCl, and extracted with benzene. This organic phase is washed with water, dried over sodium sulfate and evaporated to dryness to give an oil, which is crystallized from benzene containing a trace of petroleum ether to afford the title compound, m.p. 150° – 152° C., $\nu_{max}^{CHCl_3}$ 3325 and 1705 cm⁻¹.

An equivalent amount of methyl acetoacetate may replace ethyl acetoacetate in the procedure of this Example. In this case, 1-methyl-1,3,4,9-tetrahydropyrano[3,4-b]indoleacetic acid methyl ester, m.p. 87° – 90° C. after recrystallization from benzene-hexane, is obtained as the ester.

An equivalent amount of propyl acetoacetate may replace ethyl acetoacetate in the procedure of this Example. In this case, 1-methyl-1,3,4,9-tetrahydropyrano[3,4-b]indole-1-acetic acid propyl ester is obtained as the ester.

EXAMPLE 2

1-METHYL-1,3,4,9-TETRAHYDROPYRANO[3,4-b]INDOLE-1-PROPIONIC ACID (VII; $R^1$ = $CH_3$, $R^2$, $R^3$, $R^4$, $R^5$, $R^6$ AND $R^7$ = H, X = O AND Z = $CH_2CH_2COOH$)

A mixture of the starting material of formula II, tryptophol (500 mg.), levulinic acid (580 mg.), 75 ml. of benzene, 1.7 g. of phosphorus pentoxide and about 0.5 g. of diatomaceous earth (Celite) is stirred magnetically at room temperature for 15 minutes and then at 70° C. for 1½ hr. The reaction mixture is filtered. The filtrate is washed three times with 5N NaOH; the combined aqueous phase is washed twice with ether and then rendered acidic with cold 50% HCl. The aqueous phase is extracted with chloroform. The chloroform extract is dried ($Na_2SO_4$) and evaporated to dryness. The residue is crystallized from ethyl acetate-petroleum ether to afford the title compound, m.p. 104° - 110° C., nmr ($CDCl_3$) δ 1.47 (3H), 21.8 (4H), 2.74 (2H), 3.96 (2H), 7.18 (4H), 7.85 (1H), 9.60 (1.H).

The above title compound is also obtained by following the procedure of Example 1 but replacing ethyl acetoacetate with an equivalent amount of ethyl levulinate. In this case 1-methyl-1,3,4,9-tetrahydropyrano[3,4-b]indole-1-propionic acid ethyl ester, m.p. 116° - 118° C., $v_{max}^{CHCl_3}$ 1716 $cm^{-1}$, after crystallization from benzene-petroleum ether, is obtained as the ester prior to hydrolysis.

EXAMPLE 3

1-METHYL-1,3,4,9-TETRAHYDROTHIOPYRANO[3,4-b]INDOLE-1-ACETIC ACID (VII; $R^1$ = $CH_3$, $R^2$, $R^3$, $R^4$, $R^5$, $R^6$ AND $R^7$ = H, X = S AND Z = $CH_2COOH$)

Indole-3-ethanediol (1.5 g.) and methyl acetoacetate are mixed with 50 ml. of benzene and the solution heated for 30 min. (bath temperature 70° - 80° C.). p-Toluenesulfonic acid (0.15 g.) is added and the reaction mixture is subjected to reflux and stirring for 12 hours. Water formed in the reaction mixture during this period is collected by a water separator. After cooling the benzene solution is washed with 10% solution of sodium bicarbonate, water, saturated brine and dried over sodium sulfate. Evaporation of the benzene solution yields the ester, 1-methyl-1,3,4,9-tetrahydrothiopyrano[3,4-b]indole-1-acetic acid methyl ester as a semi-solid, $v_{max}^{CHCl_3}$ 1715 $cm^{-1}$.

This ester is then treated with aqueous alcoholic KOH in the manner described for the esters in Example 1 and 2 to afford the title compound, m.p. 147° - 149° C., nmr ($CDCl_3$) δ 1.86 (S, 3H), 306 and 812 (6HH), 7.35 (multiplet, 4H), 8.71 (1H), 10.31 (1H), after recrystallization from benzene-hexane.

The procedures of Examples 1, or 3 are followed to prepare other compounds of formula VII in which $R^1$, $R^2$, $R^3$, $R^4$, $R^5$, $R^6$ and X are as defined in the first instance, $R^7$ is hydrogen and Z is $COOR^{19}$ or $Alk^1$—$COOR^{19}$ wherein $R^{19}$ and $Alk^1$ are as defined in the first instance. Examples of such compounds of formula VII are listed in Tables I and II. In each of these examples an equivalent amount of the starting material of formula II listed therein is used instead of the starting material of formula II described in the procedures of Examples 1 and 3. Note that in each of these examples the ester obtained prior to hydrolysis is a corresponding ester compound of formula VII.

Similarly, the procedure of Example 2 is used to prepare the products listed in Tables I and II. In this case an equivalent amount of the starting material of formula II, listed therein is used instead of the starting material of formula II described in Example 2 and an equivalent amount of the corresponding ketoacid of formula VI is used instead of the ketoester of formula VI listed therein.

TABLE I

| | Starting Material of Formula II | | | | | | Ketoester of Formula VI $R^1$—C(=O)—$Alk^1$—$COOR^{19}$ | | | Product: [(prefix listed below)-1,3,4,9-Tetrahydropyrano-[3,4-b]indole-1-(Suffix Listed Below)] | |
|---|---|---|---|---|---|---|---|---|---|---|---|
| Example | $R^2$ | $R^3$ | $R^4$ | $R^5$ | $R^6$ | X | $R^1$ | $Alk^1$—CO | | $R^{19}$ | Prefix//Suffix |
| 4 | H | H | H | H | H | O | $CH_3$ | CO | | $C_2H_5$ | 1-methyl//carboxylic acid |
| 5 | $CH_3$ | H | H | H | H | O | $C_2H_5$ | CO | | $C_2H_5$ | 1-ethyl-3-methyl//carboxylic acid |
| 6 | n-$C_3H_7$ | H | H | H | 5-$CH_3$ | O | n-$C_3H_7$ | CO | | $CH_3$ | 1,3-diisopropyl-6-methyl//carboxylic acid |
| 7 | $CH_3$ | $CH_3$ | H | H | 5-OH | O | $CH_3$ | CO | | $CH_3$ | 1,3,3-trimethyl-6-hydroxy//carboxylic acid |
| 8 | H | H | H | H | 7-$C_2H_5$ | O | n-$C_3H_7$ | CO | | $CH_3$ | 8-ethyl-1-propyl//carboxylic acid |
| 9 | H | H | i-$C_3H_7$ | H | H | O | ▷ | CO | | $CH_3$ | 1-cyclopropyl-4-isopropyl//carboxylic acid |
| 10 | $CH_3$ | $CH_3$ | $C_2H_5$ | $C_2H_5$ | H | O | ⬠ | CO | | $CH_3$ | 1-cyclopentyl-4,4-diethyl-3,3-dimethyl//carboxylic acid |
| 11 | H | H | $CH_3$ | H | H | O | $CH_3$ | $CH_2CO$ | | $C_2H_5$ | 1,4-dimethyl//acetic acid |
| 12 | H | H | H | H | H | O | $C_2H_5$ | $CH_2CO$ | | $C_2H_5$ | 1-ethyl//acetic acid m.p. 137–140° C. |
| 13 | H | H | H | H | H | O | n-$C_3H_7$ | $CH_2CO$ | | $C_2H_5$ | 1-propyl//acetic acid m.p. 148–151° C. |
| 14 | H | H | H | H | H | O | i-$C_3H_7$ | $CH_2CO$ | | $C_2H_5$ | 1-isopropyl//acetic acid, m.p. 150–152° C. |
| 15 | $CH_3$ | H | H | H | H | O | n-$C_3H_7$ | $CH_2CO$ | | $C_2H_5$ | 3-methyl-1-propyl// |

TABLE I-continued

| | Starting Material of Formula II | | | | | | Ketoester of Formula VI $R^1-\overset{\overset{O}{\|}}{C}-Alk^1-COOR^{19}$ | | | Product: [(prefix listed below)-1,3,4,9-Tetrahydropyrano-[3,4-b]indole-1-(Suffix Listed Below) |
|---|---|---|---|---|---|---|---|---|---|---|
| Example | $R^2$ | $R^3$ | $R^4$ | $R^5$ | $R^6$ | X | $R^1$ | $Alk^1-CO$ | $R^{19}$ | Prefix//Suffix |
| | | | | | | | | | | acetic acid; m.p. 75–80° C. (Isomer A), m.p. 146 – 148° C. (Isomer B). |
| 16 | $CH_3$ | H | $C_2H_5$ | $CH_3$ | H | O | $C_2H_5$ | $CH_2CO$ | $C_2H_5$ | 1,4-diethyl-3-methyl//acetic acid, |
| 17 | H | H | H | H | H | O | $CH_3$ | $CH(CH_3)CO$ | $C_2H_5$ | α,1-dimethyl//acetic acid; m.p. 154–156° C. (Isomer A), m.p. 163–165° C. (Isomer B). |
| 18 | H | H | H | H | H | O |  | $C(CH_3)_2CO$ | $C_2H_5$ | 1-cyclohexyl-α,α-dimethyl//acetic acid |
| 19 | H | H | H | H | H | O | $t-C_4H_9$ | $CH_2CO$ | $C_2H_5$ | 1-t-butyl//acetic acid m.p. 210–212° C. |
| 20 | H | H | H | H | H | O | $n-C_4H_9$ | $CH_2CO$ | $C_2H_5$ | 1-butyl//acetic acid, m.p. 124–127° C. |
| 21 | H | H | H | H | 7-$CH_3$ | O | $n-C_3H_7$ | $CH_2CO$ | $C_2H_5$ | 8-methyl-1-propyl//acetic acid m.p. 127–128° C. |
| 22 | H | H | H | H | 5-Br | O | $C_2H_5$ | $CH_2CO$ | $C_2H_5$ | 6-bromo-1-ethyl//acetic acid m.p. 182–184° C. |
| 23 | H | H | H | H | 5-$OCH_3$ | O | $CH_3$ | $CH_2CO$ | $CH_3$ | 6-methoxy-1-methyl//acetic acid, m.p. 142–143° C. |
| 24 | H | H | H | H | 5-$OCOCH_3$ | O | $CH_3$ | $CH_2CO$ | $C_2H_5$ | 6-acetoxy-1-methyl//acetic acid, m.p. 142–143° C. |
| 25 | H | H | H | H | 5-benzyloxy | O | $CH_3$ | $CH_2CO$ | $C_2H_5$ | 6-benzyloxy-1-methyl//acetic acid, m.p. 163.5° C. |
| 26 | H | H | H | H | 4-$CH_3$ | O | $n-C_3H_7$ | $CH_2CO$ | $C_2H_5$ | 5-methyl-1-propyl//acetic acid, m.p. 177–178° C. |
| 27 | H | H | H | H | 6-$CH_3$ | O | $n-C_3H_7$ | $CH_2CO$ | $C_2H_5$ | 7-methyl-1-propyl//acetic acid, m.p. 157–158° C. |
| 28 | H | H | H | H | 5-$NO_2$ | O | $n-C_3H_7$ | $CH_2CO$ | $C_2H_5$ | 6-nitro-1-propyl//acetic acid, m.p. 119–120° C. |
| 29 | H | H | $CH_3$ | $CH_3$ | H | O | $n-C_3H_7$ | $CH_2CO$ | $C_2H_5$ | 4,4-dimethyl-1-propyl//acetic acid, m.p. 184–185° C. |
| 30 | $CH_3$ | $CH_3$ | H | H | 5-$OC_2H_5$ | O |  | $CH(C_2H_5)CO$ | $C_2H_5$ | 1-cyclopropyl-α,α-diethyl-3,3-dimethyl-6-ethoxy//acetic acid |
| 31 | $CH_3$ | $CH_3$ | $C_2H_5$ | $C_2H_5$ | 6-$C_2H_5$ | O |  | $C(CH_3)_2CO$ | $C_2H_5$ | 1-cyclohexyl-α,α,3,3-tetramethyl-4,4,7-triethyl//acetic acid |
| 32 | $CH_3$ | H | $n-C_3H_7$ | $n-C_3H_7$ | 4-$n-C_3H_7$ | O | $C_2H_5$ | $CH(CH_3)CO$ | $C_2H_5$ | α,3-dimethyl-1-ethyl-4,4,5-tripropyl//acetic acid |
| 33 | H | H | H | H | H | O | $n-C_3H_7$ | $C(CH_3)_2CO$ | $C_2H_5$ | α,α-dimethyl-1-propyl//acetic acid |
| 34 | $C_2H_5$ | $C_2H_5$ | $C_2H_5$ | $C_2H_5$ | 4-$C_2H_5$ | O | $t-C_4H_9$ | $C(i-C_3H_7)_2CO$ | $C_2H_5$ | 1-t-butyl-α,α-diisopropyl-3,3,4,4,5-pentaethyl//acetic acid |
| 35 | H | H | H | H | 4-I | O | $i-C_3H_7$ | $CH_2CH_2CO$ | $C_2H_5$ | 5-iodo-1-isopropyl//propionic acid |
| 36 | $CH_3$ | $CH_3$ | $CH_3$ | $CH_3$ | 7-$O\overset{\overset{O}{\|}}{C}CH_3$ | O | $C_2H_5$ | $CH_2CH(CH_3)CO$ | $C_2H_5$ | 8-acetoxy-1-ethyl-α,3,3,4,4-pentamethyl//propionic acid |
| 37 | H | H | H | H | 6-OH | O | $n-C_3H_7$ | $CH_2C(C_2H_5)_2CO$ | $C_2H_5$ | β,β-diethyl-7-hydroxy-1-propyl//propionic acid |
| 38 | $CH_3$ | H | H | H | 7-$NO_2$ | O |  | $CH(n-C_3H_7)CH_2CO$ | $C_2H_5$ | 1-cyclobutyl-3-methyl-8-nitro-α-propyl//propionic acid |
| 39 | H | H | $CH_3$ | H | 5-$CH_3$ | O |  | $C(CH_3)_2C(CH_3)_2CO$ | $C_2H_5$ | 1-cyclopropyl-α,α,β,β,4,6-hexamethyl//propionic acid |
| 40 | $CH_3$ | H | H | H | H | O | $CH_3$ | $CH_2C(n-C_3H_7)_2CO$ | $C_2H_5$ | 1,3-dimethyl-α,α-dipropyl//propionic acid |
| 41 | $CH_3$ | H | $C_2H_5$ | $C_2H_5$ | H | O | $C_2H_5$ | $CH(CH_3)C(CH_3)_2CO$ | $CH_3$ | α,α,β,3-tetramethyl-1,4,4-triethyl//propionic acid |
| 42 | H | H | $CH_3$ | $CH_3$ | H | O | $C_2H_5$ | $C(CH_3)_2CH_2CO$ | $CH_3$ | 1-ethyl-β,β,4,4-tetramethyl//propionic acid |

TABLE I-continued

| | Starting Material of Formula II | | | | | | Ketoester of Formula VI $R^1-\overset{\overset{O}{\|}}{C}-Alk^1-COOR^{19}$ | | | Product: [(prefix listed below)-1,3,4,9-Tetrahydropyrano-[3,4-b]indole-1-(Suffix Listed Below) | |
|---|---|---|---|---|---|---|---|---|---|---|---|
| Example | $R^2$ | $R^3$ | $R^4$ | $R^5$ | $R^6$ | X | $R^1$ | $Alk^1$—CO | | $R^{19}$ | Prefix//Suffix |
| 43 | H | H | n-$C_3H_7$ | H | $\underset{4\text{-O}\overset{\|}{C}C_2H_5}{\overset{O}{\|}}$ | O |  | $C(C_2H_5)_2C(C_2H_5)CO$ | | $CH_3$ | 1-cyclopentyl-5-propionoxy-4-propyl-$\alpha,\beta,\beta$-triethyl//propionic acid |
| 44 | n-$C_3H_7$ | H | H | H | 4-$OCH_3$ | O | n-$C_3H_7$ | $CH_2CH(CH_3)CO$ | | $C_2H_5$ | 1,3-dipropyl-5-methoxy-$\alpha$-methyl//propionic acid |
| 45 | $C_2H_5$ | H | H | H | 5-$NO_2$ | O | $CH_3$ | $C(C_2H_5)_2C(C_2H_5)_2CO$ | | $C_2H_5$ | 1-methyl-6-nitro-$\alpha,\alpha,\beta,\beta$,3-pentaethyl//propionic acid |
| 46 | $C_2H_5$ | $C_2H_5$ | H | H | 4-$C_2H_5$ | O | n-$C_3H_7$ | $CH(n$-$C_3H_7)CH_2CO$ | | $CH_3$ | $\beta$,1-dipropyl-3,3,5-triethyl//propionic acid |
| 47 | H | H | H | H | 6-$OC_2H_5$ | O |  | $CH(C_2H_5)CH(C_2H_5)CO$ | | $C_2H_5$ | 1-cyclopropyl-$\alpha,\beta$-diethyl-7-ethoxy//propionic acid |
| 48 | H | H | H | H | H | O | $CH_3$ | $CH_2CH_2CH_2CO$ | | $C_2H_5$ | 1-methyl//butyric acid, m.p. 132 – 135° C. |
| 49 | $CH_3$ | H | H | H | H | O | $C_2H_5$ | $CH(CH_3)CH_2CH_2CO$ | | $C_2H_5$ | $\gamma$,3-dimethyl-1-ethyl//butyric acid |
| 50 | $CH_3$ | $CH_3$ | H | H | H | O | n-$C_3H_7$ | $C(C_2H_5)_2CH_2CH_2CO$ | | $C_2H_5$ | $\gamma,\gamma$-diethyl-3,3-dimethyl-1-propyl//butyric acid |
| 51 | $CH_3$ | $CH_3$ | n-$C_3H_7$ | H | H | O |  | $C(n$-$C_3H_7)_2CH(n$-$C_3H_7)CH_2CO$ | | $C_2H_5$ | 1-cyclobutyl-3,3-dimethyl-$\beta,\gamma,\gamma$,4-tetrapropyl//butyric acid |
| 52 | H | H | $C_2H_5$ | $C_2H_5$ | 6-Cl | O | $CH_3$ | $[C(C_2H_5)_2]_2\underset{H_5C_2}{\overset{-CCO}{\diagup}}\overset{}{\diagdown}H$ | | $C_2H_5$ | 7-chloro-$\alpha,\beta,\beta,\gamma,\gamma$,4,4-heptaethyl-1-methyl//butyric acid |
| 53 | H | H | $CH_3$ | H | 4-$CH_3$ | O | $C_2H_5$ | $[C(CH_3)_2]_3CO$ | | $C_2H_5$ | 1-ethyl-$\alpha,\alpha,\beta,\beta,\gamma,\gamma$,4,5-octamethyl//butyric acid |
| 54 | $C_2H_5$ | $C_2H_5$ | $C_2H_5$ | H | $\underset{5\text{-O}\overset{\|}{C}CH_3}{\overset{O}{\|}}$ | O | n-$C_3H_7$ | $CH(C_2H_5)[C(C_2H_5)]_2CO$ | | $C_2H_5$ | 6-acetoxy-$\alpha,\alpha,\beta,\beta,\gamma$,3,3,4-octaethyl-1-propyl//butyric acid |
| 55 | H | H | $CH_3$ | $CH_3$ | 7-$OCH_3$ | O |  | $CH_2[C(CH_3)_3]_2CO$ | | $C_2H_5$ | 1-cyclobutyl-$\alpha,\alpha,\beta,\beta$,4,4-hexamethyl-8-methoxy//butyric acid |
| 56 | H | H | H | H | 4-Br | O |  | $CH_2CH(CH_3)C(CH_3)_2CO$ | | $C_2H_5$ | 5-bromo-1-cyclopentyl-$\alpha,\alpha,\beta$-trimethyl//butyric acid |
| 57 | $CH_3$ | $CH_3$ | H | H | 4-n-$C_3H_7$ | O |  | $CH_2CH_2C(C_2H_5)_2CO$ | | $C_2H_5$ | 1-cyclopropyl-$\alpha,\alpha$-diethyl-3,3-dimethyl-5-propyl//butyric acid |
| 58 | H | H | H | H | 7-$C_2H_5$ | O | $C_2H_5$ | $CH_2CH_2CH(CH_3)CO$ | | $C_2H_5$ | 1,8-diethyl-$\alpha$-methyl//butyric acid |
| 59 | $CH_3$ | $CH_3$ | $CH_3$ | H | 5-F | O | n-$C_4H_9$ | $[CH(CH_3)]_3CO$ | | $C_2H_5$ | 1-butyl-6-fluoro-$\alpha,\beta,\gamma$,3,3,4-hexamethyl//butyric acid |
| 60 | $CH_3$ | $CH_3$ | H | H | 4-$CH_3$ | O | n-$C_3H_7$ | $CH(C_2H_5)CH_2CH(C_2H_5)CO$ | | $C_2H_5$ | $\alpha,\gamma$-diethyl-1-propyl-3,3,5-trimethyl//butyric acid |
| 61 | $C_2H_5$ | H | H | H | 6-$NO_2$ | O | n-$C_4H_9$ | $[C(CH_3)_2]_3CO$ | | $C_2H_5$ | 1-butyl-3-ethyl-7-nitro-$\alpha,\beta,\gamma$-trimethyl//butyric acid |
| 62 | $CH_3$ | $CH_3$ | H | H | 4-n-$C_3H_7$ | O | n-$C_3H_7$ | $CH_2[CH(C_2H_5)]_2CO$ | | $C_2H_5$ | $\alpha,\beta$-diethyl-3,3-dimethyl-1,5-dipropyl//butyric acid |
| 63 | H | H | H | H | 7-OH | O | $C_2H_5$ | $C(CH_3)_2CH_2C(CH_3)_2CO$ | | $C_2H_5$ | 1-ethyl-8-hydroxy-$\alpha,\alpha,\gamma,\gamma$-tetramethyl//butyric acid |
| 64 | $CH_3$ | H | $CH_3$ | H | 4-$OC_2H_5$ | O | $C_2H_5$ | $[C(CH_3)_2]_3CO$ | | $C_2H_5$ | 5-ethoxy-1-ethyl-$\alpha,\alpha,\beta,\beta,\gamma,\gamma$,3,4-octomethyl//butyric acid |

TABLE II

| | Starting Material of Formula II | | | | | | Ketoester of Formula VI $R^1-\overset{\overset{O}{\|}}{C}-Alk^1-COOR^{19}$ | | | Product: [(Prefix Listed Below)-1,3,4,9-Tetrahydrothiopyrano-[3,4-b]indole-1-(Suffix Listed Below)] | |
|---|---|---|---|---|---|---|---|---|---|---|---|
| Ex. | $R^2$ | $R^3$ | $R^4$ | $R^5$ | $R^6$ | X | $R^1$ | $Alk^1$—CO | | $R^{19}$ | Prefix//Suffix |
| 65 | H | H | H | H | H | S | $CH_3$ | CO | | $C_2H_5$ | 1-methyl//carboxylic acid |
| 66 | $CH_3$ | H | H | H | H | S | $C_2H_5$ | CO | | $C_2H_5$ | 1-ethyl-3-methyl//carboxylic acid |

TABLE II-continued

| | Starting Material of Formula II | | | | | | Ketoester of Formula VI $R^1-\overset{\overset{O}{\|}}{C}-Alk^1-COOR^{19}$ | | | Product: [(Prefix Listed Below)-1,3,4,9-Tetrahydrothiopyrano-[3,4-b]indole-1-(Suffix Listed Below)] |
|---|---|---|---|---|---|---|---|---|---|---|
| Ex. | $R^2$ | $R^3$ | $R^4$ | $R^5$ | $R^6$ | X | $R^1$ | $Alk^1-CO$ | $R^{19}$ | Prefix//Suffix |
| 67 | i-$C_3H_7$ | H | H | H | 5-$CH_3$ | S | i-$C_3H_7$ | CO | $CH_3$ | 1,3-diisopropyl-6-methyl//carboxylic acid |
| 68 | $CH_3$ | $CH_3$ | H | H | 5-OH | S | $CH_3$ | CO | $CH_3$ | 1,3,3-trimethyl-6-hydroxy-1-(1-propyl)//carboxylic acid |
| 69 | H | H | H | H | 7-$C_2H_5$ | S | n-$C_3H_7$ | CO | $CH_3$ | 8-ethyl-1-propyl//carboxylic acid |
| 70 | H | H | i-$C_3H_7$ | H | H | S | cyclopropyl | CO | $CH_3$ | 1-cyclopropyl-4-isopropyl//carboxylic acid |
| 71 | $CH_3$ | $CH_3$ | $C_2H_5$ | $C_2H_5$ | H | S | cyclopentyl | CO | $CH_3$ | 1-cyclopentyl-4,4-diethyl-3,3-dimethyl//carboxylic acid |
| 72 | H | H | $CH_3$ | H | H | S | $CH_3$ | $CH_2CO$ | $C_2H_5$ | 1,4-dimethyl//acetic acid |
| 73 | H | H | H | H | H | S | $C_2H_5$ | $CH_2CO$ | $C_2H_5$ | 1-ethyl//acetic acid, m.p. 138° C. |
| 74 | H | H | H | H | H | S | n-$C_3H_7$ | $CH_2CO$ | $C_2H_5$ | 1-propyl//acetic acid, m.p. 127 – 129° C. |
| 75 | H | H | H | H | H | S | i-$C_3H_7$ | $CH_2CO$ | $C_2H_5$ | 1-isopropyl//acetic acid |
| 76 | $CH_3$ | H | H | H | H | S | n-$C_3H_7$ | $CH_2CO$ | $C_2H_5$ | 3-methyl-1-propyl//acetic acid |
| 77 | $CH_3$ | H | $C_2H_5$ | $CH_3$ | H | S | $C_2H_5$ | $CH_2CO$ | $C_2H_5$ | 1,4-diethyl-3-methyl//acetic acid |
| 78 | H | H | H | H | H | S | $CH_3$ | $CH(CH_3)CO$ | $C_2H_5$ | α,1-dimethyl//acetic acid |
| 79 | H | H | H | H | H | S | cyclohexyl | $C(CH_3)_2CO$ | $C_2H_5$ | 1-cyclohexyl-α,α-dimethyl//acetic acid |
| 80 | H | H | H | H | H | S | t-$C_4H_9$ | $CH_2CO$ | $C_2H_5$ | 1-t-butyl//acetic acid |
| 81 | H | H | H | H | H | S | n-$C_4H_9$ | $CH_2CO$ | $C_2H_5$ | 1-butyl//acetic acid |
| 82 | H | H | H | H | 7-$CH_3$ | S | n-$C_3H_7$ | $CH_2CO$ | $C_2H_5$ | 8-methyl-1-propyl//acetic acid |
| 83 | H | H | H | H | 5-Br | S | n-$C_3H_7$ | $CH_2CO$ | $C_2H_5$ | 6-bromo-1-propyl//acetic acid |
| 84 | H | H | H | H | 5-$OCH_3$ | S | $CH_3$ | $CH_2CO$ | $CH_3$ | 6-methoxy-1-methyl//acetic acid |
| 85 | H | H | H | H | 5-$OCOCH_3$ | S | $CH_3$ | $CH_2CO$ | $C_2H_5$ | 6-acetoxy-1-methyl//acetic acid |
| 86 | H | H | H | H | 5-benzyloxy | S | $CH_3$ | $CH_2CO$ | $C_2H_5$ | 6-benzyloxy-1-methyl//acetic acid |
| 87 | H | H | H | H | 4-$CH_3$ | S | n-$C_3H_7$ | $CH_2CO$ | $C_2H_5$ | 5-methyl-1-propyl//acetic acid |
| 88 | H | H | H | H | 6-$CH_3$ | S | n-$C_3H_7$ | $CH_2CO$ | $C_2H_5$ | 7-methyl-1-propyl//acetic acid |
| 89 | H | H | H | H | 7-F | S | $CH_3$ | $C(C_2H_5)_2CO$ | $C_2H_5$ | α,α-diethyl-8-fluoro-1-methyl//acetic acid |
| 90 | $CH_3$ | $CH_3$ | H | H | 5-Cl | S | n-$C_3H_7$ | $CH(iC_3H_7)CO$ | $C_2H_5$ | 6-chloro-3,3-dimethyl-α-isopropyl-1-propyl//acetic acid |
| 91 | $CH_3$ | $CH_3$ | H | H | 5-$OC_2H_5$ | S | cyclopropyl | $CH(C_2H_5)CO$ | $C_2H_5$ | 1-cyclopropyl-α,α-diethyl-3,3-dimethyl-6-ethoxy//acetic acid |
| 92 | $CH_3$ | $CH_3$ | $C_2H_5$ | $C_2H_5$ | 6-$C_2H_5$ | S | cyclohexyl | $C(CH_3)_2CO$ | $C_2H_5$ | 1-cyclohexyl-α,α,3,3-tetramethyl-4,4,7-triethyl//acetic acid |
| 93 | $CH_3$ | H | n-$C_3H_7$ | n-$C_3H_7$ | 4-n-$C_3H_7$ | S | $C_2H_5$ | $CH(CH_3)CO$ | $C_2H_5$ | α,3-dimethyl-1-ethyl 4,4,5-tripropyl//acetic acid |
| 94 | H | H | H | H | H | S | n-$C_3H_7$ | $C(CH_3)_2CO$ | $C_2H_5$ | α,α-dimethyl-1-propyl//acetic acid |
| 95 | $C_2H_5$ | $C_2H_5$ | $C_2H_5$ | $C_2H_5$ | 4-$C_2H_5$ | S | t-$C_4H_9$ | $C(i-C_3H_7)_2CO$ | $C_2H_5$ | 1-t-butyl-α,α-diisopropyl-3,3,4,4-5-pentaethyl//acetic acid |
| 96 | H | H | H | H | H | S | $CH_3$ | $CH_2CH_2CO$ | $C_2H_5$ | 1-methyl//propionic acid |
| 97 | $CH_3$ | $CH_3$ | $CH_3$ | $CH_3$ | 7-$OCOCH_3$ | S | $C_2H_5$ | $CH_2CH(CH_3)CO$ | $C_2H_5$ | 8-acetoxy-1-ethyl-α,3,3,4,4-pentamethyl//propionic acid |
| 98 | H | H | H | H | 6-OH | S | n-$C_3H_7$ | $CH_2C(C_2H_5)_2CO$ | $C_2H_5$ | β,β-diethyl-7-hydroxy-1-propyl//propionic acid |

TABLE II-continued

| | Starting Material of Formula II | | | | | | Ketoester of Formula VI $R^1-\overset{O}{\overset{\|}{C}}-Alk^1-COOR^{19}$ | | Product: [(Prefix Listed Below)-1,3,4,9-Tetrahydrothiopyrano-[3,4-b]indole-1-(Suffix Listed Below)] |
|---|---|---|---|---|---|---|---|---|---|
| Ex. | $R^2$ | $R^3$ | $R^4$ | $R^5$ | $R^6$ | X | $R^1$ | $Alk^1-CO$ | $R^{19}$ Prefix//Suffix |
| 99 | $CH_3$ | H | H | H | 7-$NO_2$ | S | ☐ | $CH(n-C_3H_7)CH_2CO$ | $C_2H_5$ 1-cyclobutyl-3-methyl-8-nitro-$\alpha$-propyl//propionic acid |
| 100 | H | H | $CH_3$ | H | 5-$CH_3$ | S | △ | $C(CH_3)_2C(CH_3)_2CO$ | $C_2H_5$ 1,cyclopropyl-$\alpha,\alpha\beta\beta$ 4,6-hexamethyl//propionic acid |
| 101 | $CH_3$ | H | H | H | H | S | $CH_3$ | $CH_2C(n-C_3H_7)_2CO$ | $C_2H_5$ 1,3-dimethyl-$\alpha,\alpha$-dipropyl//propionic acid |
| 102 | $CH_3$ | H | $C_2H_5$ | $C_2H_5$ | H | S | $C_2H_5$ | $CH(CH_3)C(CH_3)_2CO$ | $CH_3$ 1,4,4-triethyl-$\alpha,\alpha,\beta$,-3-tetramethyl propionic acid |
| 103 | H | H | $CH_3$ | $CH_3$ | H | S | $C_2H_5$ | $C(CH_3)_2CH_2CO$ | $CH_3$ 1-ethyl-$\beta,\beta$,4,4-tetramethyl//propionic acid |
| 104 | H | H | n-$C_3H_7$ | H | 4-$OCC_2H_5$ (O) | S | ⬠ | $C(C_2H_5)_2C(C_2H_5)CO$ | $CH_3$ 1-cyclopentyl-5-propionoxy-4-propyl-$\alpha,\beta$, -triethyl//propionic acid |
| 105 | n-$C_3H_7$ | H | H | H | 4-$OCH_3$ | S | n-$C_3H_7$ | $CH_2CH(CH_3)CO$ | $C_2H_5$ 1,3-dipropyl-5-methoxy-$\alpha$-methyl//propionic acid |
| 106 | $C_2H_5$ | H | H | H | 5-$NO_2$ | S | $CH_3$ | $C(C_2H_5)_2C(C_2H_5)_2CO$ | $C_2H_5$ 1-methyl-6-nitro-$\alpha,\alpha,\beta,\beta$,3-pentaethyl//propionic acid |
| 107 | $C_2H_5$ | $C_2H_5$ | H | H | 4-$C_2H_5$ | S | n-$C_3H_7$ | $CH(n-C_3H_7)CH_2CO$ | $CH_3$ $\beta$,1-dipropyl-3,3,5-triethyl//propionic acid |
| 108 | H | H | H | H | 6-$OC_2H_5$ | S | ▷ | $CH(C_2H_5)CH(C_2H_5)CO$ | $C_2H_5$ 1-cyclopropyl-$\alpha,\beta$-diethyl-7-ethoxy//propionic acid |
| 109 | H | H | H | H | H | S | $CH_3$ | $CH_2CH_2CH_2CO$ | $C_2H_5$ 1-methyl//butyric acid |
| 110 | $CH_3$ | H | H | H | H | S | $C_2H_5$ | $CH(CH_3)CH_2CH_2CO$ | $C_2H_5$ $\gamma$,3-dimethyl-1-ethyl//butyric acid |
| 111 | $CH_3$ | $CH_3$ | H | H | H | S | n-$C_3H_7$ | $C(C_2H_5)_2CH_2CH_2CO$ | $C_2H_5$ $\gamma,\gamma$-diethyl-3,3-dimethyl-1-propyl//butyric acid |
| 112 | $CH_3$ | $CH_3$ | n-$C_3H_7$ | H | H | S | ☐ | $C(n-C_3H_7)_2CH(n-C_3H_7CH_2CO$ | $C_2H_5$ 1-cyclobutyl-3,3-dimethyl-$\beta,\gamma,\gamma$,4-tetrapropyl//butyric acid |
| 113 | H | H | $C_2H_5$ | $C_2H_5$ | 6-Cl | S | $CH_3$ | $[C(C_2H_5)_2]_2CH(C_2H_5)CO$ | $C_2H_5$ 7-chloro-$\alpha,\beta,\beta,\gamma,\gamma$,4,4-heptaethyl-1-methyl//butyric acid |
| 114 | H | H | $CH_3$ | H | 4-$CH_3$ | S | $C_2H_5$ | $[C(CH_3)_2]_3O$ | $C_2H_5$ 1-ethyl-$\alpha,\alpha,\beta,\beta,\gamma,\gamma$,4,5-octamethyl//butyric acid |
| 115 | $C_2H_5$ | $C_2H_5$ | $C_2H_5$ | H | 5-$OCCH_3$ (O) | S | n-$C_3H_7$ | $CH(C_2H_5)[C(C_2H_5)]_2CO$ | $C_2H_5$ 6-acetoxy-$\alpha,\alpha,\beta,\beta,\gamma$,3,3,4-octaethyl-propyl//butyric acid |
| 116 | H | H | $CH_3$ | $CH_3$ | 7-$OCH_3$ | S | ☐ | $CH_2[C(CH_3)_3]_2CO$ | $C_2H_5$ 1-cyclobutyl-$\alpha,\alpha,\beta$,$\beta$,4,4-hexamethyl-8-methoxy//butyric acid |
| 117 | H | H | H | H | 4-Br | S | ⬠ | $CH_2CH(CH_3)C(CH_3)_2CO$ | $C_2H_5$ 5-bromo-1-cyclopentyl $\alpha,\alpha,\beta$-trimethyl//butyric acid |
| 118 | $CH_3$ | $CH_3$ | H | H | 4-n-$C_3H_7$ | S | △ | $CH_2CH_2C(C_2H_5)_2CO$ | $C_2H_5$ 1-cyclopropyl-$\alpha,\alpha$,diethyl-3,3-dimethyl-5-propyl//butyric acid |
| 119 | H | H | H | H | 7-$C_2H_5$ | S | $C_2H_5$ | $CH_2CH_2CH(CH_3)CO$ | $C_2H_5$ 1,8-diethyl-$\alpha$-methyl//butyric acid |
| 120 | $CH_3$ | $CH_3$ | $CH_3$ | H | 5-F | S | n-$C_4H_9$ | $[CH(CH_3)]_3CO$ | $C_2H_5$ 1-butyl-6-fluoro-$\alpha,\beta,\gamma$,3,3,4-hexamethyl//butyric acid |
| 121 | $CH_3$ | $CH_3$ | H | H | 4-$CH_3$ | S | n-$C_3H_7$ | $CH(C_2H_5)CH_2CH(C_2H_5)CO$ | $C_2H_5$ $\alpha,\gamma$-diethyl-1-propyl-3,3,5-trimethyl butyric acid |
| 122 | $C_2H_5$ | H | H | H | 6-$NO_2$ | S | n-$C_4H_9$ | $[C(CH_3)_2]_3CO$ | $C_2H_5$ 1-butyl-3-ethyl-7-nitro-$\alpha,\beta,\gamma$-trimethyl//butyric acid |
| 123 | $CH_3$ | $CH_3$ | H | H | 4-n-$C_3H_7$ | S | n-$C_3H_7$ | $CH_2[CH(C_2H_5)]_2CO$ | $C_2H_5$ $\alpha,\beta$-diethyl-3,3-dimethyl-1,5-dipropyl//butyric acid |
| 124 | H | H | H | H | 7-OH | S | $C_2H_5$ | $C(CH_3)_2CH_2C(CH_3)_2CO$ | $C_2H_5$ 1-ethyl-8-hydroxy-$\alpha,\alpha,\gamma,\gamma$-tetramethyl//butyric acid |
| 125 | $CH_3$ | H | $CH_3$ | H | 4-$OC_2H_5$ | S | $C_2H_5$ | $[C(CH_3)_2]_3CO$ | $C_2H_5$ 5-ethoxy-1-ethyl-$\alpha,\alpha,\beta,\beta,\gamma,\gamma$,3,4-octomethyl//butyric |

TABLE II-continued

| | Starting Material of Formula II | | | | | | | Ketoester of Formula VI $R^1-\overset{\overset{O}{\|}}{C}-Alk^1-COOR^{19}$ | | Product: [(Prefix Listed Below)-1,3,4,9-Tetrahydrothiopyrano-[3,4-b]indole-1-(Suffix Listed Below)] |
|---|---|---|---|---|---|---|---|---|---|---|
| Ex. | $R^2$ | $R^3$ | $R^4$ | $R^5$ | $R^6$ | X | $R^1$ | $Alk^1-CO$ | $R^{19}$ | Prefix//Suffix |
| | | | | | | | | | | acid |

EXAMPLE 126

N,N,1-TRIMETHYL-1,3,4,9-TETRAHYDROPYRANO[3,4-b]INDOLE-1-ACETAMIDE[-VII; $R^1$ = $CH_3$, $R^2$, $R^3$, $R^4$, $R^5$, $R^6$ and $R^7$ = H, X = O AND Z = $CH_2CON(CH_3)_2$]

To a stirred solution of 1-methyl-1,3,4,9-tetrahydropyrano[3,4-b]indole-1-acetic acid (15 g, 0.061 mole), prepared as described in Example 1, in dry tetrahydrofuran (300 ml), cooled to −5° C., is added triethylamine (18.5 g, 0.183 mole), followed by ethyl chloroformate (16.6 g, 0.153 mole). The mixture is stirred at −5° C. for 2 hr. This mixture, which now contains the mixed anhydride of the above starting material, is added dropwise to a cooled 40% aqueous solution of the amine, dimethylamine (225 ml). The resulting mixture is stirred at room temperature for one-half hour. Most of the tetrahydrofuran is evaporated, and the residue partitioned between chloroform and water. The organic phase is washed with water, dried over sodium sulfate, and evaporated under reduced pressure. The residue is subjected to chromatography on silica gel. Elution with 20% ethyl acetate in benzene, followed by crystallization of the eluate from ethyl acetate affords the title compound, m.p. 149° - 151° C., $v_{max}^{CHCl_3}$ 3375, 1634 cm$^{-1}$.

In the same manner but replacing the 40% aqueous solution of dimethylamine with an equivalent amount of ammonium hydroxide (concentrated), methylamine (30% aqueous solution), n-hexylamine (20% aqueous solution), diethylamine (30% aqueous solution), isopropylamine (40% aqueous solution), ethylamine (70% aqueous solution), pyrrolidone (50% aqueous solution), piperidine, morpholine, N-methylpiperazine, 1-methyl-1,3,4,9-tetrahydropyran[3,4-b]indole-1-acetamide, m.p. 158° - 160° C.,
N,1-dimethyl-1,3,4,9-tetrahydropyrano[3,4-b]indole-1-acetamide, m.p. 138° - 140° C.,
N-hexyl-1-methyl-1,3,4,9-tetrahydropyrano[3,4-b]indole-1-acetamide,
N,N-diethyl-1-methyl-1,3,4,9-tetrahydropyrano[3,4-b]indole-1-acetamide, m.p. 99° C.,
N-isipropyl-1-methyl-1,3,4,9-tetrahydropyrano[3,4-b]indole-1-acetamide, m.p. 151° - 153° C.,
N-ethyl-1-methyl-1,3,4,9-tetrahydropyrano[3,4-b]indole-1-acetamide, m.p. 152° - 153° C.,
1-[(1-methyl-1,3,4,9-tetrahydropyrano[3,4-b]indol-1-yl)acetyl]pyrrolidine, m.p. 119° - 120° C.,
1-[(1-methyl-1,3,4,9-tetrahydropyrano[3,4-b]indole-1-yl)acetyl]piperidine, m.p. 148° - 149° C.,
1[(1-methyl-1,3,4,9-tetrahydropyrano[3,4-b]indol-1-yl)acetyl]morpholine, m.p. 141° - 142° C., and
1-methyl-4-[(1-methyl-1,3,4,9-tetrahydropyrano[3,4-b]indole-1-yl)acetyl]piperazine, are obtained respectively.

By following the procedure of Example 126 but using as starting material an equivalent amount of one of the acid compounds of formula VII, described in Examples 2 to 125, instead of 1-methyl-1,3,4,9-tetrahydropyrano[3,4-b]indole-1-acetic acid, and using an equivalent amount of an appropriate amine such as ammonia or a primary or secondary amine described in Example 126, then the corresponding amide compound of formula VII is obtained. Examples of such amides are listed as products in Tables III, IV, V and VI together with the appropriate starting material and amine used for the preparation of the amide. In each case the starting material is noted by the example in which it is prepared.

TABLE III

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 127 | 2 | $CH_3NH_2$ | N,1-dimethyl//propionamide, m.p. 149 - 150° C. |
| 128 | 2 | $NH_3$ | 1-methyl//propionamide |
| 129 | 2 | $(CH_3)_2NH$ | N,N,1-trimethyl//propionamide |
| 130 | 2 | n-$C_6H_{13}NH_2$ | N-hexyl-1-methyl//propionamide |
| 131 | 2 | $(C_2H_5)_2NH$ | N,N-diethyl-1-methyl//propionamide |
| 132 | 4 | $CH_3NH_2$ | N,1-dimethyl//carboxamide |
| 133 | 4 | $NH_3$ | 1-methyl//carboxamide, m.p. 188 - 189° C. |
| 134 | 4 | $(CH_3)_2NH$ | N,N,1-trimethyl//carboxamide |
| 135 | 4 | n-$C_6H_{13}NH_2$ | N-hexyl-1-methyl//carboxamide |
| 136 | 4 | $C_2H_5NH_2$ | N-ethyl-1-methyl//carboxamide |
| 137 | 5 | $CH_3NH_2$ | N,3-dimethyl-1-ethyl//carboxamide |
| 138 | 9 | $(CH_3)_2NH$ | 1-cyclopropyl-N,N-dimethyl-4-isopropyl//carboxamide |
| 139 | 11 | $(CH_3)_2NH$ | N,N,1,4-tetramethyl//acetamide |
| 140 | 12 | $CH_3NH_2$ | 1-ethyl-N-methyl//acetamide |
| 141 | 12 | $NH_3$ | 1-ethyl//acetamide |
| 142 | 12 | $(CH_3)_2NH$ | N,N-dimethyl-1-ethyl//acetamide |
| 143 | 12 | n-$C_{16}H_{13}NH_2$ | 1-ethyl-N-hexyl//acetamide |
| 144 | 12 | $(C_2H_5)_2NH$ | N,N,1-triethyl//acetamide |
| 145 | 13 | $CH_3NH_2$ | N-methyl-1-propyl//acetamide |
| 146 | 13 | $NH_3$ | 1-propyl//acetamide |
| 147 | 13 | $(CH_3)_2NH$ | N,N-dimethyl-1-propyl//acetamide, m.p. 159 - 162° C. |

TABLE III-continued

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 148 | 13 | n-C$_6$H$_{13}$NH$_2$ | N-hexyl-1-propyl//acetamide |
| 149 | 13 | (C$_2$H$_5$)$_2$NH | N,N-diethyl-1-propyl//acetamide |
| 150 | 14 | CH$_3$NH$_2$ | 1-isopropyl-N-methyl//acetamide |
| 151 | 14 | NH$_3$ | 1-isopropyl//acetamide |
| 152 | 14 | (C$_2$H$_5$)$_2$NH | N,N-diethyl-1-isopropyl//acetamide |
| 153 | 15 | CH$_3$NH$_2$ | N,3-dimethyl-1-propyl//acetamide |
| 154 | 15 | (CH$_3$)$_2$NH | 1-propyl-N,N,3-trimethyl//acetamide |
| 155 | 15 | n-C$_6$H$_{13}$NH$_2$ | n-hexyl-3-methyl-1-propyl//acetamide |
| 156 | 15 | (C$_2$H$_5$)$_2$NH | N,N-diethyl-3-methyl-1-propyl//acetamide |
| 157 | 17 | CH$_3$NH$_2$ | N,α,1-trimethyl//acetamide |
| 158 | 17 | NH$_3$ | α,1-dimethyl//acetamide |
| 159 | 17 | (CH$_3$)$_2$NH | N,N,α,1-tetramethyl//acetamide |
| 160 | 17 | n-C$_6$H$_{13}$NH$_2$ | α,1-dimethyl-N-hexyl//acetamide |
| 161 | 17 | (C$_2$H$_5$)$_2$NH | N,N-diethyl-α,1-dimethyl//acetamide |
| 162 | 18 | CH$_3$NH$_2$ | 1-cyclohexyl-N,α,α-trimethyl//acetamide |
| 163 | 21 | CH$_3$NH$_2$ | N,8-dimethyl-1-propyl//acetamide |
| 164 | 25 | NH$_2$ | 6-benzyloxy-1-methyl//acetamide |
| 165 | 26 | (CH$_3$)$_2$NH | 1-propyl-N,N,5-trimethyl//acetamide |
| 166 | 30 | n-C$_6$H$_{13}$NH$_2$ | 1-cyclopropyl-α,α-diethyl-3,3-dimethyl-6-ethoxy-N-hexyl//acetamide |
| 167 | 35 | CH$_3$NH$_2$ | 5-iodo-1-isopropyl-N-methyl//propionamide |
| 168 | 38 | NH$_2$ | 1-cyclobutyl-3-methyl-8-nitro-α-propyl//propionamide |
| 169 | 41 | (CH$_3$)$_2$NH | N,N,α,α,β,3-hexamethyl-1,4,4-triethyl//propionamide |
| 170 | 44 | (C$_2$H$_5$)$_2$NH | N,N-diethyl-1,3-dipropyl-5-methoxy-α-methyl//propionamide |
| 171 | 46 | CH$_3$NH$_2$ | N-methyl-β,1-dipropyl-3,3,5-triethyl//propionamide |
| 172 | 48 | (CH$_3$)$_2$NH | N,N,1-trimethyl//butyramide |
| 173 | 48 | CH$_3$NH$_2$ | N,1-dimethyl//butyramide |
| 174 | 48 | NH$_2$ | 1-methyl//butyramide |
| 175 | 48 | n-C$_6$H$_{13}$NH$_2$ | N-hexyl-1-methyl//butyramide |
| 176 | 51 | CH$_3$NH$_2$ | 1-cyclobutyl-β,γ,γ,4-tetrapropyl-N,3,3-trimethyl//butyramide |
| 177 | 53 | (CH$_3$)$_2$NH | N,N,α,α,β,β,γ,γ,4,5-decamethyl-1-ethyl//butyramide |
| 178 | 56 | NH$_2$ | 5-bromo-1-cyclopentyl-α,α,β-trimethyl//butyramide |
| 179 | 58 | CH$_3$NH$_2$ | 1,8-diethyl-N,α-dimethyl//butyramide |
| 180 | 60 | (C$_2$H$_5$)$_2$NH | 1-propyl-N,N,α,γ-tetraethyl-3,3,5-trimethyl//butyramide |
| 181 | 62 | n-C$_6$H$_{13}$NH$_2$ | α,β-diethyl-3,3-dimethyl-1,5-dipropyl-N-hexyl//butyramide |

TABLE IV

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 182 | 2 | pyrrolidine | 1-[(1-methyl//propionyl]pyrrolidine |
| 183 | 2 | piperidine | 1-[(1-methyl//propionyl]piperidine |
| 184 | 2 | morpholine | 4-[(1-methyl//propionyl]morpholine |
| 185 | 2 | piperazine | 1-[(1-methyl//propionyl]piperazine |
| 186 | 2 | N-methyl-piperazine | 1-methyl-4-[1-methyl//propionyl]-piperazine |
| 187 | 2 | N-piperazine-ethanol | 1-(2-hydroxyethyl)-4-[(1-methyl//propionyl]piperazine |
| 188 | 4 | pyrrolidine | 1-[(1-methyl//carbonyl]pyrrolidine |
| 189 | 4 | morpholine | 4-[(1-methyl//carbonyl]morpholine |
| 190 | 5 | N-ethyl-piperazine | 1-ethyl-4-[(1-ethyl-3-methyl//carbonyl]piperazine |
| 191 | 11 | piperidine | 1-[(1,4-dimethyl//acetyl]-piperidine |
| 192 | 12 | morpholine | 4-[(1-ethyl//acetyl]morpholine |
| 193 | 12 | N-piperazine-propanol | 1-(3-hydroxypropyl)-4-[(1-ethyl//acetyl]piperazine |
| 194 | 13 | pyrrolidine | 1-[(1-propyl//acetyl]pyrrolidine |
| 195 | 13 | morpholine | 4-[(1-propyl//acetyl]morpholine |
| 196 | 14 | piperidine | 1-[(1-isopropyl//acetyl]piperidine |
| 197 | 15 | piperazine | 1-[(3-methyl-1-propyl//acetyl]-piperazine |
| 198 | 17 | N-ethyl-piperazine | 1-ethyl-4-[(α,1-dimethyl//acetyl]-piperazine |
| 199 | 25 | pyrrolidine | 1-[(6-benzyloxyl-1-methyl//acetyl]-pyrrolidine |
| 200 | 26 | piperidine | 1-[(5-methyl-1-propyl//acetyl] |

TABLE IV-continued

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 201 | 30 | morpholine | 4-[(1-cyclopropyl-$\alpha,\alpha$-diethyl-3,3-dimethyl-6-ethoxy//acetyl]-morpholine |
| 202 | 36 | piperazine | 1-[8-acetoxy-1-ethyl-$\alpha$,3,3,4,4-pentamethyl//propionyl]piperazine |
| 203 | 39 | N-piperazine-ethanol | 1-(2-hydroxyethyl)-4-[(1-cyclopropyl-$\alpha,\alpha,\beta,\beta$,4,6-hexamethyl//propionyl]piperazine |
| 204 | 40 | pyrrolidine | 1-[(1,3-dimethyl-$\alpha,\alpha$-dipropyl//propionyl]pyrrolidine |
| 205 | 42 | morpholine | 4-[(1-ethyl-$\beta,\beta$,4,4-tetramethyl//propionyl]morpholine |
| 206 | 47 | N-propyl-piperazine | 1-propyl-4-[(1-cyclopropyl-$\alpha,\beta$-diethyl-6-ethoxy//propionyl]-piperazine |
| 207 | 48 | pyrrolidine | 1-[(1-methyl//butyryl]pyrrolidine |
| 207a | 48 | N-piperazine-methanol | 1-(hydroxymethyl)-4-[(1-methyl//butyryl]piperazine |
| 208 | 50 | piperidine | 1-[$\gamma,\gamma$-diethyl-3,3-dimethyl-1-propyl//butyryl]piperidine |
| 209 | 52 | morpholine | 4-[(7-chloro-$\alpha,\beta,\beta,\gamma,\gamma$,4,4-heptaethyl-1-methyl//butyryl]-morpholine |
| 210 | 59 | piperazine | 1-[(1-butyl-6-fluoro-$\alpha,\beta,\gamma$,3,3,4-hexamethyl//butyryl]piperazine |

TABLE V

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROTHIOPYRANO-[3,4-b]-INDOLE-1-(SUFFIX LISTED BELOW)] PREFIX//SUFFIX |
|---|---|---|---|
| 211 | 3 | $CH_3NH_2$ | N,1-dimethyl//acetamide |
| 212 | 3 | $NH_2$ | 1-methyl//acetamide |
| 213 | 3 | n-$C_6H_{13}NH_2$ | N-hexyl-1-methyl//acetamide |
| 214 | 3 | $(CH_3)_2NH$ | N,N,1-trimethyl//acetamide, m.p. 182° C. |
| 215 | 3 | $(C_2H_5)_2NH$ | N,N-diethyl-1-methyl//acetamide |
| 216 | 96 | $CH_3NH_2$ | N,1-dimethyl//propionamide |
| 217 | 96 | $NH_3$ | 1-methyl//propionamide |
| 218 | 96 | $(CH_3)_2NH$ | N,N,1-trimethyl//propionamide |
| 219 | 96 | n-$C_6H_{13}NH_2$ | N-hexyl-1-methyl//propionamide |
| 220 | 96 | $(C_2H_5)_2NH$ | N,N-diethyl-1-methyl//propionamide |
| 221 | 65 | $CH_3NH_2$ | N,1-dimethyl//carboxamide |
| 222 | 65 | $NH_3$ | 1-methyl//carboxamide |
| 223 | 65 | $(CH_3)_2NH$ | N,N,1-trimethyl//carboxamide |
| 224 | 65 | n-$C_6H_{13}NH_2$ | N-hexyl-1-methyl//carboxamide |
| 225 | 65 | $(C_2H_5)_2NH$ | N,N-diethyl-1-methyl//carboxamide |
| 226 | 66 | $CH_3NH_2$ | N,3-dimethyl-1-ethyl//carboxamide |
| 227 | 69 | $NH_3$ | 8-ethyl-1-propyl//carboxamide |
| 228 | 70 | $(CH_3)_2NH$ | 1-cyclopropyl-N,N-dimethyl-4-isopropyl//carboxamide |
| 229 | 72 | $(CH_3)_2NH$ | N,N,1,4-tetramethyl//acetamide |
| 230 | 73 | $CH_3NH_2$ | 1-ethyl-N-methyl//acetamide |
| 231 | 73 | $NH_3$ | 1-ethyl//acetamide |
| 232 | 73 | $(CH_3)_2NH$ | N,N-dimethyl-1-ethyl//acetamide |
| 233 | 73 | n-$C_{16}H_{13}NH_2$ | 1-ethyl-N-hexyl//acetamide |
| 234 | 73 | $(C_2H_5)_2NH$ | N,N,1-triethyl//acetamide |
| 235 | 74 | $CH_3NH_2$ | N-methyl-1-propyl//acetamide |
| 236 | 74 | $NH_3$ | 1-propyl//acetamide |
| 237 | 74 | $(CH_3)_2NH$ | N,N-dimethyl-1-propyl//acetamide |
| 238 | 74 | n-$C_6H_{13}NH_2$ | N-hexyl-1-propyl//acetamide |
| 239 | 74 | $(C_2H_5)_2NH$ | N,N-diethyl-1-propyl//acetamide |
| 240 | 75 | $CH_3NH_2$ | 1-isopropyl-N-methyl//acetamide |
| 241 | 75 | $NH_3$ | 1-isopropyl//acetamide |
| 242 | 75 | $(C_2H_5)_2NH$ | N,N-diethyl-1-isopropyl//acetamide |
| 243 | 76 | $CH_3NH_2$ | N,3-dimethyl-1-propyl//acetamide |
| 244 | 76 | $NH_3$ | 3,methyl-1-propyl//acetamide |
| 245 | 76 | $(CH_3)_2NH$ | 1-propyl,N,N,3-trimethyl//acetamide |
| 246 | 76 | n-$C_6H_{13}NH_2$ | N-hexyl-3-methyl-1-propyl//acetamide |
| 247 | 76 | $(C_2H_5)_2NH$ | N,N-diethyl-3-methyl-1-propyl//acetamide |
| 248 | 78 | $CH_3NH_2$ | N,$\alpha$,1-trimethyl//acetamide |
| 249 | 78 | $NH_3$ | $\alpha$,1-dimethyl//acetamide |
| 250 | 78 | $(CH_3)_2NH$ | N,N,$\alpha$,1-tetramethyl//acetamide |
| 251 | 78 | n-$C_6H_{13}NH_2$ | $\alpha$,1-dimethyl-N-hexyl//acetamide |
| 252 | 78 | $(C_2H_5)_2NH$ | N,N-diethyl-$\alpha$,1-dimethyl//acetamide |
| 253 | 79 | $CH_3NH_2$ | 1-cyclohexyl-N,$\alpha,\alpha$-trimethyl//acetamide |
| 254 | 82 | $CH_3NH_2$ | N,8-dimethyl-1-propyl//acetamide |
| 255 | 83 | $NH_2$ | 6-bromo-1-propyl//acetamide |

TABLE V-continued

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROTHIOPYRANO-[3,4-b]-INDOLE-1-(SUFFIX LISTED BELOW)] PREFIX//SUFFIX |
|---|---|---|---|
| 256 | 89 | $(CH_3)_2NH$ | $\alpha,\alpha$-diethyl-8-fluoro-N,N,1-trimethyl//acetamide |
| 257 | 91 | n-$C_6H_{13}NH_2$ | 1-cyclopropyl-$\alpha,\alpha$-diethyl-3,3-dimethyl-6-ethoxy-N-hexyl//acetamide |
| 258 | 99 | $NH_2$ | 1-cyclobutyl-3-methyl-8-nitro-$\alpha$-propyl//propionamide |
| 259 | 102 | $(CH_3)_2NH$ | N,N,$\alpha,\alpha,\beta$,3-hexamethyl-1,4,4-triethyl//propionamide |
| 260 | 105 | $(C_2H_5)_2NH$ | N,N-diethyl-1,3-dipropyl-5-methoxy-$\alpha$-methyl//propionamide |
| 261 | 107 | $CH_3NH_2$ | $\beta$,1-dipropyl-N-methyl-3,3,5-triethyl//propionamide |
| 262 | 108 | $CH_3NH_2$ | 1-cyclopropyl-$\alpha,\beta$-diethyl-6-ethoxy-N-methyl//propionamide |
| 263 | 109 | $(CH_3)_2NH$ | N,N,1-trimethyl//butyramide |
| 264 | 109 | $CH_3NH_2$ | N,1-dimethyl//butyramide |
| 265 | 109 | n-$C_6H_{13}NH_2$ | N-hexyl-1-methyl//butyramide |
| 266 | 112 | $CH_3NH_2$ | 1-cyclobutyl-$\beta,\gamma,\gamma$,4-tetrapropyl-N,3,3-trimethyl//butyramide |
| 267 | 113 | $(CH_3)_2NH$ | 7-chloro-$\alpha,\beta,\beta,\gamma,\gamma$,4,4-heptaethyl-N,N,1-trimethyl//butyramide |
| 268 | 117 | $NH_2$ | 5-bromo-1-cyclopentyl-$\alpha,\alpha,\beta$-trimethyl//butyramide |
| 269 | 119 | $CH_3NH_2$ | 1,8-diethyl-N,$\alpha$-dimethyl//butyramide |
| 270 | 121 | $(C_2H_5)_2NH$ | 1-propyl-N,N,$\alpha,\gamma$-tetraethyl-3,3,5-trimethyl//butyramide |
| 271 | 123 | n-$C_6H_{13}NH_2$ | $\alpha,\beta$-diethyl-3,3-dimethyl-1,5-dipropyl-N-hexyl//butyramide |

TABLE VI

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROTHIOPYRANO-[3,4-b]INDOLE-1-(SUFFIX LISTED BELOW] PREFIX//SUFFIX |
|---|---|---|---|
| 272 | 3 | pyrrolidine | 1-[(1-methyl//acetyl]pyrrolidine |
| 273 | 3 | piperidine | 1-[(1-methyl//acetyl]piperidine |
| 274 | 3 | morpholine | 4-[(1-methyl//acetyl]morpholine |
| 275 | 3 | piperazine | 1-[(1-methyl//acetyl]piperazine |
| 276 | 3 | N-methyl-piperazine | 1-methyl-4-[1-methyl//acetyl]-piperazine |
| 277 | 3 | N-piperazine-ethanol | 1-(2-hydroxyethyl)-4-[(1-methyl//acetyl]piperazine |
| 278 | 96 | pyrrolidine | 1-[(1-methyl//propionyl]-pyrrolidine |
| 279 | 96 | piperidine | 1-[(1-methyl//propionyl]piperidine |
| 280 | 96 | morpholine | 4-[(1-methyl//propionyl]morpholine |
| 281 | 96 | piperazine | 1-[(1-methyl//propionyl]piperazine |
| 282 | 96 | N-methyl-piperazine | 1-methyl-4-[1-methyl//propionyl]-piperazine |
| 283 | 96 | N-piperazine-ethanol | 1-(2-hydroxyethyl)-4-[(1-methyl//propionyl]piperazine |
| 284 | 65 | pyrrolidine | 1-[(1-methyl//carbonyl]pyrrolidine |
| 285 | 65 | morpholine | 4-[(1-methyl//carbonyl]morpholine |
| 286 | 66 | N-ethyl-piperazine | 1-ethyl-4-[(1-ethyl-3-methyl//carbonyl]piperzine |
| 287 | 72 | piperidine | 1-[(1,4-dimethyl//acetyl]-piperidine |
| 288 | 73 | morpholine | 4-[(1-ethyl//acetyl]morpholine |
| 289 | 73 | N-piperazine-propanol | 1-(3-hydroxypropyl)-4-[(1-ethyl//acetyl]piperazine |
| 290 | 74 | pyrrolidine | 1-[(1-propyl//acetyl]pyrrolidine |
| 291 | 74 | morpholine | 4-[(1-propyl//acetyl]morpholine |
| 292 | 75 | piperidine | 1-[(1-isopropyl//acetyl]piperidine |
| 293 | 76 | piperazine | 1-[(3-methyl-1-propyl//acetyl]-piperazine |
| 294 | 78 | N-ethyl-piperazine | 1-ethyl-4-[($\alpha$,1-dimethyl//acetyl]-piperazine |
| 295 | 86 | pyrrolidine | 1-[(6-benzyloxyl-1-methyl//acetyl]pyrrolidine |
| 296 | 87 | piperidine | 1-[(5-methyl-1-propyl//acetyl]-piperidine |
| 298 | 91 | morpholine | 4-[(1-cyclopropyl-$\alpha,\alpha$-diethyl-3,3-dimethyl-6-ethoxy//acetyl]-morpholine |
| 299 | 97 | piperazine | 1-[(8-acetoxy-1-ethyl-$\alpha$,3,3,4,4-pentamethyl//propionyl]piperazine |
| 300 | 100 | N-piperazine-ethanol | 1-(2-hydroxyethyl)-4-[(1-cyclopropyl-$\alpha,\alpha,\beta,\beta$,4,6-hexamethyl//propionyl]piperazine |
| 301 | 101 | pyrrolidine | 1-[(1,3-dimethyl-$\alpha,\alpha$-dipropyl//propionyl]pyrrolidine |
| 302 | 103 | morpholine | 4-[(1-ethyl-$\beta,\beta$,4,4-tetramethyl// |

TABLE VI-continued

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROTHIOPYRANO-[3,4-b]INDOLE-1-(SUFFIX LISTED BELOW] PREFIX//SUFFIX |
|---|---|---|---|
| 303 | 108 | N-propyl-piperazine | 1-propyl-4-[(1-cyclopropyl-α,β-diethyl-6-ethoxy//propionyl]-piperazine |
| 304 | 109 | pyrrolidine | 1-[(1-methyl//butyryl]pyrrolidine |
| 305 | 109 | N-piperazine-methanol | 1-(hydroxymethyl)-4-[(1-methyl//butyryl]piperazine |
| 306 | 111 | piperidine | 1-[(γ,γ,-diethyl-3,3-dimethyl-1-propyl//butyryl]piperidine |
| 307 | 113 | morpholine | 4-[(7-chloro-α,β,β,γ,γ,4,4-heptaethyl-1-methyl//butyryl]-morpholine |
| 308 | 120 | piperazine | 1-[(1-butyl-6-fluoro-α,β,γ,3,3,4-hexamethyl//butyryl]piperazine |

EXAMPLE 309

1-[2-(DIMETHYLAMINO)ETHYL]-1-METHYL-1,3,4,9-TETRAHYDROPYRANO[3,4-b]INDOLE [I; $R^1 = CH_3$, $R^2$, $R^3$, $R^4$, $R^5$, $R^6$, AND $R^7 = H$, $X = O$ $Y = CH_2CH_2N(CH_3)_2$]

A solution of N,N,1-trimethyl-1,3,4,9-tetrahydropyrano[3,4b]indole-1-acetamide (5.0 g, 0.018 mole), prepared as described in Example 126, is added dropwise to a cooled, well-stirred mixture of lithium aluminum hydride (1.4 g, 0.036 mole) in 200 ml of ether. Stirring is continued for one hour at room temperature, then the mixture is heated under reflux for 2 hr.

After cooling in an ice-water bath, 6.2 ml of water is added dropwise to destroy the excess hydride. Then 100 ml more of water is added and the ether phase decanted. The aqueous phase is extracted once with benzene. The combined organic phases are washed with water, dried over sodium sulfate, and evaporated to dryness to afford 5 g of oil which crystallized on standing. The crystallized product is recrystallized from ether to afford the pure title compound, m.p. 133° – 135° C., nmr(CDCl₃)δ 1.53 (s, 3H), 2.07 (2H), 9.74 (1H), 10.55 (6H).

The corresponding oxalic acid addition salt (oxalate), 1-[(2-dimethylamino)ethyl]-1-methyl-1,3,4,9-tetrahydropyrano[3,4-b]indole oxalate, has m.p. 181° – 183° C. after crystallization from methanol-ether.

In the same manner but replacing lithium aluminum hydride with an equivalent amount of lithium aluminum hydride-aluminum chloride, aluminum chloride-aluminum chloride, diborane and sodium borohydride-aluminum chloride, the title compound is also obtained.

In the same manner but replacing N,N,1-trimethyl-1,3,4,9-tetrahydropyrano[3,4-b]indole-1-acetamide with an equivalent amount of the following amides described in Example 126, 1-methyl-1,3,4,9-tetrahydropyrano[3,4-b]indole-1-acetamide,
N,1-dimethyl-1,3,4,9-tetrahydropyrano[3,4-b]indole-1-acetamide,
N-hexyl-1-methyl-1,3,4,9-tetrahydropyrano[3,4-b]indole-1-acetamide,
N,N-diethyl-1-methyl-1,3,4,9-tetrahydropyrano[3,4-b]indole-1-acetamide,
N-isopropyl-1-methyl-1,3,4,9-tetrahydropyrano[3,4-b]indole-1-acetamide,
N-ethyl-1-methyl-1,3,4,9-tetrahydropyrano[3,4-b]indole-1-acetamide,
1-[(1-methyl-1,3,4,9-tetrahydropyrano[3,4-b]indol-1-yl)acetyl]pyrrolidine,
1-[(1-methyl-1,3,4,9-tetrahydropyrano[3,4-b]indol-1-yl)acetyl]piperidine,
1-[(1-methyl-1,3,4,9-tetrahydropyrano[3,4-b]indol-1-yl)acetyl]morpholine, and
1-methyl-4-[(1-methyl-1,3,4,9-tetrahydropyrano[3,4-b]indol-1-yl)acetyl]piperazine, then there are obtained, 1-(2-aminoethyl)-1-methyl-1,3,4,9-tetrahydropyrano[3,4-b]indole, m.p. 80° – 84° C., $\nu_{max}^{CHCl_3}$ 3455, 3280cm⁻¹,
1-methyl-1-[2-(methylamino)ethyl]-1,3,4,9-tetrahydropyrano-[3,4-b]indole, m.p. 160° –163° C., (m.p. of corresponding oxalic acid addition salt, 140° – 144° C.),
1-[2-(hexylamino)ethyl]-1-methyl-1,3,4,9-tetrahydropyrano[3,4-b]indole,
1-[2-(diethylamino)ethyl]-1-methyl-1,3,4,9-tetrahydropyrano- [3,4-b]indole,
1-[2-(isopropylamino)ethyl]-1-methyl-1,3,4,9-tetrahydropyrano[3,4-b]indole,
1-[2-(ethylamino)ethyl]-1-methyl-1,3,4,9-tetrahydropyrano[3,4-b]indole,
1-methyl-1-[2-(1-pyrrolidinyl)ethyl]-1,3,4,9-tetrahydropyrano[3,4-b]indole,
nmr (CDCl₃) δ 1.62 (3H), 2.00 (m, 4H), 4.05 (m, 2H), m.p. of corresponding maleic acid addition salt (maleate), 192° – 192° C.
1-methyl-1-(2-piperidinoethyl)-1,3,4,9-tetrahydropyrano[3,4-b]indole, m.p. 146° – 148° C., m.p. of corresponding maleic acid addition salt, 147° – 149° C.,
1-methyl-1-(2-morpholinoethyl)-1,3,4,9-tetrahydropyrano[3,4-b]indole, nmr (DMSO-d₅) δ 1.50 (3H), 6.07 (2H), 6.87 – 7.65 (m, 4H), 10.86 (1H), m.p. of corresponding maleic acid addition salt, 192° – 193° C., and
1-methyl-1-[2-(4-methyl-1-piperazinyl)ethyl]-1,3,4,9-tetrahydropyrano[3,4-b]indole, nmr (CDCl₃) δ 1.47 (3H), 2.58 (3H), 3.87 (t, 2H), [m.p. of corresponding maleic acid addition salt (i.e. dimaleate), 208° – 210° C.], respectively.

By following the procedure of Example 309 but using as starting material an equivalent amount of one of the amide compounds of formula VII, described in Examples 127 to 308 instead of N,N,1-trimethyl-1,3,4,9-tetrahydropyrano[3,4-b]indole-1-acetamide, then the corresponding compounds of formula I in which $R^7$ is hydrogen are obtained. Examples of such compounds of formula I are listed as products in Tables VII and VIII together with the appropriate starting material, amides of formula VII. In each case the starting material is noted by the example in which it is prepared.

TABLE VII

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]-INDOLE |
|---|---|---|
| 310 | 127 | 1-methyl-1-[3-(methylamino)propyl], nmr (CDCl$_3$) δ1.48 (3H), 1.87 (4H), 2.47 (3H), corresponding oxalic acid addition salt has m.p. 110° C. |
| 311 | 128 | 1-(3-aminopropyl)-1-methyl |
| 312 | 129 | 1-methyl-1-[3-(dimethylamino)-propyl], m.p. 114 – 116° C., corresponding oxalic acid addition salt has m.p. 168 – 172° C. |
| 313 | 130 | 1-[3-(hexylamino)propyl]-1-methyl |
| 314 | 131 | 1-[3-(diethylamino)propyl]-1-methyl |
| 315 | 132 | 1-methyl-1-[(methylamino)methyl] CHCl$_3$ |
| 316 | 133 | 1-(aminomethyl)-1-methyl, δ max 3465, 3400, 3180, 2930, corresponding hydrochloric acid addition salt (hydrochloride) has m.p. 251 – 252° C. |
| 317 | 134 | 1-[(dimethylamino)methyl]-1-methyl |
| 318 | 135 | 1-[(hexylamino)methyl]-1-methyl |
| 319 | 136 | 1-[(ethylamino)methyl]-1-methyl, nmr (DMSO-d$_6$) δ1.18 (3H), 1.62 (3H), 2.80 (2H); corresponding hydrochloric acid addition salt has m.p. 242 – 243° C. |
| 320 | 137 | 1-ethyl-3-methyl-1-[(methylamino)methyl] |
| 321 | 138 | 1-cyclopropyl-1-[(dimethylamino)methyl]-4-isopropyl |
| 322 | 139 | 1,4-dimethyl-1-[2-(dimethylamino)ethyl] |
| 323 | 140 | 1-ethyl-1-[2-(methylamino)ethyl] |
| 324 | 141 | 1-(2-aminoethyl)-1-ethyl |
| 325 | 142 | 1-[2-(dimethylamino)ethyl]-1-ethyl |
| 326 | 143 | 1-ethyl-1-[2-(hexylamino)ethyl] |
| 327 | 144 | 1-[2-(diethylamino)ethyl]-1-ethyl |
| 328 | 145 | 1-[2-(methylamino)ethyl]-1-propyl |
| 329 | 146 | 1-(aminoethyl)-1-propyl |
| 330 | 147 | 1-[2-(dimethylamino)ethyl]-1-propyl, nmr (CDCl$_3$) 0.84 (t,3H), 1.21 (3, 6H), 2.79 (t, 5 = 5.5 cps, 2H) corresponding maleic acid addition salt has m.p. 152 – 154° C) |
| 331 | 148 | 1-[2-(hexylamino)ethyl]-1-propyl |
| 332 | 149 | 1-[2-(diethylamino)ethyl]-1-propyl |
| 333 | 150 | 1-isopropyl-1-[2-(methylamino)ethyl] |
| 334 | 151 | 1-(2-aminoethyl)-1-isopropyl |
| 335 | 152 | 1-[2-(diethylamino)ethyl-1-isopropyl |
| 336 | 153 | 3-methyl-1-[2-(methylamino)ethyl]-1-propyl |
| 337 | 154 | 1-[2-(dimethylamino)ethyl]-3-methyl-1-propyl |
| 338 | 155 | 1-[2-(hexylamino)ethyl]-3-methyl-1-propyl |
| 339 | 156 | 1-[2-(diethylamino)ethyl]-3-methyl-1-propyl |
| 340 | 157 | 1-[1-methyl-2-(methylamino)ethyl]-1-methyl |
| 341 | 158 | 1-(2-amino-1-methyl-ethyl)-1-methyl |
| 342 | 159 | 1-[2-(dimethylamino)-1-methyl-ethyl]-1-methyl |
| 343 | 160 | 1-[2-(hexylamino)-1-methyl-ethyl]-1-methyl |
| 344 | 161 | 1-[2-(diethylamino)-1-methyl-ethyl]-1-methyl |
| 345 | 162 | 1-cyclohexyl-1-[1,1-dimethyl-2-(methylamino)ethyl] |
| 346 | 163 | 8-methyl-1-[2-(methylamino)ethyl]-1-propyl |
| 347 | 164 | 1-(2-aminoethyl)-6-benzyloxy-1-methyl |
| 348 | 165 | 1-[2-(dimethylamino)ethyl]-5-methyl-1-propyl |
| 349 | 166 | 1-cyclopropyl-1-[1,1-diethyl-2-(hexylamino)ethyl]-3,3-dimethyl-6-ethoxy |
| 350 | 167 | 5-iodo-1-isopropyl-1-[3-(methyl- |

TABLE VII-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]-INDOLE |
|---|---|---|
| 351 | 168 | amino)propyl]<br>1-(3-amino-2-propyl-propyl)-1-cyclobutyl-3-methyl-8-nitro |
| 352 | 169 | 1-[3-(dimethylamino)-1,2,2-trimethyl-propyl]-1,4,4-triethyl |
| 353 | 170 | 1-[3-(diethylamino)-2-methyl-propyl]-1,3-dipropyl-5-methoxy |
| 354 | 171 | 1-[1-propyl-3-(methylamino)-propyl]-1-propyl-3,3,5-trimethyl |
| 355 | 172 | 1-[4-(dimethylamino)butyl]-1-methyl |
| 356 | 173 | 1-[4-(methylamino)butyl]-1-methyl |
| 357 | 174 | 1-(4-aminobutyl)-1-methyl |
| 358 | 175 | 1-[4-(hexylamino)butyl]-1-methyl |
| 359 | 176 | 1-cyclobutyl-3,3-dimethyl-1-[4-(methylamino)-1,1,2-tripropyl-butyl]-4-propyl |
| 360 | 177 | 4,5-dimethyl-1-ethyl-1-[4-dimethylamino)-1,1,2,2,3,3-hexamethylbutyl] |
| 361 | 178 | 1-(4-amino-2,3,3-trimethyl-butyl)-5-bromo-1-cyclopentyl |
| 362 | 179 | 1,8-diethyl-1-[3-methyl-4-(methylamino)butyl] |
| 363 | 180 | 1-[1,3-diethyl-4-(diethylamino)-butyl]-1-propyl-3,3,5-trimethyl |
| 364 | 181 | 1-[2,3-diethyl-4-(hexylamino)-butyl]-3,3-dimethyl-1,5-dipropyl |
| 365 | 182 | 1-methyl-1-[3-(1-pyrrolidinyl)-propyl], m.p. 124 – 127° C. |
| 366 | 183 | 1-methyl-1-(3-piperidinopropyl) |
| 367 | 184 | 1-methyl-1-(3-morpholinopropyl) |
| 368 | 185 | 1-methyl-1-(3-piperazinopropyl) |
| 369 | 186 | 1-methyl-1-[3-(4-methyl-1-piperazinyl)propyl] |
| 370 | 187 | 1-{3-[4-(2-hydroxyethyl)-1-piperazinyl]propyl}-1-methyl |
| 371 | 188 | 1-methyl-1-[(1-pyrrolidinyl)-methyl] |
| 372 | 189 | 1-methyl-1-(morpholinomethyl) |
| 373 | 190 | 1-ethyl-3-methyl-1-[(4-methyl-1-piperazinyl)methyl] |
| 374 | 191 | 1,4-dimethyl-1-(2-piperidinoethyl) |
| 375 | 192 | 1-ethyl-1-(2-morpholinoethyl) |
| 376 | 193 | 1-ethyl-1-{2-[4-(3-hydroxypropyl)-1-piperazinyl]ethyl} |
| 377 | 194 | 1-propyl-1-[2-(1-pyrrolidinyl)-ethyl] |
| 378 | 195 | 1-propyl-1-(2-morpholinoethyl) |
| 379 | 196 | 1-isopropyl-1-(2-piperidinoethyl) |
| 380 | 197 | 3-methyl-1-(2-piperazinoethyl)-1-propyl |
| 381 | 198 | 1-ethyl-1-[1-methyl-2-(4-methyl-1-piperazinyl)ethyl] |
| 382 | 199 | 6-benzyloxy-1-methyl-1-[2-(1-pyrrolidinyl)ethyl] |
| 383 | 200 | 5-methyl-1-(2-piperidinoethyl)-1-propyl |
| 384 | 201 | 1-cyclopropyl-1-(1,1-diethyl-2-morpholinoethyl)-3,3-dimethyl-6-ethoxy |
| 385 | 202 | 8-acetoxy-1-ethyl-3,3,4,4-tetramethyl-1-(2-methyl-3-piperazinopropyl) |
| 386 | 203 | 1-cyclopropyl-4,6-dimethyl-1-{3-[4-(2-hydroxyethyl)-1-piperazinyl]-1,1,2,2-tetramethylpropyl} |
| 387 | 204 | 1,3-dimethyl-1-[2,2-dipropyl-3-(1-pyrrolidinyl)propyl] |
| 388 | 205 | 4,4-dimethyl-1-ethyl-1-(1,1-dimethyl-3-morpholinopropyl) |
| 389 | 206 | 1-cyclopropyl-1-[1,2-diethyl-3-(4-propyl-1-piperazinyl)propyl]-6-ethoxy |
| 390 | 207 | 1-methyl-1-[4-(1-pyrrolidinyl)-butyl] |
| 391 | 207a | 1-{4-[4-(hydroxymethyl)-1-piperazinyl]butyl}-1-methyl |
| 392 | 208 | 1-[(1,1-diethyl-4-piperidino)butyl]-3,3-dimethyl-1-propyl |
| 393 | 209 | 7-chloro-4,4-diethyl-1-methyl-1-(4-morpholino-1,1,2,2,3-pentaethylbutyl) |
| 394 | 210 | 1-butyl-6-fluoro-1-(4-piperazino-1,2,3-trimethylbutyl)-3,3,4-trimethyl |

TABLE VIII

| EXAMPLE | NO. OF THE EXAMPLES IN WHICH STARTING MATERIAL IS PREPARED | PRODUCT: (PREFIX LISTED BELOW)-1,3,4,9-TETRAHYDROTHIOPYRANO-[3,4-b]INDOLE |
|---|---|---|
| 395 | 211 | 1-methyl-1-[2-(methylamino)ethyl] |
| 396 | 212 | 1-(2-aminoethyl)-1-methyl |
| 397 | 213 | 1-[(2-hexylamino)ethyl]-1-methyl |
| 398 | 214 | 1-[2-(dimethylamino)ethyl]-1-methyl, m.p. 119 – 121° C. |
| 399 | 215 | 1-[2-(diethylamino)ethyl]-1-methyl |
| 400 | 216 | 1-methyl-1-[3-(methylamino)propyl] |
| 401 | 217 | 1-(3-aminopropyl)-1-methyl |
| 402 | 218 | 1-[3-(dimethylamino)propyl]-1-methyl |
| 403 | 219 | 1-[3-(hexylamino)propyl]-1-methyl |
| 404 | 220 | 1-[3-(diethylamino)propyl]-1-methyl |
| 405 | 221 | 1-methyl-1-[(methylamino)methyl] |
| 406 | 222 | 1-(aminomethyl)-1-methyl |
| 407 | 223 | 1-[(dimethylamino)methyl[-1-methyl |
| 408 | 224 | 1-[(hexylamino)methyl]-1-methyl |
| 409 | 225 | 1-[(diethylamino)methyl]-1-methyl |
| 410 | 226 | 1-ethyl-3-methyl-1-[(methylamino)methyl] |
| 411 | 228 | 1-cyclopropyl-1-[(dimethylamino)methyl)-4-isopropyl |
| 412 | 229 | 1,4-dimethyl-1-[2-dimethylamino)-ethyl] |
| 413 | 230 | 1-ethyl-1-[2-(methylamino)ethyl) |
| 414 | 231 | 1-(2-aminoethyl)-1-ethyl |
| 415 | 232 | 1-[2-(dimethylamino)ethyl]-1-ethyl |
| 416 | 233 | 1-ethyl-1-[2-(hexylamino)ethyl] |
| 417 | 234 | 1-[2-diethylamino)ethyl]-1-ethyl |
| 418 | 235 | 1-[2-(methylamino)ethyl]-1-propyl |
| 419 | 236 | 1-(aminoethyl)-1-propyl |
| 420 | 237 | 1-[2-(dimethylamino)ethyl]-1-propyl |
| 421 | 238 | 1-[2-(hexylamino)ethyl]-1-propyl |
| 422 | 239 | 1-[2-(diethylamino)ethyl]-1-propyl |
| 423 | 240 | 1-isopropyl-1-[2-(methylamino)-ethyl] |
| 424 | 241 | 1-(2-aminoethyl)-1-isopropyl |
| 425 | 242 | 1-[2-(diethylamino)ethyl)-1-isopropyl |
| 426 | 243 | 3-methyl-1-[2-(methylamino)ethyl]-1-propyl |
| 427 | 245 | 1-[2-(dimethylamino)ethyl]-3-methyl-1-propyl |
| 428 | 246 | 1-[2-(hexylamino)ethyl]-3-methyl-1-propyl |
| 429 | 247 | 1-[2-(diethylamino)ethyl]-3-methyl-1-propyl |
| 430 | 248 | 1-[1-methyl-2-(methylamino)ethyl]-1-methyl |
| 431 | 249 | 1-(2-amino-1-methylethyl)-1-methyl |
| 432 | 250 | 1-[2-(dimethylamino)-1-methyl-ethyl]-1-methyl |
| 433 | 251 | 1-[2-(hexylamino)-1-methyl-ethyl]-1-methyl |
| 434 | 252 | 1-[2-(diethylamino)-1-methyl-ethyl]-1-methyl |
| 435 | 253 | 1-cyclohexyl-1-[1,1-dimethyl-2-(methylamino)ethyl] |
| 436 | 254 | 8-methyl-1-[2-(methylamino)ethyl]-1-propyl |
| 437 | 255 | 1-(2-aminoethyl)-6-bromo-1-propyl |
| 438 | 257 | 1-cyclopropyl-1-[1,1-diethyl-2-(hexylamino)ethyl]-3,3-dimethyl-6-ethoxy |
| 439 | 258 | 1-(3-amino-2-propyl-propyl)-1-cyclobutyl-3-methyl-8-nitro |
| 440 | 259 | 1-[3-(dimethylamino)-1,2,2-trimethyl-propyl]-1,4,4-triethyl |
| 441 | 260 | 1-[3-(diethylamino)-2-methyl-propyl]-1,3-dipropyl-5-methoxy |
| 442 | 261 | 1-[1-propyl-3-(methylamino)-propyl]-1-propyl-3,3,5-trimethyl |
| 443 | 263 | 1-[4-(dimethylamino)butyl]-1-methyl |
| 444 | 264 | 1-[4-(methylamino)butyl]-1-methyl |
| 445 | 265 | 1-[4-(hexylamino)butyl]-1-methyl |
| 446 | 266 | 1-cyclobutyl-3,3-dimethyl-1-[4-(methylamino)-1,1,2-tripropyl-butyl]-4-propyl |
| 447 | 267 | 7-chloro-4,4-diethyl-1-[4-dimethylamino-1,1,2,2,3-pentaethylbutyl]-1-methyl |
| 448 | 268 | 1-(4-amino-2,3,3-trimethyl-butyl)-5-bromo-1-cyclopentyl |

TABLE VIII-continued

| EXAMPLE | NO. OF THE EXAMPLES IN WHICH STARTING MATERIAL IS PREPARED | PRODUCT: (PREFIX LISTED BELOW)-1,3,4,9-TETRAHYDROTHIOPYRANO-[3,4-b]INDOLE |
|---|---|---|
| 449 | 269 | 1,8-diethyl-1-[3-methyl-4-(methylamino)butyl] |
| 450 | 270 | 1-[1,3-diethyl-4-(diethylamino)-butyl]-1-propyl-3,3,5-trimethyl |
| 451 | 271 | 1-[2,3-diethyl-4-(hexylamino)-butyl]-3,3-dimethyl-1,5-dipropyl |
| 452 | 272 | 1-methyl-1-[2-(1-pyrrolidinyl)-ethyl] |
| 453 | 273 | 1-methyl-1-(2-piperidinoethyl) |
| 454 | 274 | 1-methyl-1-(2-morpholinoethyl) |
| 455 | 275 | 1-methyl-1-(2-piperazinoethyl) |
| 456 | 276 | 1-methyl-1-[2-(4-methyl-1-piperazinyl)ethyl] |
| 457 | 277 | 1-{2-[4-(2-hydroxyethyl)-1-piperazinyl]ethyl}-1-methyl |
| 458 | 278 | 1-methyl-1-[3-(1-pyrrolidinyl)-propyl] |
| 459 | 279 | 1-methyl-1-(3-piperidinopropyl) |
| 460 | 280 | 1-methyl-1-(3-morpholinopropyl) |
| 461 | 281 | 1-methyl-1-(3-piperazinopropyl) |
| 462 | 282 | 1-methyl-1-[3-(4-methyl-1-piperazinyl)propyl] |
| 463 | 283 | 1-{3-[4-(2-hydroxyethyl)-1-piperazinyl]propyl}-1-methyl |
| 464 | 284 | 1-methyl-1-[(1-pyrrolidinyl)-methyl] |
| 465 | 285 | 1-methyl-1-(morpholinomethyl) |
| 466 | 286 | 1-ethyl-3-methyl-1-[(4-ethyl-1-piperazinyl)methyl] |
| 467 | 287 | 1,4-dimethyl-1-(2-piperidinoethyl) |
| 468 | 288 | 1-ethyl-1-(2-morpholinoethyl) |
| 469 | 289 | 1-ethyl-1-{2-[4-(3-hydroxypropyl)-1-piperazinyl]ethyl} |
| 470 | 290 | 1-propyl-1-[2-(1-pyrrolidinyl)-ethyl] |
| 471 | 291 | 1-(2-morpholinoethyl)-1-propyl |
| 472 | 292 | 1-isopropyl-1-(2-piperidinoethyl) |
| 473 | 293 | 3-methyl-1-(2-piperazinoethyl)-1-propyl |
| 474 | 295 | 1-methyl-1-[1-methyl-2-(4-methyl-1-piperazinyl)ethyl] |
| 475 | 296 | 6-benzyloxy-1-methyl-1-[2-(1-pyrrolidinyl)ethyl] |
| 476 | 297 | 5-methyl-1-(2-piperidinoethyl)-1-propyl |
| 477 | 298 | 1-cyclopropyl-1-(1,1-diethyl-2-morpholinethyl)-3,3-dimethyl-6-ethoxy |
| 478 | 299 | 8-acetoxy-1-ethyl-3,3,4,4-tetramethyl-1-(2-methyl-3-piperazinopropyl) |
| 479 | 300 | 1-cyclopropyl-4,6-dimethyl-1-{3-[4-(2-hydroxyethyl)-1-piperazinyl]-1,1,2,2-tetramethylpropyl} |
| 480 | 301 | 1,3-dimethyl-1-[2,2-dipropyl-3-(1-pyrrolidinyl)propyl] |
| 481 | 302 | 4,4-dimethyl-1-ethyl-1-(1,1-dimethyl-3-morpholinopropyl) |
| 482 | 303 | 1-cyclopropyl-6-ethoxy-1-[1,2-diethyl-3-(4-propyl-1-piperazinyl)propyl |
| 483 | 304 | 1-methyl-1-[4-(1-pyrrolidinyl)-butyl] |
| 484 | 305 | 1-{4-[4-(hydroxymethyl)-piperazinyl]butyl}-1-methyl |
| 485 | 306 | 1-[(1,1-diethyl-4-piperidino)-butyl]-3,3-dimethyl-1-propyl |
| 486 | 307 | 7-chloro-4,4-diethyl-1-methyl-1-(4-morpholino-1,1,2,2,3-pentaethylbutyl) |
| 487 | 308 | 1-butyl-6-fluoro-1-(4-piperazino-1,2,3-trimethylbutyl)-3,3,4-trimethyl |

EXAMPLE 488

1,9-DIMETHYL-1,3,4,9-TETRAHYDROPYRANO[3,4-b]INDOLE-1-ACETIC ACID (VII; $R^1$ and $R^7$ = $CH_3$, $R^2$, $R^3$, $R^4$, $R^5$ AND $R^6$ = H, X = O AND Z = $CH_2COOH$ 1-Methyl-1,3,4,9-tetrahydropyrano[3,4-b]indole-1-acetic acid (10 g., 0.04 mole), prepared as described in Example 1, in 150 ml. of tetrahydrofuran is added dropwise to a stirred suspension of sodium hydride (4.4 g. of 55% dispersion) in 200 ml. of tetrahydrofuran. This mixture is heated at 50° C. with stirring for 2 hr. Methyl iodide (14.2 g. 0.1 mole) is added dropwise and heating and stirring is continued for a further 2 hr.

After cooling, water is added until the solution is clear. The tetrahydrofuran is evaporated off under reduced pressure, the residue is partitioned between water and benzene. The aqueous phase is washed once with benzene, made acidic with HCl, and extracted with benzene (3x). The organic phase is washed with water, dried over sodium sulfate and treated with charcoal. The organic layer is evaporated. The residue is crystallized from benzene and then ether-petroleum ether to afford the title compound, m.p. 105° – 108° C., nmr (CDCl$_3$) δ 1.73 (S, 3H), 2.83 (t, J = 5.5, 2H), 3.0 (2H), 3.68 (3H), 4.08 (t, J = 5.5, 2H), 7.34 (4H), 9.47 (1H).

The the same manner but replacing methyl iodide with an equivalent amount of ethyl iodide, or propyl iodide, the N-ethyl analog of the title compound, 9-ethyl-1-methyl-1,3,4,9-tetrahydropyrano[3,4-b]indole-1-acetic acid, m.p. 134° – 136° C., and the N-propyl analog of the title compound, 1-methyl-9-propyl-1,3,4,9-tetrahydropyrano[3,4-b]indole-1-acetic acid, m.p. 120° – 122° C., are obtained, respectively.

By following the procedure of Example 488 but using as starting material an equivalent amount of the acid compounds of formula VII, in which R$^7$ is hydrogen, described in Examples 1 to 125, inclusive, instead of 1-methyl-1,3,4,9-tetrahydropyrano[3,4-b]indole-1-acetic acid, and using an equivalent amount of an appropriate organic halide, then the corresponding N-alkylated acid compounds of formula I are obtained. Examples of these latter compounds are listed as products in Tables IX and X together with the appropriate starting material of formula VII and organic halide used for their preparation. In each case the starting material is noted by the Example in which it is prepared.

TABLE IX

| EXAMPLE | NO. OF THE EXAMPLE IN WHICH STARTING MATERIAL IS PREPARED | ORGANIC HALIDE | PRODUCT: [(PREFIX LISTED BELOW)-1,3,4,9-TETRAHYDROPYRANO[3,4-b]-INDOLE-(SUFFIX LISTED BELOW)] PREFIX//SUFFIX |
|---|---|---|---|
| 489 | 1 | CH$_2$=CHCH$_2$Br | 9-allyl-1-methyl//acetic acid, m.p. 103 – 105° C. |
| 490 | 1 | CH$_2$=CHBr | 1-methyl-9-vinyl//acetic acid |
| 491 | 1 | CH≡CCH$_2$Br | 1-methyl-9-propargyl//acetic acid |
| 492 | 2 | n-C$_3$H$_7$I | 1-methyl-9-propyl//propionic acid |
| 493 | 2 | CH$_3$I | 1,9-dimethyl//propionic acid |
| 494 | 2 | ⌬-CH$_2$CH$_2$Br | 1-methyl-9-phenethyl//propionic acid |
| 495 | 2 | 1-(3-chloropropyl)-piperazine | 1-methyl-9-(3-piperidinopropyl)//propionic acid |
| 496 | 4 | 1-(2-chloroethyl)-pyrrolidine | 1-methyl-9-[2-(1-pyrrolidinyl)-ethyl//carboxylic acid |
| 497 | 6 | CH≡CCH$_2$Br | 1,3-diisopropyl-6-methyl-9-propargyl//carboxylic acid |
| 498 | 7 | CH$_3$I | 6-hydroxy-1,3,3,9-tetramethyl//carboxylic acid |
| 499 | 8 | CH$_3$CH=CHBr | 8-ethyl-9-(1-propenyl)-1-propyl//carboxylic acid |
| 500 | 10 | C$_2$H$_5$Br | 1-cyclopentyl-4,4,9-triethyl-3,3-dimethyl//carboxylic acid |
| 501 | 12 | CH$_3$I | 1-ethyl-9-methyl//acetic acid |
| 502 | 12 | C$_2$H$_5$Cl | 1,9-diethyl//acetic acid |
| 503 | 12 | CH$_2$=CHCH$_2$Br | 9-allyl-1-ethyl//acetic acid |
| 504 | 12 | 2-(dimethylamino)-ethyl chloride | 9-[2-(dimethylamino)ethyl//acetic acid |
| 505 | 13 | CH$_3$I | 9-methyl-1-propyl//acetic acid |
| 506 | 13 | n-C$_3$H$_7$Cl | 1,9-dipropyl//acetic acid |
| 507 | 13 | CH$_2$=CHCH$_2$Br | 9-allyl-1-propyl//acetic acid |
| 508 | 13 | CH$_2$=C(CH$_3$)CH$_2$Br | 9-methallyl-1-propyl//acetic acid |
| 509 | 14 | ⌬-CH$_2$Cl | 9-benzyl-1-isopropyl//acetic acid |
| 510 | 14 | CH$_2$=CHBr | 1-isopropyl-9-vinyl//acetic acid |
| 511 | 15 | n-C$_3$H$_7$Cl | 1,9-dipropyl-3-methyl//acetic acid |
| 512 | 16 | CH$_2$=CHCH$_2$Br | 9-allyl-1,4-diethyl-3-methyl//acetic acid |
| 513 | 17 | CH$_3$I | α,1,9-trimethyl//acetic acid |
| 514 | 18 | n-C$_3$H$_7$Cl | 1-cyclohexyl-α,α-dimethyl-9-propyl//acetic acid |
| 515 | 19 | CH$_2$=CHCH$_2$Br | 9-allyl-1-t-butyl//acetic acid |
| 516 | 20 | CH$_2$=CHCH$_2$I | 9-allyl-1-butyl//acetic acid |
| 517 | 23 | CH$_3$Cl | 1,9-dimethyl-6-methoxy//acetic acid |
| 518 | 28 | CH$_2$=CHBr | 6-nitro-1-propyl-9-vinyl//acetic acid |
| 519 | 32 | CH≡CCH$_2$Br | α,3-dimethyl-1-ethyl-9-propargyl-4,4,5-tripropyl//acetic acid |
| 520 | 34 | CH$_2$CHCH$_2$Br | 9-allyl-1-t-butyl-α,α-diisopropyl-3,3,4,4,5-pentaethyl//acetic acid |
| 521 | 37 | C$_2$H$_5$I | 7-hydroxy-1-(propyl)-β,β,9-triethyl//propionic acid |
| 522 | 38 | CH$_3$I | 1-cyclobutyl-3,9-dimethyl-8-nitro-α-propyl//propionic acid |
| 523 | 41 | CH$_2$=C(CH$_3$)CH$_2$Cl | 1,4,4-triethyl-9-methallyl-α,α,β-3-tetramethyl//propionic acid |
| 524 | 45 | ⌬-CH$_2$CH$_2$Br | 1-methyl-6-nitro-α,α,β,β,3-pentaethyl-9-phenethyl//propionic acid |
| 525 | 47 | 1-(3-chloro- | 1-cyclopropyl-α,β-diethyl-7- |

TABLE IX-continued

| EXAMPLE | NO. OF THE EXAMPLE IN WHICH STARTING MATERIAL IS PREPARED | ORGANIC HALIDE | PRODUCT: [(PREFIX LISTED BELOW)-1,3,4,9-TETRAHYDROPYRANO[3,4-b]-INDOLE-(SUFFIX LISTED BELOW)] PREFIX//SUFFIX |
|---|---|---|---|
| | | propyl)piperazine | ethoxy-9-(3-piperidinopropyl)//propionic acid |
| 526 | 48 | $CH_3I$ | 1,9-dimethyl//butyric acid |
| 527 | 48 | | 9-benzyl-1-methyl//butyric acid |
| 528 | 49 | $C_2H_5Cl$ | 1,9-diethyl-$\gamma$,3-dimethyl//butyric acid |
| 529 | 51 | $CH_2$=CHBr | 1-cyclobutyl-3,3-dimethyl-$\beta,\gamma,\gamma,$-4-tetrapropyl-9-vinyl//butyric acid |
| 530 | 52 | $CH_2$=CHBr | 7-chloro-$\alpha,\beta,\beta,\gamma,\gamma$,4-heptaethyl-1-methyl-9-vinyl//butyric acid |
| 531 | 58 | $C_2H_5I$ | $\alpha$-methyl-1,8,9-triethyl//butyric acid |
| 532 | 62 | $CH_3I$ | $\alpha,\beta$-diethyl-1,5-dipropyl-3,3,9-trimethyl//butyric acid |

Row 527 organic halide: 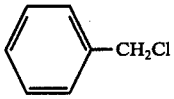

TABLE X

| EXAMPLE | NO. OF THE EXAMPLE IN WHICH STARTING MATERIAL IS PREPARED | ORGANIC HALIDE | PRODUCT: [(PREFIX LISTED BELOW)-1,3,4,9-TETRAHYDROTHIOPYRANO[3,4-b]-INDOLE-(SUFFIX LISTED BELOW)] PREFIX//SUFFIX |
|---|---|---|---|
| 533 | 3 | $CH_2$=CHCH$_2$Br | 9-allyl-1-methyl//acetic acid |
| 534 | 3 | $CH_3I$ | 1,9-dimethyl//acetic acid |
| 535 | 3 | 4-(2-chloroethyl)-morpholine | 1-methyl-9-(2-morpholineothyl)acetic acid |
| 536 | 96 | n-$C_3H_7I$ | 1-methyl-9-propyl//propionic acid |
| 537 | 96 | $CH_3I$ | 1,9-dimethyl//propionic acid |
| 538 | 96 | CH≡CCH$_2$Br | 1-methyl-9-propargyl//propionic acid |
| 539 | 96 | $CH_2$=CHCH$_2$Cl | 9-allyl-1-methyl//propionic acid |
| 540 | 65 | $CH_3I$ | 1,9-dimethyl//carboxylic acid |
| 541 | 65 | 1-(3-chloropropyl)-piperidine | 1-methyl-9-(3-piperidinopropyl)//carboxylic acid |
| 542 | 68 | $CH_3I$ | 6-hydroxy-1-(1-propyl)-3,3,9-trimethyl//carboxylic acid |
| 543 | 70 | $CH_3CH$=CHBr | 1-cyclopropyl-4-isopropyl-9-(1-propenyl)//carboxylic acid |
| 544 | 73 | $CH_3I$ | 1-ethyl-9-methyl//acetic acid |
| 545 | 73 | $C_2H_5Cl$ | 1,9-diethyl//acetic acid |
| 546 | 73 | 4-(2-chloroethyl)-morpholine | 1-ethyl-9-(2-morpholinoethyl)//acetic acid |
| 547 | 73 | CH≡CCH$_2$Br | 1-ethyl-9-propargyl//acetic acid |
| 548 | 74 | $CH_3I$ | 9-methyl-1-propyl//acetic acid |
| 549 | 74 | n-$C_3H_7Cl$ | 1,9-dipropyl//acetic acid |
| 550 | 74 | $CH_2$=CHCH$_2$Br | 9-allyl-1-propyl//acetic acid |
| 551 | 74 | $CH_2$=C(CH$_3$)CH$_2$Br | 9-methallyl-1-propyl//acetic acid |
| 552 | 75 | $CH_3I$ | 9-methyl-1-isopropyl//acetic acid |
| 553 | 75 | $CH_2$=CHBr | 1-isopropyl-9-vinyl//acetic acid |
| 554 | 76 | n-$C_3H_7Cl$ | 1,9-dipropyl-3-methyl//acetic acid |
| 555 | 76 | | 9-benzyl-3-methyl-1-propyl//acetic acid |
| 556 | 78 | $CH_3I$ | $\alpha$,1,9-trimethyl//acetic acid |
| 557 | 79 | n-$C_3H_7Cl$ | 1-cyclohexyl-$\alpha,\alpha$-dimethyl-9-propyl//acetic acid |
| 558 | 84 | $CH_3Cl$ | 1,9-dimethyl-6-methoxy//acetic acid |
| 559 | 89 | $CH_2$=CHBr | $\alpha,\alpha$-diethyl-1-methyl-9-vinyl-8-fluoro//acetic acid |
| 560 | 93 | $C_2H_5Cl$ | $\alpha$,3-dimethyl-1,9-diethyl-1-phenyl-4,4,5-tripropyl//acetic acid |
| 561 | 95 | $CH_2$=CHCH$_2$Br | 9-allyl-1-t-butyl-$\alpha,\alpha$-diisopropyl-3,3,4,4,5-pentaethyl//acetic acid |
| 562 | 98 | $C_2H_5I$ | 7-hydroxy-1-propyl-$\beta,\beta$,9-triethyl//propionic acid |
| 563 | 99 | $CH_3I$ | 1-cyclobutyl-3,9-dimethyl-8-nitro-$\alpha$-propyl//propionic acid |
| 564 | 106 | $CH_2$=CHCl | 1-methyl-6-nitro-$\alpha,\alpha,\beta,\beta$,3-pentaethyl-9-vinyl//propionic acid |
| 565 | 108 | $C_2H_5Cl$ | 1-cyclopropyl-6-ethoxy-$\alpha,\beta$,9-triethyl//propionic acid |
| 566 | 109 | $CH_3I$ | 1,9-dimethyl//butyric acid |
| 567 | 109 | $CH_2$=CHCH$_2$Cl | 9-allyl-1-methyl//butyric acid |
| 568 | 110 | $C_2H_5Cl$ | 1,9-diethyl-$\gamma$,3-dimethyl//butyric acid |
| 569 | 112 | $CH_2$=CHBr | 1-cyclobutyl-3,3-dimethyl-$\beta,\gamma,\gamma$,4-tetrapropyl-9-vinyl//butyric acid |
| 570 | 119 | $C_2H_5I$ | $\alpha$-methyl-1,8,9-triethyl//butyric acid |

Row 555 organic halide: 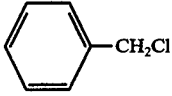

EXAMPLE 571

By following the procedure of Example 488 but using as the starting material an equivalent amount of the ester compounds of formula I in which $R^7$ is hydrogen, obtained prior to hydrolysis in Example 1 and 3 to 125, inclusive, instead of 1-methyl-1,3,4,9-tetrahydropyrano[3,4-b]indole-1-acetic acid, and using an equivalent amount of the appropriate organic halide, then the corresponding N-alkylated ester compound of formula I in which $R^7$ is lower alkyl, lower alkenyl, propargyl or phenyl(lower)alkyl is obtained.

For example, when following the procedure of Example 488, the replacement of 1-methyl-1,3,4,9-tetrahydropyrano[3,4-b]indole-1-acetic acid by an equivalent amount of its corresponding ethyl ester, described in Example 1, and then use of the same alkyl halide, methyl iodide, affords 1,9-dimethyl-1,3,4,9-tetrahydropyrano[3,4-b]-indole-1-acetic acid ethyl ester.

Similarly, the replacement of 1-methyl-1,3,4,9-tetrahydropyrano[3,4-b]indole-1-acetic acid by an equivalent amount of 1-methyl-1,3,4,9-tetrahydrothiopyrano[3,4-b]indole-1-acetic acid methyl ester, described in Example 3, affords 1,9-dimethyl-1,3,4,9-tetrahydrothiopyrano[3,4-b]indole-1-acetic acid methyl ester.

By following the procedure of Example 126 but using as starting material an equivalent amount of one of the N-alkylated acid compounds of formula I, described in Examples 488 to 570, inclusive, instead of 1-methyl-1,3,4,9-tetrahydropyrano[3,4-b]indole-1-acetic acid, and using an equivalent amount of an appropriate amine such as ammonia or a primary or secondary amine, described in Example 126, then the corresponding amide compound of formula I in which $R^7$ is lower alkyl, lower alkenyl, propargyl phenyl(lower)alkyl and amino(lower)alkyl is obtained. Examples of such amides are listed as products in Tables XI, XII, XIII, and XIV together with the appropriate starting material, noted by the example in which it is prepared, and the amine used for the preparation of the amide.

TABLE XI

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 572 | 488 (title compound) | $(CH_3)_2NH$ | N,N,1,9-tetramethyl//acetamide |
| 573 | 488 (title compound) | $CH_3NH_2$ | N,1,9-trimethyl//acetamide, m.p. 136 – 138° C. |
| 574 | 488 (title compound) | $NH_3$ | 1,9-dimethyl//acetamide, m.p. 105 – 106° C. |
| 575 | 488 (title compound) | n-$C_6H_{13}NH_2$ | 1,9-dimethyl-N-hexyl//acetamide |
| 576 | 488 (title compound) | $(C_2H_5)_2NH$ | N,N-diethyl-1,9-dimethyl//acetamide |
| 577 | 488 (N-ethyl analog) | $(CH_3)_2NH$ | 9-ethyl-N,N,1-trimethyl//acetamide, |
| 578 | 488 (N-ethyl analog) | $CH_3NH_2$ | N,1-dimethyl-9-ethyl//acetamide, m.p. 108 – 109° C. |
| 579 | 488 (N-ethyl analog) | $NH_3$ | 9-ethyl-1-methyl//acetamide, m.p. 130 –133° C. |
| 580 | 488 (N-propyl analog) | $(CH_3)_2NH$ | 9-propyl-N,N,1-trimethyl//acetamide m.p. 84 – 87° C. |
| 581 | 488 (N-propyl analog) | $CH_3NH_2$ | N,1-dimethyl-9-propyl//acetamide |
| 582 | 489 | $CH_3NH_2$ | 9-allyl-N,1-dimethylacetamide |
| 583 | 491 | $(CH_3)_2NH$ | 9-propargyl-N,N,1-trimethyl//acetamide |
| 584 | 493 | $(CH_3)_2NH$ | N,N,1,9-tetramethyl//propionamide, |
| 585 | 493 | $CH_3NH_2$ | N,1,9-trimethyl//propionamide |
| 586 | 493 | $(C_2H_5)_2NH$ | 1,9-dimethyl-N,N-diethyl//propionamide |
| 587 | 495 | $NH_3$ | 1-methyl-9-(3-piperidinopropyl)//propionamide |
| 588 | 495 | $(CH_3)_2NH$ | 9-(3-piperidinopropyl-N,N,1-trimethyl//propionamide |
| 589 | 497 | $CH_3NH_2$ | 1,3-diisopropyl-N,6-dimethyl-9-propargyl//carboxamide |
| 590 | 498 | $(C_2H_5)_2NH$ | N,N-diethyl-6-hydroxy-1,3,3,9-tetramethyl//carboxamide |
| 591 | 501 | $CH_3NH_2$ | N,9-dimethyl-1-ethyl//acetamide |
| 592 | 503 | $(C_2H_5)_2NH$ | 9-allyl-N,N,1-triethyl//acetamide |
| 593 | 504 | $(CH_3)_2NH$ | N,N-dimethyl-9-[2-(dimethylamino)-ethyl]-1-ethyl//acetamide |
| 594 | 505 | $CH_3NH_2$ | N,9-dimethyl-1-propyl//acetamide |
| 595 | 507 | $(C_2H_5)_2NH$ | 9-allyl-N,N-diethyl-1-propyl//acetamide |
| 596 | 514 | $CH_3NH_2$ | 1-cyclohexyl-9-propyl-N,α,α-trimethyl//acetamide |
| 597 | 516 | n-$C_6H_{13}NH_2$ | 9-allyl-1-butyl-N-hexyl//acetamide |
| 598 | 517 | $(CH_3)_2NH$ | 6-methoxy-N,N,1,9-tetramethyl//acetamide |
| 599 | 519 | $CH_3NH_2$ | 1-ethyl-9-propargyl-4,4,5-tripropyl-N,α,3-trimethyl//acetamide |
| 600 | 524 | $(C_2H_5)_2NH$ | N,N,α,α,β,β,3-heptaethyl-1-methyl-6-nitro-9-phenethyl//propionamide |
| 601 | 525 | $(C_2H_5)_2NH$ | 1-cyclopropyl-7-ethoxy-N,N,α,β-tetraethyl-9-(3-piperidinopropyl)//propionamide |
| 602 | 526 | $CH_3NH_2$ | N,1,9-trimethyl//butyramide |
| 603 | 527 | $(CH_3)_2NH$ | 9-benzyl-N,N,1-trimethyl//butyramide |
| 604 | 528 | $NH_2$ | 1,9-diethyl-γ,3-dimethyl//butyramide |
| 605 | 532 | $CH_3NH_2$ | α,β-diethyl-1,5-dipropyl-N,3,3,9-tetramethyl//butyramide |

TABLE XII

| EXAMPLE | NO. OF THE EXAMPLE IN WHICH STARTING MATERIAL IS PREPARED | AMINE | PRODUCT: (PREFIX LISTED BELOW)-(1,3,4,9-TETREHYDROPYRANO[3,4-b]-INDOLE-1-YL)-(SUFFIX LISTED BELOW)] PREFIX//SUFFIX |
|---|---|---|---|
| 606 | 488 (title compound) | pyrrolidine | 1-[(1,9-dimethyl//acetyl]pyrrolidine, |
| 607 | 488 (title compound) | piperidine | 1-[(1,9-dimethyl//acetyl]piperidine, |
| 608 | 488 (title compound) | morpholine | 1-[(1,9-dimethyl//acetyl]morpholine, |
| 609 | 488 (title compound) | N-methyl-piperazine | 1-methyl-4-[1,9-dimethyl//acetyl]-piperazine |
| 610 | 488 (N-ethyl analog) | pyrrolidine | 1-[(9-ethyl-1-methyl//acetyl]-pyrrolidine |
| 611 | 488 (N-ethyl analog) | piperidine | 1-[(9-ethyl-1-methyl//acetyl]-piperidine |
| 612 | 488 (N-propyl analog) | morpholine | 1-[(1-methyl-9-propyl//acetyl]-morpholine |
| 613 | 488 (title compound) | N-piperazine-ethanol | 1-(2-hydroxyethyl)-4-[1,9-dimethyl//acetyl]piperazine, $\gamma_{max}^{film}$ 1625 cm$^{-1}$. |
| 614 | 492 | pyrrolidine | 1-[(1-methyl-9-propyl//propionyl]-pyrrolidine |
| 615 | 493 | piperidine | 1-[(1,9-dimethyl//propionyl]-piperidine |
| 616 | 494 | morpholine | 1-[(1-methyl-9-phenethyl//propionyl] morpholine |
| 617 | 495 | piperazine | 1-[1-methyl-9-(3-piperidinopropyl)//propionyl]piperazine |
| 618 | 496 | pyrrolidine | 1-{1-methyl-9-[2-(1-pyrrolidinyl)-ethyl]//carbonyl}pyrrolidine |
| 619 | 501 | morpholine | 1-[(1-ethyl-9-methyl//acetyl]-morpholine |
| 620 | 502 | N-piperazine-propanol | 1-(3-hydroxypropyl)-4-[1,9-diethyl//acetyl]piperazine |
| 621 | 505 | pyrrolidine | 1-[(9-methyl-1-propyl//acetyl]-pyrrolidine |
| 622 | 507 | morpholine | 1-[(9-allyl-1-propyl//acetyl]-morpholine |
| 623 | 509 | piperidine | 1-[(9-benzyl-1-isopropyl//acetyl]-piperidine |
| 624 | 511 | piperazine | 1-[(1,9-dipropyl-3-methyl//acetyl]-piperazine |
| 625 | 513 | N-ethyl-piperazine | 1-ethyl-4-[($\alpha$,1,9-trimethyl-$\alpha$//acetyl]piperazine |
| 626 | 525 | N-propyl-piperazine | 1-propyl-4-[(1-cyclopropyl-$\alpha$,$\beta$-diethyl-6-ethoxy-9-(3-piperidino-propyl//propionyl]piperazine |
| 627 | 566 | pyrrolidine | 1-[(1,9-dimethyl//butyryl]-pyrrolidine |
| 628 | 527 | N-piperazine-methanol | 9-benzyl-1-(hydroxymethyl)-4-[(1-methyl//butyryl]piperazine |
| 629 | 530 | morpholine | 1-[(7-chloro-$\alpha$,$\beta$,$\beta$,$\gamma$,$\gamma$,4,4-heptaethyl-1-methyl-9-vinyl//butyryl]morpholine |

TABLE XIII

| EXAMPLE | NO. OF THE EXAMPLE IN WHICH STARTING MATERIAL IS PREPARED | AMINE | PRODUCT:[(PREFIX LISTED BELOW)-1,3,-4,9-TETRAHYDROTHIOPYRANO[3,4-b]-INDOLE-1-(SUFFIX LISTED BELOW)] PREFIX//SUFFIX |
|---|---|---|---|
| 630 | 534 | (CH$_3$)$_2$NH | N,N,1,9-tetramethyl//acetamide |
| 631 | 534 | CH$_3$NH$_2$ | N,1,9-trimethyl//acetamide |
| 632 | 534 | NH$_3$ | 1,9-dimethyl//acetamide |
| 633 | 534 | n-C$_6$H$_{13}$NH$_2$ | 1,9-dimethyl-N-hexyl//acetamide |
| 634 | 534 | (C$_2$H$_5$)$_2$NH | N,N-diethyl-1,9-dimethyl//acetamide |
| 635 | 533 | (CH$_3$)$_2$NH | 9-allyl-N,N,1-trimethyl//acetamide |
| 636 | 537 | CH$_3$NH$_2$ | N,1,9-trimethyl//propionamide |
| 637 | 537 | (C$_2$H$_5$)$_2$NH | 1,9-dimethyl-N,N-diethyl//propion-amide |
| 638 | 539 | NH$_3$ | 9-allyl-1-methyl//propionamide |
| 639 | 539 | (CH$_3$)$_2$NH | 9-allyl-N,N,1-trimethyl//propionamide |
| 640 | 541 | CH$_3$NH$_2$ | N,1-dimethyl-9-(3-piperidinopropyl)//carboxamide |
| 641 | 542 | (C$_2$H$_5$)$_2$NH | N,N-diethyl-6-hydroxy-1-propyl-3,3,9-trimethyl//carboxamide |
| 642 | 544 | CH$_3$NH$_2$ | N,9-dimethyl-1-ethyl//acetamide |
| 643 | 546 | (C$_2$H$_5$)$_2$NH | 9-(2-morpholinoethyl)-N,N,1-treiethyl//acetamide |
| 644 | 547 | (CH$_3$)$_2$NH | N,N-dimethyl-1-ethyl-9-propargyl//acetamide |
| 645 | 548 | CH$_3$NH$_2$ | N,9-dimethyl-1-propyl//acetamide |
| 646 | 550 | (C$_2$H$_5$)$_2$NH | 9-allyl-N,N-diethyl-1-propyl//acetamide |
| 647 | 557 | CH$_3$NH$_2$ | 1-cyclohexyl-9-propyl-N,$\alpha$,$\alpha$-trimethyl//acetamide |
| 648 | 558 | (CH$_3$)$_2$NH | 6-methoxy-N,N,1,9-tetramethyl//acetamide |
| 649 | 564 | (C$_2$H$_5$)$_2$ | N,N,$\alpha$,$\alpha$,$\beta$,$\beta$,3-heptaethyl-1-methyl-6-nitro-9-vinyl//propionamide |
| 650 | 565 | (C$_2$H$_5$)$_2$NH | 1-cyclopropyl-6-ethoxy-N,N,$\alpha$,$\beta$,9-pentaethyl//propionamide |
| 651 | 566 | CH$_3$NH$_2$ | N,1,9-trimethyl//butyramide |
| 652 | 567 | (CH$_3$)$_2$NH | 9-allyl-N,N,1-trimethyl//butyramide |

TABLE XIII-continued

| EXAMPLE | NO. OF THE EXAMPLE IN WHICH STARTING MATERIAL IS PREPARED | AMINE | PRODUCT:[(PREFIX LISTED BELOW)-1,3,-4,9-TETRAHYDROTHIOPYRANO[3,4-b]-INDOLE-1-(SUFFIX LISTED BELOW)] PREFIX//SUFFIX |
|---|---|---|---|
| 653 | 568 | $NH_2$ | 1,9-diethyl-γ,3-dimethyl//butyramide |

TABLE XIV

| EXAMPLE | NO. OF THE EXAMPLE IN WHICH STARTING MATERIAL IS PREPARED | AMINE | PRODUCT: [(PREFIX LISTED BELOW)-1,3,-4,9-TETRAHYDROTHIOPYRANO[3,4-b]-INDOLE-1-YL)-(SUFFIX LISTED BELOW)] PREFIX//SUFFIX |
|---|---|---|---|
| 654 | 533 | pyrrolidine | 1-[(9-allyl-1-methyl//acetyl]-pyrrolidine |
| 655 | 534 | piperidine | 1-[(1,9-dimethyl//acetyl]piperidine |
| 656 | 535 | morpholine | 1-[(1-methyl-9-(2-morpholino-ethyl)//acetyl]morpholine |
| 657 | 536 | pyrrolidine | 1-[(1-methyl-9-propyl//propionyl]-pyrrolidine |
| 658 | 537 | piperidine | 1-[(1,9-dimethyl//propionyl]-piperidine |
| 659 | 538 | morpholine | 1-[(1-methyl-9-propargyl//propionyl]morpholine |
| 660 | 539 | piperazine | 1-[9-allyl-1-methyl//propionyl]-piperazine |
| 661 | 539 | N-methyl-piperazine | 1-methyl-4-[9-allyl-1-methyl//propionyl]piperazine |
| 662 | 540 | pyrrolidine | 1-[1,9-dimethyl//carbonyl]-pyrrolidine |
| 663 | 541 | morpholine | 1-{(1-methyl-9-(3-piperidino-propyl)//carbonyl}morpholine |
| 664 | 544 | morpholine | 1[(1-ethyl-9-methyl//acetyl]-morpholine |
| 665 | 547 | N-piperazine-propanol | 1-(3-hydroxypropyl)-4-[(1-ethyl-9-propargyl//acetyl]piperazine |
| 666 | 548 | pyrrolidine | 1-[(9-methyl-1-propyl//acetyl]-pyrrolidine |
| 667 | 549 | morpholine | 1-[(1,9-dipropyl//acetyl]-morpholine |
| 668 | 552 | piperidine | 1-[(1-isopropyl-9-methyl//acetyl]piperidine |
| 669 | 555 | piperazine | 1-[9-benzyl-3-methyl-1-propyl//acetyl]piperazine |
| 670 | 556 | N-ethyl-piperazine | 1-ethyl-4-[α,1,9-trimethyl//acetyl]piperazine |
| 671 | 565 | N-propyl-pyrazine | 1-propyl-4-[(1-cyclopropyl-6-ethoxy-α,β,9-triethyl//propionyl]-piperazine |
| 672 | 566 | pyrrolidine | 1-[(1,9-dimethyl//butyryl]-pyrrolidine |
| 673 | 567 | N-piperazine-methanol | 1-(hydroxymethyl)-4-[9-allyl-1-methyl//butyryl]piperazine |

EXAMPLE 674

1,9-DIMETHYL-1-[2-(DIMETHYLAMINO)E-THYL]-1,3,4,9-TETRAHYDROPYRANO[3,4-b]IN-DOLE[I; $R^1$ = $CH_3$, $R^2$, $R^3$, $R^4$, $R^5$, AND $R^6$ = H, $R^7$ = $CH_3$, X = O AND Y = $CH_2CH_2N(CH_3)_2$]

A solution of N,N,1,9-tetramethyl-1,3,4,9-tetrahydropyrano[3,4-b]indole-1-acetamide (12.0 g), described in Example 572, in dry tetrahydrofuran (100 ml.) is added dropwise to a mechanically stirred mixture of lithium aluminium hydride (5 g) in dry tetrahydrofuran (THF) (100 ml.). The mixture is heated at reflux for twenty hours under nitrogen. Water-THF (1:1, 50 ml.) is added to destroy the excess hydride. The mixture is filtered through celite, diluted with water (300 ml.) and extracted three times with ether. The organic phase is dried over sodium sulfate, filtered and evaporated to dryness under reduced pressure to yield the title compound, nmr ($CDCl_3$) δ 1.66 (3H), 2.70 (6H), 3.83 (3H).

The corresponding hydrochloric acid addition salt, 1,9-dimethyl-1-[2-(dimethylamino)ethyl]-1,3,4,9-tetrahydropyrano[3,4-b]indole hydrochloride, has m.p., 229° - 230° C. after crystallization from methylene dichloride-benzene.

By following the procedure of Example 674 but using as starting material an equivalant amount of one of the N-alkylated amide compounds of formmula VII, described in Examples 573 to 673 instead of N,N1,9-tetramethyl-1,3,4,9-tetrahydro[3,4-b]indole-1-acetamide then the corresponding N-alkylated amine compound of formula I is obtained. Examples of such compounds are listed as products in Tables XV and XVI together with the appropriate starting material. In each case the starting material is noted by the example in which it is prepared.

TABLE XV

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]INDOLE |
|---|---|---|
| 675 | 573 | 1,9-dimethyl-1-[2-(methylamino)ethyl] |
| 676 | 574 | 1-(2-aminoethyl)-1,9-dimethyl |
| 677 | 575 | 1,9-dimethyl-1-[2-(hexylamino)ethyl] |
| 678 | 576 | 1-[2-(diethylamino)ethyl]-1,9-dimethyl, nmr ($CDCl_3$) δ 0.94 (t, 6H), (S, 3H), |

TABLE XV-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]INDOLE |
|---|---|---|
| | | 2.50 (m, 10H). |
| 679 | 577 | 1-[2-(dimethylamino)ethyl]-9-ethyl-1-methyl, nmr (CDCl$_3$) δ 1.39 (3H), 1.70 (3H), 2.73 (m,12H), corresponding hydrochloric |
| | | acid addition salt has m.p. 202-205° C. |
| 680 | 578 | 9-ethyl-1-methyl-1-[2-(methylamino)ethyl] |
| 681 | 579 | 1-(2-aminoethyl)-9-ethyl-1-methyl |
| 682 | 580 | 1-[2-(dimethylamino)ethyl]-1-methyl-9-propyl, nmr (CDCl$_3$), δ 1.00 (t, 3H), 1.65 (S, 3H), corresponding maleic acid addition salt has m.p. 125-126° C. |
| 683 | 581 | 1-methyl-1-[2-(methylamino)ethyl]-9-propyl |
| 684 | 582 | 9-allyl-1-methyl-1-[2-(methylamino)ethyl] |
| 685 | 583 | 1-[2-(dimethylamino)ethyl]-1-methyl-9-propargyl |
| 686 | 584 | 1,9-dimethyl-1-[3-(dimethylamino)propyl], nmr (CDCl$_3$) δ 1.60 (3H), 2.68 (6H), corresponding maleic acid addition salt has m.p. 115-118° C. |
| 687 | 585 | 1,9-dimethyl-1-[3-(methylamino)propyl] |
| 688 | 586 | 1-[3-(diethylamino)propyl]-1,9-dimethyl |
| 689 | 587 | 1-(3-aminopropyl)-1-methyl-9-(3-piperidinopropyl) |
| 690 | 588 | 1-[3-(dimethylamino)propyl-1-methyl-9-(3-piperidinopropyl) |
| 691 | 589 | 1,3-diisopropyl-1-methyl-1-(methylamino)-methyl-9-propargyl |
| 692 | 590 | 1-(diethylamino)methyl-6-hydroxy-1,3,3,9-tetramethyl |
| 693 | 591 | 1-ethyl-9-methyl-1-[2-(methylamino)ethyl] |
| 694 | 592 | 9-allyl-1-[2-(diethylamino)ethyl]-1-ethyl |
| 695 | 593 | 1,9-bis-[2-(dimethylamino)ethyl]-1-ethyl |
| 696 | 594 | 9-methyl-1-[2-(methylamino)ethyl-1-propyl |
| 697 | 595 | 9-allyl-1-[2-(diethylamino)ethyl]-1-propyl |
| 698 | 596 | 1-cyclohexyl-1-[1,1-dimethyl-2-(methylamino)ethyl]-9-propyl |
| 699 | 597 | 9-allyl-1-butyl-1-[2-(hexylamino)ethyl] |
| 700 | 598 | 1,9-dimethyl-1-[2-(dimethylamino)ethyl]-6-methoxy |
| 701 | 599 | 1-ethyl-3-methyl-1-[1-methyl-2-(methylamino)ethyl]-9-propargyl-4,4,5-tripropyl |
| 702 | 600 | 1-[3-(diethylamino)-1,1,2,2-tetraethylpropyl]-3-ethyl-1-methyl-6-nitro-9-phenethyl |
| 703 | 601 | 1-cyclopropyl-1-[1,2-diethyl-3-(diethylamino)propyl]-7-ethoxy-9-(3-piperazinopropyl) |
| 704 | 602 | 1,9-dimethyl-1-[4-(methylamino)butyl] |
| 705 | 603 | 9-benzyl-1-[4-(dimethylamino)butyl]-1-methyl |
| 706 | 604 | 1,9-diethyl-1-(4-amino-1-methylbutyl) |
| 707 | 605 | 1-[2,3-diethyl-4-(methylamino)butyl]-1,5-dipropyl-3,3,9-trimethyl |
| 708 | 606 | 1,9-dimethyl-1-[2-(1-pyrrolidinyl)ethyl], nmr (CDCl$_3$) δ1.62 (s, 3H), 3.74 (s, 3H). |
| 709 | 607 | 1,9-dimethyl-1-(2-piperidinoethyl), nmr (CDCl$_3$) δ1.61 (s, 3H), 2.32 (m, 6H), 9.81 ((m, 2H), m.p. of corresponding hydrochloric acid addition salt, 233-235° C. |
| 710 | 608 | 1,9-dimethyl-1-(2-morpholinoethyl) |
| 711 | 609 | 1,9-dimethyl-1-[2-(4-methyl-1-piperazinyl)-ethyl], nmr (CDCl$_3$) δ1.56 (s, 3H), 2.22 (s, 3), 2.3 (m, 8H). |
| 712 | 610 | 9-ethyl-1-methyl-1-[2-(1-pyrrolidinyl)-ethyl] |
| 713 | 611 | 9-ethyl-1-methyl-1-(2-piperidinoethyl) |
| 714 | 612 | 1-methyl-1-(2-morpholinoethyl)-9-propyl |
| 715 | 613 | 1,9-dimethyl-1-{2-[4-(2-hydroxyethyl)-1-piperazinyl]ethyl}, nmr (CDCl$_3$) δ1.60 (s, 3H), 3.70 (s, 3H), m.p. of corresponding dihydrochloride salt, m.p. 219-220° C. |
| 716 | 614 | 1-methyl-9-propyl-1-[3-(1-pyrrolidinyl)-propyl] |
| 717 | 615 | 1,9-dimethyl-1-(3-piperidinopropyl) |
| 718 | 616 | 1-methyl-1-(3-morpholinopropyl)-9-phenethyl |
| 719 | 617 | 1,9-bis-(3-piperazinopropyl)-1-methyl |
| 720 | 618 | 1-methyl-1-[(1-piperazinyl)methyl]-9-[2-(1-pyrrolidinyl)ethyl] |
| 721 | 619 | 1-ethyl-9-methyl-1-(2-morpholinoethyl) |
| 722 | 620 | 1,9-diethyl-1-{2-]4-(3-hydroxypropyl)-1-piperazinyl]ethyl} |
| 723 | 621 | 9-methyl-1-propyl-1-[2-(1pyrrolidinyl)-ethyl] |
| 724 | 622 | 9-allyl-1-(2-morpholinoethyl)-1-propyl |
| 725 | 623 | 9-benzyl-1-isopropyl-1-(2-piperidinoethyl) |
| 726 | 624 | 1,9-dipropyl-3-methyl-1-(2-piperazinoethyl) |
| 727 | 625 | 1,9-dimethyl-1-[1-methyl-2-(4-methyl-1-piperazinyl)ethyl] |
| 728 | 626 | 1-cyclopropyl-1-{1,2-diethyl-3-(4-propyl-1-piperazinyl)propyl}-6-ethoxy-9-(3-piperidinopropyl) |
| 729 | 627 | 1,9-dimethyl-1-[4-(1-pyrrolidinyl)butyl] |

TABLE XV-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]INDOLE |
|---|---|---|
| 730 | 628 | 9-benzyl-1-{4-[4-(hydroxymethyl)-1-piperazinyl]butyl}-1-methyl |
| 731 | 629 | 7-chloro-4,4-diethyl-1-methyl-1-(4-morpholino-1,1,2,2,3-pentaethylbutyl)-9-vinyl |

TABLE XVI

| EXAMPLE | NO. OF THE EXAMPLE IN WHICH STARTING MATERIAL IS PREPARED | PRODUCT: (PREFIX LISTED BELOW)-1,3,4,9-TETRAHYDROTHIOPYRANO[3,4-b]INDOLE |
|---|---|---|
| 732 | 630 | 1,9-dimethyl-1-[2-(dimethylamino)ethyl], nmr (CDCl$_3$) δ3.72 (s,6H), 6.40 (s,3H) |
| 733 | 631 | 1,9-dimethyl-1-[2-(methylamino)ethyl] |
| 734 | 632 | 1-(2-aminoethyl)-1,9-dimethyl |
| 735 | 633 | 1,9-dimethyl-1-[2-(hexylamino)ethyl] |
| 736 | 634 | 1-[2-(diethylamino)ethyl]-1,9-dimethyl |
| 737 | 635 | 9-allyl-1-[2-(dimethylamino)ethyl]-1-methyl |
| 738 | 636 | 1,9-dimethyl-1-[3-(methylamino)propyl] |
| 739 | 637 | 1-[3-(diethylamino)propyl]-1,9-dimethyl |
| 740 | 638 | 9-allyl-1-(3-aminopropyl)-1-methyl |
| 741 | 639 | 9-allyl-1-[3-(dimethylamino)propyl]-1-methyl |
| 742 | 640 | 1-methyl-1-[(methylamino)methyl]-9-(3-piperidinopropyl) |
| 743 | 641 | 1-[(diethylamino)methyl]-6-hydroxy-1-propyl-3,3,9-trimethyl |
| 744 | 642 | 1-ethyl-9-methyl-1-[2-(methylamino)ethyl] |
| 745 | 643 | 1-[2-(diethylamino)ethyl]-1-ethyl-9-(2-morpholinoethyl) |
| 746 | 644 | 1-[2-(dimethylamino)ethyl]-1-ethyl-9-propargyl |
| 747 | 645 | 9-methyl-1-[2-(methylamino)ethyl]-1-propyl |
| 748 | 646 | 9-allyl-1-[2-(diethylamino)ethyl]-1-propyl |
| 749 | 647 | 1-cyclohexyl-1-[1,1-dimethyl-2-(methylamino)ethyl]-9-propyl |
| 750 | 648 | 1,9-dimethyl-1-[2-(dimethylamino)ethyl]-6-methoxy |
| 751 | 649 | 1-[3-(diethylamino)-1,1,2,2-tetramethylpropyl]-3-ethyl-6-nitro-9-vinyl |
| 752 | 650 | 1-cyclopropyl-1-[1,2-diethyl-3-(diethylamino)propyl]-6-ethoxy-9-ethyl |
| 753 | 651 | 1,9-dimethyl-1-[4-(methylamino)butyl] |
| 754 | 652 | 9-allyl-1-[4-(dimethylamino)butyl]-1-methyl |
| 755 | 653 | 1-[4-amino-1-methylbutyl)-1,9-diethyl-3-methyl |
| 756 | 654 | 9-allyl-1-methyl-1-[2-(1-pyrrolidinyl)ethyl] |
| 757 | 655 | 1,9-dimethyl-1-(2-piperidinoethyl) |
| 758 | 656 | 1-methyl-1,9-bis(2-morpholinoethyl) |
| 759 | 657 | 1-methyl-9-propyl-1-[3-(1-pyrrolidinyl)propyl] |
| 760 | 658 | 1,9-dimethyl-1-(3-piperidinopropyl) |
| 761 | 659 | 1-methyl-1-(3-morpholinopropyl)-9-propargyl |
| 762 | 660 | 9-allyl-1-methyl-1-(3-piperazinopropyl) |
| 763 | 661 | 9-allyl-1-methyl-1-[3-(4-methyl-1-piperazinyl)propyl] |
| 764 | 662 | 1,9-dimethyl-1-[(1-pyrrolidinyl)methyl] |
| 765 | 663 | 1-methyl-1-(morpholinomethyl)-9-(3-piperidinopropyl) |
| 766 | 664 | 1-ethyl-9-methyl-1-(2-morpholinoethyl) |
| 767 | 665 | 1-ethyl-1-{2-[4-(3-hydroxypropyl)-1-piperazinyl]ethyl}-9-propargyl |
| 768 | 666 | 9-methyl-1-propyl-1-[2-(1-pyrrolidinyl)ethyl] |
| 769 | 667 | 1,9-dipropyl-1-(2-morpholinoethyl) |
| 770 | 668 | 1-isopropyl-9-methyl-1-(2-piperidinoethyl) |
| 771 | 669 | 9-benzyl-3-methyl-1-(2-piperazinoethyl)-1-propyl |
| 772 | 670 | 1,9-dimethyl-1-[1-methyl-2-(4-methyl-1-piperazinyl)ethyl] |
| 773 | 671 | 1-cyclopropyl-6-ethoxy-9-ethyl-1-[1,2-diethyl-3-(4-propyl-1-piperazinyl)propyl] |
| 774 | 672 | 1,9-dimethyl-1-[4-(1-pyrrolidinyl)butyl] |
| 775 | 673 | 9-allyl-1-{4-[4-(hydroxymethyl)-1-piperazinyl]butyl}-1-methyl |

EXAMPLE 776

1-METHYL-1,3,4,9-TETRAHYDROPYRANO[3,4-b]INDOLE-1-CARBOXAMIDE (VII; $R^1$ = CH$_3$, $R^2$, $R^3$, $R^4$, $R^5$, $R^6$ AND $R^7$ = H, X = O, and Z = CONH$_2$ By following the procedure of Example 1 but using boron trifluoride-ethanole as the acid catalyst and an equivalent amount of pyruvamide instead of ethyl acetoacetate, 1-methyl-1,3,4,9-tetrahydropyrano[3,4-b]indole-1-carboxamide, m.p. 188° – 189° C. after recrystallization from benzene-hexene, identical with the product of Example 133, is obtained.

In the same manner but using an equivalent amount of the appropriate starting material of formula II together with the appropriate α-, β-, γ- or δ-ketoamide, the products listed in Tables III and IV are obtained. For example, by using tryptophol (II; $R^2$, $R^3$, $R^4$, $R^5$, $R^6$ = H and $X^1$ = OH) and the β-ketoamide, N,N-dimethylacetoacetamide, in the procedure of this Example, N,N,1-trimethyl-1,3,4,9-tetrahydropyrano[3,4-b]indole-1-acetamide, identical with the product of Example 126, is obtained.

EXAMPLE 777

1-METHYL-1,3,4,9-TETRAHYDROPYRANO[3,4-b]INDOLE-1-CARBOXALDEHYDE

A mixture of the starting material, tryptophol (32.2 g., 0.2 mole), acetonyl acetate (23.2 g, 0.2 mole) and 3.2 g of p-toluenesulfonic acid in 500 ml of benzene is refluxed for 1½ hr. in the presence of a Dean-Stark water trap. The benzene solution is washed with 5% sodium bicarbonate, water, dried and evaporated to afford an oil. The oil is subjected to chromatography on a silica gel column using 10% ethyl acetate in benzene as eluent. The acetate 1-methyl-1,3,4,9-tetrahydropyrano[3,4-b]indole-1-methanol acetate is obtained as an oil, nmr($CDCl_3$) δ 1.52 (S,3H), 2.08(S,3H), 4.35(2H).

This acetate is dissolved in 250 ml of methanol and stirred at room temperature. To this solution is added dropwise 20 ml of 10NaOH. Hydrolysis is immediate. Most of the methanol is removed under reduced pressure, and water is added. The mixture is rendered neutral and extracted with chloroform. The chloroform extract is dried and evaporated to afford the primary alcohol, 1-methyl-1,3,4,9-tetrahydropyrano[3,4-b]indole-1-methanol, m.p. 145° - 147° C., nmr($CDCl_3$), δ 1.43 (s,3H), 2.68 (t, J = 5.5 cps, 2H), 3.65 (d, J = 6 cps, 2H), 3.86 (t, J = 5.5 cps, 2H), after crystallization from benzene-petroleum ether.

N,N-dicyclohexylcarbodiimide (17.36 g, 0.084 mole) is added to a cooled, stirred solution of the above primary alcohol (6.09 g, 0.028 mole) in 63 ml of dimethyl sulfoxide-benzene (2:1) containing trifluoroacetic acid (1.12 ml, 0.014 mole) and pyridine (2.24 ml, 0.028 mole). The reaction is stirred at room temperature under nitrogen for 5hr. The reaction mixture is now diluted with 600 ml of ether, followed by the dropwise addition of a solution of oxalic acid (7.56 g) in 21 ml of methanol. After thirty minutes, water (600 ml) is added and the insoluble material is collected. The organic phase is washed with water (2X), 5% aqueous sodium bicarbonate (2X) and water (2X). After drying ($MgSO_4$) the organic phase is evaporated to yield an oil. The oil is purified by chromatography on silica gel. Elution with 10% ether in benzene affords the title compound as eluate, nmr ($CDCl_3$) δ1.59 (s,3H), 2.84 (t, J = 5.5 cps, 2H), 4.15 (t, J = 5.5 cps, 2H).

EXAMPLE 778

1-Methyl-1,3,4,9-tetrahydropyrano[3,4-b]indole-1-carboxaldehyde, described in Example 777, is treated with an excess of dimethylamine according to the method of K. N. Campbell, et al., J. Amer. Chem. Soc., 70, 3868 (1948), to yield the corresponding Schiff base. Reduction of the latter compound with sodium borohydride according to the procedure described by E. Schenker, Angew Chem., 73, 81 (1961), affords 1-[2-(dimethylamino)]-1-methyl-1,3,4,9-tetrahydropyrano[3,4-b]indole, identical to the product of Example 309.

By following the procedures of Examples 777 and 778 in sequence, but using a starting material in Example 777 an equivalent amount of the appropriate starting material of formula II, for example, those described in Examples 1 to 125, inclusive, and using an equivalent amount of the appropriate ketoalcohol lower alkyl ester of formula VI, described above, and in the procedure of Example 778 using an appropriate amine of formula $HNR^8R^9$ in which $R^8$ and $R^9$ are as defined in the first instance, then the respective compounds of formula I, for example, those described in Example 309 (other than the title compond) to 487, inclusive, are obtained.

More specifically exemplified, the use of indole-3-ethanethiol, acetonyl acetate and n-hexylamine in the manner just described for the starting material of formula II, the appropriate ketoalcohol lower alkyl ester and amine, respectively, yields 1-[2-(hexylamino)ethyl]-1-methyl-1,3,4,9-tetrahydrothiopyrano[3,4-b]indole.

EXAMPLE 779

Oxidation of 1-methyl-1,3,4,9-tetrahydropyrano[3,4-b]indole-1-carboxaldehyde, described in Example 777, with silver oxide according to the method of Delepine and Bonnet, cited above, affords 1-methyl-1,3,4,9-tetrahydropyrano[3,4-b]indole-1-carboxylic acid, nmr ($CDCl_3$) δ1.79 (s, 3H), 2.83 (t, 2H), 4.17 (t, 2H), 9.20 (1H), identical to the product obtained in Example 4.

By following the procedures of Examples 777 and 779, in sequence, but using as starting material an equivalent amount of the appropriate starting material of formula II, for example, those described in Examples 1 to 125, inclusive, instead of tryptophol, and using an equivalent amount of the appropriate ketoalcohol lower alkyl ester of formula VI, in which $R^1$ is as defined in the first instance and Z is $CH_2OCOR^{20}$ or $Alk^1CH_2OCOR^{20}$ wherein $R^{20}$ and $Alk^1$ are as defined in the first instance, then the acid compound of formula I in which $R^7$ is hydrogen and Y is COOH or $Alk^1COOH$ wherein $Alk^1$ is as defined above, for example, the respective products of Examples 1 to 125, inclusive, are obtained.

More specifically exemplified, according to the procedures of Examples 777 and 779, the use of tryptophol and 6-acetoxy-2-hexanone, affords 1-methyl-1,3,4,9-tetrahydrothiopyrano[3,4-b]indole-1-butyric acid, identical to the product of Example 48. Similarly, the use of tryptophol and 5-acetoxypentan-2-one affords 1-methyl-1,3,4,9-tetrahydropyrano[3,4-b]indole-1-propionic acid, identical to the product of Example 2.

EXAMPLE 780

1-(AMINOMETHYL)-1METHYL-1,3,4,9-TETRAHYDROPYRANO[3,4-b]INDOLE(I, $R^1$ = $CH_3$, $R^2$, $R^3$, $R^4$, $R^5$, $R^6$ and $R^7$ = H, X = O and Y = $CH_2NH_2$ A solution of 1-methyl-1,3,4,9-tetrahydropyrano[3,4-b]indole-1-carboxaldehyde (547 mg), described in Example 777, aqueous hydroxylamine hydrochloride (2.5 ml of 5N) and aqueous sodium acetate (2.5 ml of 5N) and methanol (5 ml) is heated at 50° - 60° C. for 5 min. and then kept at 4° C. for 16 hr. The precipitate is collected and recrystallized from ethanol water to afford 1-methyl-1,3,4,9-tetrahydropyrano[3,4-b]indole-1-carboxaldehyde oxime, m.p. 176° - 178° C.

The latter compound (230 mg) in dry THF (10 ml) is added dropwise to a stirred mixture of lithium aluminum hydride (200 mg) in 15 ml. of THF at ice bath temperature. The mixture is stirred for 1 hr., during which time it is allowed to come to room temperature. Excess lithium aluminum hydride is destroyed by the careful addition of H₂O/THF(1:1). Insoluble material is collected on a filter and the filtrate is concentrated. The concentrate is taken up in ether. The ether solution is dried (MgSO₄), filtered and concentrated to afford the title compound, identical with the compound of the same name described in Example 316.

EXAMPLE 781

1-METHYL-1-[3-(1-PYRROLIDINYL)PROPYL]-1,3,4,9-TETRAHYDROPYRANO[3,4-b] INDOLE[I, $R^1 = CH_3$, $R^2$, $R^3$, $R^4$, $R^5$, $R^6$, and $R^7 = H$, $X = O$ AND $Y =$

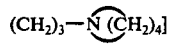

To a solution of tryptophol (15 g, 0.09 M) in 150 ml of benzene, 5-chloro-2-pentanone (12 g, 0.10 M) is added. The mixture is heated in the presence of 200 mg of p-toluenesulfonic acid and hydrated alkali-aluminum silicate (Molecular Sieves No. 4). After 1 hr. of refluxing, 400 mg more of acid is added. After a total of 2 hr. the reaction is cooled, filtered and washed with 5% sodium bicarbonate, water and dried over sodium sulfate. Evaporation under reduced pressure affords an oil. This oil is purified by chromatography on silica gel. Elution with benzene and concentratio of the eluent gives 1-(3-chloropropyl)-1-methyl-1,3,4,9-tetrahydropyrano[3,4-b]indole, nmr (CDCl₃) δ1.33 (3H); 1.93 (4H), 2.75 (2H).

A solution of the latter compound (250 mg., 0.9 millimoles) in 10 ml of THF and 1.5 ml of pyrrolidine is heated at reflux for 16 hr. The mixture is concentrated under reduced pressure and the residue partitioned between 5% sodium carbonate and chloroform. The organic phase is washed with water, dried (Na₂SO₄), filtered and evaporated under reduced pressure to give the title compound, identical with the product of Example 365.

By following the procedure of Example 781 but using as starting material an equialent amount of the appropriate starting material of formula II, for example, those described in Examples 1 to 125, inclusive, instead of tryptophol, and using an equivalent amount of the appropriate β-, γ-, or δ-haloketone of formula VI, described above, and the appropriate amine of formula HNR⁸R⁹, described above, then the respective compounds of formula I, for example those described in Examples 309 to 487, inclusive, are obtained.

EXAMPLE 782

1-[(ETHYLAMINO)METHYL]-1-METHYL-1,3,4,9-TETRAHYDROPYRANOL[3,4b]INDOLE(I, $R^1$ = CH₃, $R^2$, $R^3$, $R^4$, $R^5$, $R^6$ AND $R^7 = H$, $X = O$ and $Y =$ CH₂NHCH₃)

A mixture of tryptophol (3.86 g; II, $R^2$, $R^3$, $R^4$, $R^5$, $R^6$ = H and $X^1$=OH) and acetamidoacetone (3.0 g), see R. H. Wileg and O. H. Borum, J. Amer. Chem. Soc., 70, 2005 (1948), in 300 ml of dry benzene is stirred and heated to reflux. Water is collected in a Dean-Stark trap. After removal of the water five drops of boron trifluoride-etherate is added and the mixture refluxed 30 min. using the water-separator again. After stirring at room temperature overnight, the reaction mixture is evaporated to dryness. The solid residue is dissolved in chloroform and washed successively with 10% aqueous sodium bicarbonate, water, and brine. The chloroform solution is dried over magnesium sulfate, filtered, and evaporated. The residue is crystallized from benzene to yield 1-(acetamidomethyl)-1-methyl-1,3,4,9-tetrahydropyrano[3,4-b]indole, m.p. 100° - 102° C. This product is dried under reduced pressure at 27° C. Spectroscopic and analytical data show that the compound is solvated with one mole of benzene which can be removed completely only by melting. $R_f$ values of the amide and tryptophol are equal.

The latter product (2.4 g) is dissolved in 80 ml of dry THF and added to a suspension of lithium aluminum hydride in 200 ml of THF.

The resultant slurry is stirred and heated to reflux for 2 hr. cooled and 2.4 g of lithium aluminum hydride is added. The mixture is then refluxed with stirring overnight. The reaction mixture is decomposed with 22.4 ml of water added dropwise over 3 hr. upon stirring and cooling. Stirring is continued for 1 hr. the precipitate is separated by filtration and the filtrate is dried (MgSO₄). Removed of the solvent by evaporation yield the title compound, nmr (DMSO-d₆) δ1.18 (t, 3H), 1.62 (s, 3H), 2.80 (t, 2H), identical to the product of Example 319.

The corresponding hydrochloric acid addition salt, 1-[(ethylamino)methyl]-1-methyl-1,3,4,9-tetrahydropyrano[3,4-b]indole hydrochloride, has m.p. 242° - 243° C., after recrystallization from isopropanol-ether.

By following the procedure of Example 782 but using as starting material an equivalent amount of the appropriate starting material of formula II, for example, those described in Examples 1 to 125, and using an equivalent amount of an appropriate ketoamide of formula

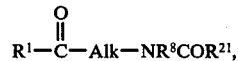

described above, then the respective secondary amine compounds of formula I are obtained.

EXAMPLE 783

1-METHYL-1-NITROMETHYL-1,3,4,9-TETRAHYDROPYRANO[3,4-b]INDOLE (VII; $R^1$ = CH₃, $R^2$, $R^3$, $R^4$, $R^5$, $R^6$ AND $R^7 = H$, $X = O$ and $Z = CH_2NO_2$ To a solution of 322 mg of tryptophol (II, $R^2$, $R^3$, $R^4$, $R^5$, $R^6$ = H and $X^1$=OH) and 248 mg of the nitroketone, nitro-2-propanone, in 100 ml of benzene is added five drops of boron trifluoride etherate and three drops of trifluoroacetic acid. The reaction mixture is stirred and heated at reflux under water-separator for 18 hr. The benzene solution is cooled, washed with 10% sodium bicarbonate solution, water, saturated brine solution, and dried over magnesium sulfate. The solvent is removed and the residue is subjected to chromatography on silica gel. Elution with chloroform gives the title compound, $\delta_{max}^{CHCl_3}$ 3450, 1550cm³¹ ¹, nmr (CDCl₃) δ1.68 (s, 3H), 2.84 (t, 2H), 4.10 (t, 2H).

Reduction of the latter compound with lithium aluminum hydride according to the procedure of Example 309 affords 1-(aminomethyl)-1-methyl-1,3,4,9-tetrahydropyrano[3,4-b]indole, identical with the product of Example 316.

By following the procedure of Example 783 but using as starting material an equivalent amount of the appropriate starting material of formula II, for example, those described in Examples 1 to 125, and using an equivalent amount of an appropriate nitroketone of formula

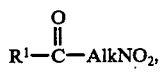
$R^1-C-AlkNO_2$, described above, then the respective primary amine compounds of formula I are obtained.

EXAMPLE 784

6-HYDROXY-1-METHYL-1,3,4,9-TETRAHYDROPYRANO[3,4-b]INDOLE-1-ACETIC ACID (VII; $R^1$ = $CH_3$, $R^2$, $R^3$, $R^4$, $R^5$ AND $R^7$ = H, $R^6$ = 6-OH, X = O, AND Z = $CH_2COOH$)

A mixture of 6-benzyloxy-1-methyl-1,3,4,9-tetrahydropyrano[3,4-b]indole-1-acetic acid (5.3 g., 0.015 mole), prepared as described in Example 25, in 250 ml. of anhydrous ethanol, and 1.1 g of 10% palladium on carbon is stirred at room temperature under a hydrogen atmosphere until no more hydrogen is being taken up by the reaction mixture. The catalyst is removed by filtration through diatomaceous earth (Celite) and the filtrate concentrated. The residue is recrystallized from ethanol-benzene to afford the title compound, m.p. 170° – 171° C.

The corresponding benzylamine salt is prepared by the mixing of equimolar ethereal solutions of benzylamine and the above product. The resulting solid is recrystallized from acetonitrile to afford 6-hydroxy-1-methyl-1,3,4,9-tetrahydropyrano[3,4-b]indole-1-acetic acid benzylamine salt, m.p. 191° – 193° C. The corresponding acetate is prepared by allowing a mixture of the title compound and a five molar excess of acetic anhydride in pyridine solution to stand for 24 hr. Dilution of the mixture with water extraction with ether and recrystallization of the extract residue from benzene-petroleum ether, affords 6-acetoxy-1-methyl-1,3,4,9-tetrahydro[3,4-b]indole-1-acetic acid, identical with the product of Example 24.

EXAMPLE 785

1,1-DIMETHYL-1,3,4,9-TETRAHYDROPYRANO[3,4-b]INDOLE (VII; $R^1$ = $CH_3$, $R^2$, $R^3$, $R^4$, $R^5$, $R^6$, AND $R^7$ = H AND Z = $CH_3$)

A solution of tryptophol (8 g, 0.05M), acetone (5 g) and p-toluenesulfonic acid (100 mg) in 100 ml of benzene containing hydrated alkali-aluminium silicate (Molecular Sieves No. 4) is heated to reflux for 1 hr. More p-toluenesulfonic acid (100 mg) and the ketone, acetone (3 g), is added and the reflux continued for a further 1.5 hr.

The mixture is filtered and the filtrate is washed with 5% sodium bicarbonate and water. After drying over sodium sulfate the benzene is evaporated under reduced pressure affording a solid. Chromatography of this solid on silica gel using 30% ethyl acetate in benzene as eluant gives a white product which is recrystallized once from benzene-petroleum ether to give the title compound, m.p. 142° – 144° C., nmr ($CDCl_3$) δ2.76 (t, J = 5.5 cps, 2H), 4.03 (t, J = 5.5 cps, 2H).

The procedure of Example 785 is followed to prepare other compounds of formula VII in which $R^1$, $R^2$, $R^3$, $R^4$, $R^5$, $R^6$ are as defined in the first instance, $R^7$ is hydrogen and Z is lower alkyl or phenyl(lower)alkyl. Examples of such compounds are listed in Tables XVII and XVIII. In each example an equivalent amount of the starting material of formula II listed therein is used instead of the starting material of formula II described in Example 785, together with the appropriate ketone.

TABLE XVII

| EX. | STARTING MATERIAL OF FORMULA II | | | | | | KETONE OF FORMULA $R^1-C-Z$ | | PRODUCT: (PREFIX LISTED BELOW)-1,3,4,9-TETRAHYDROPYRANO-[3,4-b]-INDOLE |
|---|---|---|---|---|---|---|---|---|---|
| | $R^2$ | $R^3$ | $R^4$ | $R^5$ | $R^6$ | X | $R^1$ | Z | |
| 786 | H | H | H | H | H | O | $C_2H_5$ | n-$C_3H_7$ | 1-ethyl-1-propyl |
| 787 | H | H | H | H | H | O | $CH_3$ | n-$C_3H_7$ | 1-methyl-1-propyl |
| 788 | H | H | H | H | H | O | $C_2H_5$ | ⌬-(CH$_2$)$_2$ | 1-ethyl-1-phenethyl |
| 789 | H | H | H | H | H | O | $CH_3$ | ⌬-CH$_2$ | 1-benzyl-1-methyl, m.p. 141–145° C |
| 790 | $CH_3$ | H | H | H | H | O | $CH_3$ | $CH_3$ | 1,1,3-trimethyl |
| 791 | n-$C_3H_7$ | H | H | H | H | O | $CH_3$ | n-$C_3H_7$ | 1,3-dipropyl-1-methyl |
| 792 | $CH_3$ | $CH_3$ | H | H | H | O | ▷ | $CH_3$ | 1-cyclopropyl-1,3,3-trimethyl |
| 793 | $C_2H_5$ | H | $C_2H_5$ | H | H | O | ◯ | n-$C_3H_7$ | 1-cyclohexyl-3,4-diethyl-1-propyl |
| 794 | H | H | $CH_3$ | n-$C_3H_7$ | H | O | $CH_3$ | n-$C_3H_7$ | 1,4-dimethyl-1,4-dipropyl |
| 795 | $CH_3$ | $CH_3$ | $CH_3$ | $CH_3$ | H | O | $CH_3$ | ⌬-CH$_2$ | 1-benzyl-1,3,3,4,4-pentamethyl |
| 796 | H | H | H | H | 4-$CH_3$ | O | △ | $CH_3$ | 1-cyclopropyl-1,5-dimethyl |
| 797 | H | H | H | H | 5-$C_2H_5$ | O | ⌂ | | 1-cyclopentyl-6-ethyl |
| 798 | $C_2H_5$ | H | H | H | 6-$OCH_3$ | O | $C_2H_5$ | $C_2H_5$ | 7-methoxy-1,1,3-triethyl |
| 799 | $CH_3$ | $CH_3$ | H | H | 7-$OC_2H_5$ | O | $CH_3$ | $CH_3$ | 8-ethoxy-1,1,3,3-tetramethyl |
| 800 | $C_2H_5$ | H | H | H | 5-$NO_2$ | O | $C_2H_5$ | ⌬-(CH$_2$)$_3$ | 1,3-diethyl-6-nitro-1-(3-phenylpropyl) |
| 801 | H | H | H | H | 7-$NO_2$ | O | $CH_3$ | $CH_3$ | 1,1-dimethyl-8-nitro |
| 802 | H | H | H | $CH_3$ | 6-$CH_3COO$ | O | $C_2H_5$ | $CH_3$ | 7-acetoxy-1,4-dimethyl-1-ethyl |
| 803 | n-$C_3H_7$ | n-$C_3H_7$ | H | H | 5-$C_2H_5COO$ | O | △ | ⌬-CH$_2$ | 1-benzyl-1-cyclopropyl-3,3-dipropyl-6-propionyloxy |

TABLE XVII-continued

| EX. | STARTING MATERIAL OF FORMULA II | | | | | | KETONE OF FORMULA $R^1-\overset{\overset{\text{O}}{\|}}{C}-Z$ | | PRODUCT: (PREFIX LISTED BELOW)-1,3,4,9-TETRAHYDROPYRANO-[3,4-b]-INDOLE |
|---|---|---|---|---|---|---|---|---|---|
| | $R^2$ | $R^3$ | $R^4$ | $R^5$ | $R^6$ | X | $R^1$ | Z | |
| 804 | H | H | H | H | 4-Cl | O |  | $CH_3$ | 5-chloro-1-cyclopropyl-methyl |
| 805 | $CH_3$ | H | H | H | 6-Cl | O | 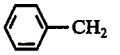 | —$CH_2$ | 1-benzyl-7-chloro-1-cyclohexyl-3-methyl |
| 806 | $C_2H_5$ | H | H | H | 5-Br | O | $C_2H_5$ | $C_2H_5$ | 6-bromo-1,1,3-triethyl |
| 807 | H | H | $n-C_3H_7$ | $n-C_3H_7$ | 7-Br | O | $n-C_3H_7$ | $CH_3$ | 8-bromo-1-methyl-1,4,4-tripropyl |
| 808 | $CH_3$ | $CH_3$ | $CH_3$ | $CH_3$ | 4-F | O | $CH_3$ | $CH_3$ | 5-fluoro-1,1,3,3,4,4-hexamethyl |
| 809 | H | H | H | H | 6-F | O | 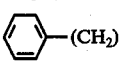 | $n-C_3H_7$ | 1-cyclopropyl-7-fluoro-1-propyl |
| 810 | $CH_3$ | H | $CH_3$ | H | 7-I | O | $CH_3$ | 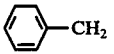—$(CH_2)$ | 8-iodo-1-phenethyl-1,3,4-trimethyl |
| 811 | H | H | H | H | 5-I | O | $CH_3$ | $CH_3$ | 1,1-dimethyl-6-iodo |

TABLE XVIII

| EX. | STARTING MATERIAL OF FORMULA II | | | | | | KETONE OF FORMULA $R^1-\overset{\overset{\text{O}}{\|}}{C}-Z$ | | PRODUCT: (PREFIX LISTED BELOW)-1,3,4,9-TETRAHYDROTHIOPYRANO-[3,4-b]INDOLE |
|---|---|---|---|---|---|---|---|---|---|
| | $R^2$ | $R^3$ | $R^4$ | $R^5$ | $R^6$ | X | $R^1$ | Z | |
| 812 | H | H | H | H | H | S | $CH_3$ | $CH_3$ | 1,1-dimethyl |
| 813 | H | H | H | H | H | S | $CH_3$ | $n-C_3H_7$ | 1-methyl-1-propyl |
| 814 | H | H | H | H | H | S | $C_2H_5$ | —$(CH_2)_2$ | 1-ethyl-1-phenethyl |
| 815 | H | H | H | H | H | S | $CH_3$ | 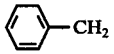—$CH_2$ | 1-benzyl-1-methyl |
| 816 | $CH_3$ | H | H | H | H | S | $CH_3$ | $CH_3$ | 1,1,3-trimethyl |
| 817 | $n-C_3H_7$ | H | H | H | H | S | $CH_3$ | $n-C_3H_7$ | 1,3-dipropyl-1-methyl |
| 818 | $CH_3$ | H | H | H | H | S |  | $CH_3$ | 1-cyclopropyl-1,3,3,-trimethyl |
| 819 | $C_2H_5$ | H | $C_2H_5$ | H | H | S | 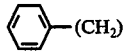 | $n-C_3H_7$ | 1-cyclohexyl-3,4-diethyl-1-propyl |
| 820 | H | H | $CH_3$ | $n-C_3H_7$ | H | S | $CH_3$ | $n-C_3H_7$ | 1,4-dimethyl-1,4-dipropyl |
| 821 | $CH_3$ | $CH_3$ | $CH_3$ | $CH_3$ | H | S | $CH_3$ | —$CH_2$ | 1-benzyl-methyl-1,3,3,4,4-pentamethyl |
| 822 | H | H | H | H | 4-$CH_3$ | S |  | $CH_3$ | 1-cyclopropyl-1,5-dimethyl |
| 823 | H | H | H | H | 5-$C_2H_5$ | S | 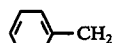 | | 1-cyclopentyl-6-ethyl |
| 824 | $C_2H_5$ | H | H | H | 6-$OCH_3$ | S | $C_2H_5$ | $C_2H_5$ | 7-methoxy-1,1,3-triethyl |
| 825 | $CH_3$ | $CH_3$ | H | H | 7-$OC_2H_5$ | S | $CH_3$ | $CH_3$ | 8-ethoxy-1,1,3,3-tetramethyl |
| 826 | $C_2H_5$ | H | H | H | 5-$NO_2$ | S | $C_2H_5$ | 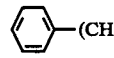—$(CH_2)_3$ | 1,3-diethyl-6-nitro-1-(3-phenylpropyl) |
| 827 | H | H | H | H | 7-$NO_2$ | S | $CH_3$ | $CH_3$ | 1,1-dimethyl-8-nitro |
| 828 | H | H | H | $CH_3$ | 6-$CH_3COO$ | S | $C_2H_5$ | $CH_3$ | 7-acetoxy-1,4-dimethyl-1-ethyl |
| 829 | $n-C_3H_7$ | $n-C_3H_7$ | H | H | 5-$C_2H_5COO$ | S | △ | ⬡$CH_2$ | 1-benzyl-1-cyclopropyl-3,3-dipropyl-6-propionyloxy |
| 830 | H | H | H | H | 4-Cl | S | △ | $CH_3$ | 5-chloro-1-cyclopropyl-1-methyl |
| 831 | $CH_3$ | H | H | H | 6-Cl | S | ⬡ | ⬡$CH_2$ | 1-benzyl-7-chloro-1-cyclohexyl-3-methyl |
| 832 | $C_2H_5$ | H | H | H | 5-Br | S | $C_2H_5$ | $C_2H_5$ | 6-bromo-1,1,3-triethyl |
| 833 | H | H | $n-C_3H_7$ | $n-C_3H_7$ | 7-Br | S | $n-C_3H_7$ | $CH_3$ | 8-bromo-1-methyl-1,4,4-tripropyl |
| 834 | $CH_3$ | $CH_3$ | $CH_3$ | $CH_3$ | 4-F | S | $CH_3$ | $CH_3$ | 5-fluoro-1,1,3,3,4,4-hexamethyl |
| 835 | H | H | H | H | 6-F | S | △ | $n-C_3H_7$ | 1-cyclopropyl-7-fluoro-1-propyl |
| 836 | $CH_3$ | H | $CH_3$ | H | 7-I | S | $CH_3$ | ⬡—$(CH_2)$ | 8-iodo-1-phenethyl-1,3,4-trimethyl |
| 837 | H | H | H | H | 5-I | S | $CH_3$ | $CH_3$ | 1,1-dimethyl-6-iodo |

EXAMPLE 838

1,1-DIMETHYL-9-[2-(DIMETHYLAMINO)ETHYL]-1,3,4,9-TETRAHYDROPYRANO[3,4-b]INDOLE (I; $R^1$ AND Y = $CH_3$, $R^2$, $R^3$, $R^4$, $R^5$ AND $R^6$ = H, AND $R^7$ = $CH_2CH_2N(CH_3)_2$]

To 4.2 g. of a 50% dispersion of sodium hydride in 20 ml. of dimethylformamide is added a solution of 7 g. of 1,1-dimethyl-1,3,4,9-tetrahydropyrano[3,4-b]indole, described in Example 785, in 20 ml. of dimethylformamide. The addition is made dropwise at room temperature while stirring vigorously. The mixture is heated for 1 hr. at 40° C. Then an excess of the organic halide, dimethylaminoethyl chloride (free base obtained from 15 g. of the hydrochloride) is added and stirring continued at 40° C overnight.

The reaction mixture is poured into ice-water, acidified with 6NHCl and washed with ether. The aqueous phase is rendered alkaline with 10% NaOH and extracted with benzene. The organic phase is washed with water, dried over sodium sulfate, and evaporated under reduced pressure to yield the title compound, nmr ($CDCl_3$) $\delta$1.63 (6H), 2.36 (6H), 2.79 (m, 4H), 4.10 (m, 4H), 7.18 (m, 4H).

The corresponding hydrochloric acid addition salt, 1,1-dimethyl-9-[(2-(dimethylamino)ethyl]-1,3,4,9-tetrahydropyrano[3,4-b]indole hydrochloride, has m.p. 198° – 200° C., after crystallization from methanol-ether.

The procedure of Example 838 is followed to prepare other compounds of formula I in which $R^1$, $R^2$, $R^3$, $R^4$, $R^5$, $R^6$ and X are as defined in the first instance, $R^7$ is aminoalkyl as defined above and Y is lower alkyl or phenyl(lower)alkyl. Examples of such compounds are listed in Tables XIX and XX. In each example an equivalent amount of the appropriate starting material of formula VII in which $R^1$, $R^2$, $R^3$, $R^4$, $R^5$, $R^6$ are as defined in the first instance, $R^7$ is hydrogen and Z is lower alkyl or phenyl(lower)alkyl, described in Examples 785 to 837, is used in place of 1,1-dimethyl-1,3,4,9-tetrahydropyrano[3,4-b]indole if required. In each case the starting material of formula VII is noted by the example in which it is prepared.

TABLE XIX

| EXAMPLE | NO. OF THE EXAMPLE IN WHICH STARTING MATERIAL IS PREPARED | ORGANIC HALIDE | PRODUCT: (PREFIX LISTED BELOW)-1,3,4,9-TETRAHYDROPYRANO-[3,4-b]INDOLE |
|---|---|---|---|
| 839 | 785 | $(CH_3)_2N(CH_2)_3Cl$ | 1,1-dimethyl-9-[3-(dimethylamino)propyl], nmr ($CDCl_3$) $\delta$1.62 (6H), 2.00 (m, 2H), 2.25 (6H), corresponding hydrochloric acid addition salt has m.p. 201 – 203° C. |
| 840 | 785 | $CH_3NH(CH_2)_2Cl$ | 1,1-dimethyl-9-[2-(methylamino)ethyl] |
| 841 | 785 | i-$C_3H_7NH(CH_2)_2Cl$ | 1,1-dimethyl-9-[2-(isopropylamino)ethyl] |
| 842 | 786 | $NH_2CH_2C(CH_3)_2CH_2Br$ | 9-(3-amino-2,2-dimethylethyl)-1-ethyl-1-propyl |
| 843 | 787 | $(CH_3)_2N(CH_2)_2Cl$ | 9-[2-(dimethylamino)ethyl]-1-methyl-1-propyl |
| 844 | 788 | $C_2H_5NH(CH_2)_3Cl$ | 1-ethyl-9-[3-(ethylamino)propyl]-1-phenethyl |
| 845 | 789 | $(CH_3)_2N(CH_2)_2Cl$ | 1-benzyl-9-[2-(dimethylamino)ethyl]-1-methyl, nmr($CDCl_3$) $\delta$1.55 (s, 3H), 2.92 (6H), 3.95 (2H), corresponding hydrochloric acid addition salt has m.p. 218 – 220° C. |
| 846 | 789 | $CH_3NH(CH_2)_2Cl$ | 1-benzyl-1-methyl-9-[2-(methylamino)ethyl] |
| 847 | 789 | $NH_2(CH_2)_3Cl$ | 9-(4-aminobutyl)-1-benzyl-1-methyl |
| 848 | 790 | $(CH_3)_2NCH_2[CH(CH_3)]_2Cl$ | 9-[1,2-dimethyl-3-(dimethylamino)propyl]-1,1,3-trimethyl |
| 849 | 791 | $(C_2H_5)_2NCH(C_2H_5)CH_2Cl$ | 9-[2-(diethylamino)-2-ethylethyl]-1,3-dipropyl-1-methyl |
| 850 | 792 | $CH_3NH(CH_2)_3Cl$ | 1-cyclopropyl-9-[3-(methylamino)propyl]-1,3,3-trimethyl |
| 851 | 793 | $(CH_3)_2N(CH_2)_2Cl$ | 1-cyclohexyl-3,4-diethyl-9-[2-(dimethylamino)ethyl]-1-propyl |
| 852 | 794 | $(n-C_3H_7)_2N(CH_2)_3Cl$ | 1,4-dimethyl-1,4-dipropyl-9-[3-(dipropylamino)propyl] |
| 853 | 795 | $(CH_3)_2NCH(n-C_3H_7)CH_2Cl$ | 1-benzyl-9-[2-(dimethylamino)-2-propylethyl]-1,3,3,4,4-pentamethyl |
| 854 | 796 | $(CH_3)_2N[CH(n-C_3H_7)]_3CH_2Cl$ | 1-cyclopropyl-1,5-dimethyl-9-[4-(dimethylamino)-2,3,4-tripropylbutyl] |
| 855 | 797 | $(C_2H_5)_2N(CH_2)_2Cl$ | 1-cyclopentyl-9-[2-(diethylamino)ethyl]-6-ethyl |
| 856 | 798 | $CH_3NH(CH_2)_3Cl$ | 7-methoxy-9-[3-(methylamino)propyl]-1,1,3-triethyl |
| 857 | 799 | n-$C_3H_7NH(CH_2)_2Cl$ | 8-ethoxy-9-[2-(propylamino)ethyl]-1,1,3,3-tetramethyl |
| 858 | 800 | i-$C_3H_7NH(CH_2)_2Cl$ | 1,3-diethyl-9-[2-(isopropylamino)ethyl]-6-nitro-1-(3-phenylpropyl) |
| 859 | 801 | $(CH_3)_2N(CH_2)_2Cl$ | 1,1-dimethyl-9-[2-(dimethylamino)ethyl]-8-nitro |
| 860 | 802 | $C_2H_5NH(CH_2)_3Cl$ | 7-acetoxy-1,4-dimethyl-1-ethyl-9-[3-(ethylamino)propyl] |

TABLE XIX-continued

| EXAMPLE | NO. OF THE EXAMPLE IN WHICH STARTING MATERIAL IS PREPARED | ORGANIC HALIDE | PRODUCT: (PREFIX LISTED BELOW)-1,3,4,9-TETRAHYDROPYRANO-[3,4-b]INDOLE |
|---|---|---|---|
| 861 | 803 | $(CH_3)_2N(CH_2)_2Cl$ | 1-benzyl-1-cyclopropyl-9-[2-(dimethylamino)ethyl-3,3-dipropyl-6-propionyloxy |
| 862 | 804 | $n-C_3H_7NH(CH_2)_3Cl$ | 5-chloro-1-cyclopropyl-1-methyl-9-[3-(propylamino)-propyl |
| 863 | 805 | 1-(3-chloropropyl)-pyrrolidine | 1-benzyl-7-chloro-1-cyclohexyl-3-methyl-9-[3-(lpyrrolidinyl)-propyl] |
| 864 | 806 | 1-(2-chloroethyl)-piperidine | 6-bromo-9-(2-piperidinoethyl)-1,1,3-triethyl |
| 865 | 807 | 4-(2-chloroethyl)-morpoline | 8-bromo-1-methyl-9-(2-morpholino-ethyl)-1,4,4-tripropyl |
| 866 | 808 | 1-(3-chloropropyl)-piperazine | 5-fluoro-1,1,3,3,4,4-hexamethyl-9-(piperazinopropyl) |
| 867 | 809 | 1-(3-chloroethyl)-4-methylpiperazine | 1-cyclopropyl-7-fluoro-9-[2-(4-methyl-1-piperazinyl)-ethyl]-1-propyl |
| 868 | 810 | 1-(2-chloroethyl)-4-(hydroethyl)piperazine | 9-{2-[4-(hydroxyethyl)-1-piperazinyl]ethyl-8-iodo-1-phenethyl-1,3,4-trimethyl |
| 869 | 811 | 1-(2-chloroethyl)-pyrrolidine | 1,1-dimethyl-6-iodo-9-[2-(1-pyrrolidinyl)ethyl] |
| 870 | 785 | 1-(3-chloropropyl)-piperidine | 1,1-dimethyl-9-(3-piperidino-propyl) |
| 871 | 785 | 4-(4-chlorobutyl)-morpholine | 1,1-dimethyl-9-(4-morpholino-butyl) |
| 872 | 789 | 1-(4-chlorobutyl)-4-methylpiperazine | 9-[4-(4-methyl-1-piperazinyl)-butyl] |
| 873 | 789 | 1-(2-chloroethyl)-4-(3-hydroxypropyl)-piperazine | 1-benzyl-9-{2-[4-(hydroxypropyl)-1-piperazinyl]ethyl}-1-methyl |

TABLE XX

| EXAMPLE | NO. OF EXAMPLE IN WHICH STARTING MATERIAL IS PREPARED | ORGANIC HALIDE | PRODUCT: (PREFIX LISTED BELOW)-1,3,4,9-TETRAHYDROTHIOPYRANO[3,4-b]INDOLE |
|---|---|---|---|
| 874 | 812 | $(CH_3)_2N(CH_2)_3Cl$ | 1,1-dimethyl-9-[3-(dimethyl-amino)propyl] |
| 875 | 812 | $CH_3NH(CH_2)_2Cl$ | 1,1-dimethyl-9-[2-(methylamino)-ethyl] |
| 876 | 812 | $i-C_3H_7NH(CH_2)_2Cl$ | 1,1-dimethyl-9-[2-(isopropyl-amino)ethyl] |
| 877 | 812 | $NH_2CH_2C(CH_3)_2CH_2Br$ | 9-(3-amino-2,2-dimethylethyl)-1,1-dimethyl |
| 878 | 813 | $(CH_3)_2N(CH_2)_2Cl$ | 9-[2-(dimethylamino)ethyl]-1-methyl-1-propyl |
| 879 | 814 | $C_2H_5NH(CH_2)_3Cl$ | 1-ethyl-9-[3-(ethylamino)propyl]-1-phenethyl |
| 880 | 815 | $(CH_3)_2N(CH_2)_2Cl$ | 1-benzyl-9-[2-(dimethylamino)-ethyl]-1-methyl |
| 881 | 815 | $CH_3NH(CH_2)_2Cl$ | 1-benzyl-1-methyl-9-[2-(methyl-amino)ethyl] |
| 882 | 815 | $NH_2(CH_2)_3Cl$ | 9-(4-aminobutyl)-1-benzyl-1-methyl |
| 883 | 816 | $(CH_3)_2NCH_2[CH(CH_3)]_2Cl$ | 9-[1,2-dimethyl-3-(dimethyl-amino)propyl]-1,1,3-trimethyl |
| 884 | 817 | $(C_2H_5)_2NCH(C_2H_5)CH_2Cl$ | 9-[2-(diethylamino)-2-ethyl-ethyl]-1,3-dipropyl-1-methyl |
| 885 | 818 | $CH_3NH(CH_2)_3Cl$ | 1-cyclopropyl-9-[3-(methyl-amino)propyl]-1,3,3-trimethyl |
| 886 | 819 | $(CH_3)_2N(CH_2)_2Cl$ | 1-cyclohexyl-3,4-diethyl-9-[2-(dimethylamino)ethyl]-1-propyl |
| 887 | 820 | $(n-C_3H_7)_2N(CH_2)_3Cl$ | 1,4-dimethyl-1,4-dipropyl-9-[3-(dipropylamino)propyl] |
| 888 | 821 | $(CH_3)_2NCH(n-C_3H_7)CH_2Cl$ | 1-benzyl-9-[2-(dimethylamino)-2-propylethyl]-1,3,3,4,4-pentamethyl |
| 889 | 822 | $(CH_3)_2N[CH(n-C_3H_7)]_3CH_2Cl$ | 1-cyclopropyl-1,5-dimethyl-9-[4-(dimethylamino)-2,3,4-tripropylbutyl] |
| 890 | 823 | $(C_2H_5)_2N(CH_2)_2Cl$ | 1-cyclopentyl-9-[2-(diethyl-amino)ethyl]-6-ethyl |
| 891 | 824 | $CH_3NH(CH_2)_3Cl$ | 7-methoxy-9-[3-(methylamino)-propyl]-1,1,3-triethyl |
| 892 | 825 | $n-C_3H_7NH(CH_2)_2Cl$ | 8-ethoxy-9-[2-(propylamino)-ethyl]-1,1,3,3-tetramethyl |
| 893 | 826 | $i-C_3H_7NH(CH_2)_2Cl$ | 1,3-diethyl-9-[2-(isopropyl-amino)ethyl]-6-nitro-1-(3-phenylpropyl) |
| 894 | 827 | $(CH_3)_2N(CH_2)_2Cl$ | 1,1-dimethyl-9-[2-(dimethyl- |

TABLE XX-continued

| EXAMPLE | NO. OF EXAMPLE IN WHICH STARTING MATERIAL IS PREPARED | ORGANIC HALIDE | PRODUCT: (PREFIX LISTED BELOW)-1,3,4,9-TETRAHYDROTHIOPYRANO[3,4-b]INDOLE |
|---|---|---|---|
| 895 | 828 | $C_2H_5NH(CH_2)_3Cl$ | amino)ethyl]-8-nitro 7-acetoxy-1,4-dimethyl-1-ethyl-9-[3-(ethylamino)propyl] |
| 896 | 829 | $(CH_3)_2N(CH_2)_2Cl$ | 1-benzyl-1-cyclopropyl-9-[2-(dimethylamino)ethyl]-3,3-dipropyl-6-propionyloxy |
| 897 | 830 | $n-C_3H_7NH(CH_2)_3Cl$ | 5-chloro-1-cyclopropyl-1-methyl-9-[3-(propylamino)propyl] |
| 898 | 831 | 1-(3-chloropropyl)-pyrrolidine | 1-benzyl-7-chloro-1-cyclohexyl-3-methyl-9-[3-(1-pyrrolidinyl)-propyl] |
| 899 | 832 | 1-(2-chloroethyl)-piperidine | 6-bromo-9-(2-piperidinoethyl)-1,1,3-triethyl |
| 900 | 833 | 4-(2-chloroethyl)-morpholine | 8-bromo-1-methyl-9-(2-morpholino-ethyl)-1,4,4-tripropyl |
| 901 | 834 | 1-(3-chloropropyl)-piperazine | 5-fluoro-1,1,3,3,4,4-hexamethyl-9-(piperazinopropyl) |
| 902 | 835 | 1-(3-chloroethyl)-4-methylpiperazine | 1-cyclopropyl-7-fluoro-9-[2-(4-methyl-1-piperazinyl)-ethyl]-1-propyl |
| 903 | 836 | 1-(2-chloroethyl)-4-(hydroethyl)-piperazine | 9-{2-[4-(hydroxyethyl)-1-piperazinyl]ethyl}ethyl-8-iodo-1-phenethyl-1,3,4-trimethyl |
| 904 | 837 | 1-(2-chloroethyl)-pyrrolidine | 1,1-dimethyl-6-iodo-9-[2-(1-pyrrolidinyl)ethyl] |
| 905 | 812 | 1-(3-chloropropyl)-piperidine | 1,1-dimethyl-9-(3-piperidinopropyl) |
| 906 | 812 | 4-(4-chlorobutyl)-morpholine | 1,1-dimethyl-9-(4-morpholino-butyl) |
| 907 | 815 | 1-(4-chlorobutyl)-4-methylpiperazine | 1-benzyl-1-methyl-9-[4-(4-methyl-1-piperazinyl)butyl] |
| 908 | 815 | 1-(2-chloroethyl)-4-(3-hydroxypropyl)-piperazine | 1-benzyl-9-{2-[4-(hydroxypropyl)-1-piperazinyl]ethyl}-1-methyl |

EXAMPLE 909

1,1-DIMETHYL-9-[2-(DIMETHYLAMINO)ETHYL]-1,3,4,9-TETRAHYDROPYRANO[3,4-b]INDOLE-6-OL [I, $R^1$ and $Y = CH_3$, $R^2$, $R^3$, $R^4$ AND $R^5 = H$, $R^6 = OH$ AND $R^7 = CH_2CH_2N(CH_3)_2$]

5-Benzyloxy-3-tryptophol (II; $R^2$, $R^3$, $R^4$ and $R^5 = H$, $R^6 = $ 5-benzyloxy and $X^1 = OH$), m.p. 93° – 95° C., is prepared by lithium aluinum hydride reduction of ethyl 5-benzyloxy-3-indoleglyoxalate (British Patent 778,823) according to the procedure of Example 309. Subsequent treatment of 5-benzyloxy-3-tryptophol with the ketone, acetone, according to the procedure of Example 785 affords 6-benzyloxy-1,1-dimethyl-1,3,4,9-tetrahydropyrano[3,4-b]indole (VIII $R^1$ M $CH_3$), nmr ($CDCl_3$) $\delta 1.53$ (6H), 2.73 (t, 2H), 4.03 (t, 2H), 5.10 (2H), 6.67 – 7.83 (9H). The latter compound is then N-alkylated with the organic halide, dimethylaminoethyl chloride, according to the procedure of Example 838 to afford 6-benzyloxy-1,1-dimethyl-9-[2-(dimethylamino)ethyl]-1,3,4,9-tetrahydropyrano[3,4-b]indole, which on treatment with hydrochloric acid gives the corresponding hydrochloric acid addition salt thereof, m.p. 209° C.

The latter compound, 6-benzyloxy-1,1-dimethyl-9-[2-(dimethylamino)ethyl]-1,3,4,9-tetrahydropyrano[3,4-b]indole hydrochloride (11.5 g., 0.028M) in 600 ml. of absolute ethanol and 600 mg of 10% palladium on carbon is stirred at room temperature under a hydrogen atmosphere for 22 hr. until no more hydrogen is taken up by the reaction. The catalyst is collected on celite and the filtrate concentrated to afford the corresponding hydrochloric acid addition salt of the title compound, m.p. 225° – 228° C., after recrystallization from ethanol-ether.

The title compound [free base, nmr ($CDCl_3$) $\delta 1.61$ (6H), 2.57 (t, J = 5 cps, 2H), 3.86 (t, J = 5 cps, 2H)] is obtained by decomposing the hydrochloric acid addition salt, for example, by washing a chloroform solution of the salt with 10% sodium hydroxide solution and evaporating the solvent.

By replacing 5-benzyloxy-3-tryptophol with an equivalent amount of 7-benzyloxy-3-tryptophol in the procedure of this example 1,1-dimethyl-9-[2-(dimethylamino)ethyl]-1,3,4,9-tetrahydropyrano[3,4-b]indole-8-ol is obtained.

EXAMPLE 910

1-(2-AMINOETHYL)-1-METHYL-1,3,4,9-TETRAHYDROPYRANO[3,4-b]INDOLE (I; $R^1 = CH_3$, $R^2$, $R^3$, $R^4$, $R^5$, $R^6$ AND $R^7 = H$, X, O and $Y = CH_2NH_2$)

1-Methyl-1,3,4,9-tetrahydropyrano[3,4-b]indole-1-acetamide (20.0 g., 0.817 mole), described in Example 126, is dissolved in dry methylene chloride (400 ml) and freshly prepared triethyloxonium fluoroborate (17.00 g., 0.894 mole) is added in one portion to the solution. The reaction mixture is stirred at room temperature for 2 hr.. The methylene chloride solution is washed with cold 75% aqueous potassium carbonate followed by brine and the dried organic layer is concentrated under reduced pressure. The residue is dissolved in ether (150 ml.). The solution is filtered and crystallization proceeds at room temperature to afford ethyl-1-methyl-1,3,4,9-tetrahydropyrano[3,4b]indole-1-acetimidate, m.p. 139.5° – 141° C.

The latter compound (4.79 g., 0.0176 mole) dissolved in dry THF (100 ml.) is added dropwise to a stirred and ice-cooled suspension of lithium aluminum hydride (1.75 g., 0.046 mole) in THF (50 ml.). The reaction mixture is stirred overnight at room temperature and then dilute sodium hydroxide is added dropwise to decompose excess hydride. The precipitate is collected by filtration and the filtrate is concentrated under reduced pressure thus affording a residue which is extracted with methylene chloride. The organic layers are washed with brine, dried (MgSO₄) and concentration of the solvent and crystallization from ether affords the title compound, m.p. 80° - 84° C., $\delta_{max}^{CHCl_3}$ 3455, 3280 cm⁻¹, identical with the compound of the same name described in Example 309.

EXAMPLE 911

1-[2-(DIMETHYLAMINO)ETHYL]-9-ETHYL-1-METHYL-1,3,4,9-TETRAHYDROTHIOPYRANO[3,4-b]INDOLE [I; $R^1$ = CH₃, $R^2$, $R^3$, $R^4$, $R^5$, AND $R^6$ = H, X = S AND Y = CH₂CH₂N(CH₃)₂]

The compound of formula I in which $R^7$ = H and Y = amino(lower)alkyl,1-[2-(dimethylamino)ethyl]-1-methyl-1,3,4,9-tetrahydrothiopyrano[3,4-b]indole (822 mg), described in Example 398, is dissolved in 15 ml of DMF and 15 ml of benzene. To remove all possible traces of water, a portion of this benzene is distilled. After cooling to 0°, 140 mg of sodium hydride (54% suspension in mineral oil) is added, and the mixture stirred for 15 min. Alkylation is accomplished by addition of 350 mg of ethyl bromide and stirring the reaction mixture at 0° for 20 min. The resulting suspension is poured onto cracked ice, extracted with chloroform, the organic layer washed repeatedly with water and evaporated. Chromatography of the residue on silica gel (20 g) using chloroform-methanol (0–10%) affords the title compound, which after crystallization from ether hexane has m.p. 86° - 88° C., $\delta_{max}^{CHCl_3}$ 2820, 2765, 1600, 1568, 1537 cm⁻¹, nmr (CDCl₃) δ2.20 (s, 6H), 2.30 (m, 4H).

The corresponding hydrochloric acid addition salt of the title compound, 1-[2-(dimethylamino)ethyl]-9-ethyl-1-methyl-1,3,4,9-tetrahydrothiopyrano[3,4-b]indole hydrochloride, has m.p. 220° - 222° C.

By following the procedure of Example 911 and using an appropriate compound of formula I in which $R^7$ is hydrogen and Y is an amino(lower)alkyl, for instance those described in Example 309 to 487, together with the appropriate organic halide, then other compounds of formula I in which $R^7$ is lower alkyl, lower alkenyl, propargyl, phenyl(lower)alkyl or amino(lower)alkyl are obtained.

For example, the use of the same compound of formula I as described in Example 911 with an equivalent amount of methyl bromide, instead of ethyl bromide, in the procedure of Example 911 gives 1,9-dimethyl-1-[2-(dimethylamino)ethyl]1,3,4,9-tetrahydrothiopyrano[3,4-b]indole, nmr (CDCl₃) δ3.72 (s, 6H), 6.40 (s, 3H), identical to the product of Example 732. The corresponding hydrochloric acid addition salt of this latter compound, 1,9-dimethyl-1-[2-(dimethylamino)ethyl]-1,3,4,9-tetrahydrothiopyrano[3,4-b]indole hydrochloride has m.p. 244° - 246° C.

Likewise, the use of the same compound of formula I as described in Example 911 with an equivalent amount of propyl bromide, instead of ethyl bromide, gives 1-[2-(dimethylamino)ethyl]-1-methyl-9-propyl-1,3,4,9-tetrahydrothiopyrano[3,4-b]indole.

We claim:
1. A process for preparing a compound of formula

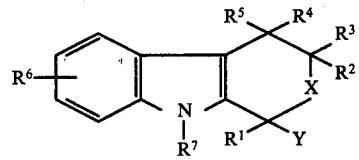

in which $R^1$ is lower alkyl or lower cycloalkyl; $R^2$, $R^3$, $R^4$ and $R^5$ are the same or different selected from the group consisting of hydrogen and lower alkyl; $R^6$ is hydrogen, lower alkyl, hydroxy, lower alkoxy, lower alkanoyloxy, nitro or halo; $R^7$ is lower alkyl, lower alkenyl, propargyl, phenyl(lower)alkyl or an amino(lower)alkyl radical of formula —Alk—NR⁸R⁹ wherein Alk is an alkylene selected from the group consisting of CR¹⁰R¹¹CR¹²R¹³, CR¹⁰R¹¹CR¹²R¹³CR¹⁴R¹⁵ and CR¹⁰R¹¹CR¹²R¹³CR¹⁴R¹⁵CR¹⁶R¹⁷ wherein R¹⁰, R¹¹, R¹², R¹³, R¹⁴, R¹⁵, R¹⁶ and R¹⁷ are hydrogen or lower alkyl and R⁸ and R⁹ are either the same or different selected from the group consisting of hydrogen and lower alkyl, or R⁸ and R⁹ together with the nitrogen atom to which they are joined form a heterocyclic amine radical selected from the group consisting of 1-pyrrolidinyl, piperidino, morpholino, piperazino, 4-(lower)alkyl)-1-piperazinyl and 4-[hydroxy(lower)alkyl]-1-piperazinyl; X is oxy or thio; and Y is an amino(lower)alkyl of formula Alk-NR⁸R⁸ in which Alk is an alkylene selected from the group consisting of CR¹⁰R¹¹, CR¹⁰R¹¹CR¹²R¹³, CR¹⁰R¹¹CR¹²R¹³CR¹⁴R¹⁵ and CR¹⁰R¹¹CR¹²R¹³CR¹⁴R¹⁵CR¹⁶R¹⁷ wherein R⁸, R⁹, R¹⁰, R¹¹, R¹², R¹³, R¹⁴, R¹⁵, R¹⁶ and R¹⁷ are as defined herein, and R⁸ is hydrogen or lower alkyl and R⁸ is lower alkyl, which comprises:
a. reacting in the presence of an inert organic solvent and an acid catalyst selected from the class consisting of p-toluenesulfonic acid, aluminum chloride, phosphorus pentoxide, boron trifluoride, zinc chloride, hydrochloric acid, perchloric acid, trifluoroacetic acid and sulfuric acid from 10 minutes to 60 hours at a temperature within the range from 20° C to the boiling point of the reaction mixture substantially equal molar equivalents of a compound of the formula:

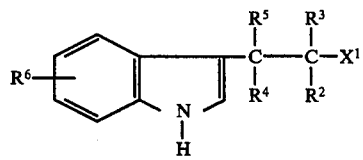

in which $R^2$, $R^3$, $R^4$, $R^5$ and $R^6$ are as defined herein and $X^1$ is hydroxy or mercapto, with the compound of formula

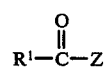

in which $R^1$ is lower alkyl or lower cycloalkyl and Z is Alk-NR⁸-COR²¹ in which Alk is an alkylene selected from the group consisting of CR¹⁰R¹¹, CR¹⁰R¹¹CR¹²R¹³, CR¹⁰R¹¹CR¹²R¹³CR¹⁴R¹⁵ and CR¹⁰R¹¹CR¹²R¹³CR¹⁴R¹⁵CR¹⁶R¹⁷ in which R¹⁰, R¹¹, R¹², R¹³, R¹⁴, R¹⁵, R¹⁶ and R¹⁷ are as defined herein, R⁸ is hydrogen or lower alkyl and R²¹ is hydrogen or lower alkyl containing one to five carbon atoms, to provide a tricyclic compound of the formula

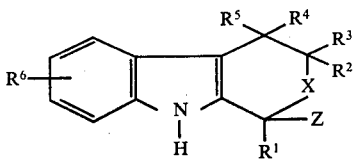

in which $R^1$, $R^2$, $R^3$, $R^4$, $R^5$, $R^6$, X and Z are as defined herein;

b. reducing the tricyclic compound with a suitable complex metal hydride to give the corresponding amine;

c. subjecting said amine to N-alkylation with an appropriate organic halide to introduce the $R^7$ substituent to give the corresponding compound of the formula

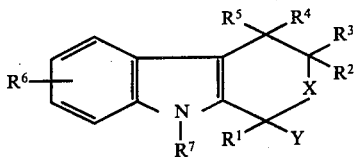

in which $R^1$, $R^2$, $R^3$, $R^4$, $R^5$, $R^6$, $R^7$ and X are as defined herein, Y is Alk $NR^8CH_2R^{21}$ wherein Alk, $R^8$ and $R^{21}$ are as defined herein; and, if desired, forming the acid addition salt thereof with a pharmaceutically acceptable acid.

2. The process of claim 1 in which $R^1$ is methyl; $R^2$ to $R^6$ inclusive are hydrogen; $R^7$ is ethyl; X is thio; Y is -Alk-$NR^8$-$R^9$ wherein Alk is $CH_2CH_2$ and $R^8$ and $R^9$ each is methyl; $X^1$ is mercapto; and Z is $CH_2CH_2N(CHO)CH_3$.

3. The process of claim 1 in which $R^1$ is methyl; $R^2$ to $R^6$ inclusive are hydrogen; $R^7$ is methyl; X is thio; Y is -Alk-$NR^8R^9$ wherein Alk is $CH_2CH_2$ and $R^8$ and $R^9$ each is methyl; $X^1$ is mercapto; and Z is $CH_2CH_2N(CHO)CH_3$.

4. The process of claim 1 in which $R^1$ is methyl; $R^2$ to $R^6$ inclusive are hydrogen; $R^7$ is methyl; X is oxy; Y is —Alk-$NR^8R^9$ wherein Alk is $CH_2CH_2$ and $R^8$ and $R^9$ each are methyl; $X^1$ is hydroxy; and Z is $CH_2CH_2N(CHO)CH_3$.

5. The process of claim 1 in which $R^7$ is lower alkyl.

6. The process of claim 1 in which $R^1$ is methyl; $R^2$ to $R^6$ inclusive are hydrogen; $R^7$ is ethyl; X is oxy; Y is —Alk—$NR^8R^9$ wherein Alk is $CH_2$, $R^8$ is hydrogen and $R^9$ is methyl; $X^1$ is hydroxy; and Z is $CH_2NH(CHO)$.

7. The process of claim 1 in which $R^1$ is methyl; $R^2$ to $R^6$ inclusive are hydrogen; $R^7$ is ethyl; X is thio; Y is —Alk—$NR^8R^9$ wherein Alk is $CH_2$, $R^8$ is hydrogen, and $R^9$ is methyl; $X^1$ is mercapto; and Z is $CH_2NH(CHO)$.

8. The process of claim 1 in which $R^1$ is methyl; $R^2$ to $R^6$ inclusive are hydrogen; $R^7$ is hydrogen; X is oxy; Y is —Alk—$NR^8R^9$ wherein Alk is $CH_2$, $R^8$ is hydrogen and $R^9$ is methyl; $X^1$ is hydroxy; and Z is $CH_2NH(CHO)$.

9. The process of claim 1 in which $R^1$ is methyl; $R^2$ to $R^6$ inclusive are hydrogen; $R^7$ is hydrogen; X is thio; Y is —Alk—$NR^8R^9$ wherein Alk is $CH_2$, $R^8$ is hydrogen and $R^9$ is methyl; $X^1$ is mercapto; and Z is $CH_2NH(CHO)$.

10. The process of claim 1 in which $R^1$ is methyl; $R^2$ to $R^6$ inclusive are hydrogen; $R^7$ is hydrogen; X is oxy; Y is —Alk$NR^8R^9$ in which Alk is $CH_2CH_2$, $R^8$ is hydrogen and $R^9$ is methyl; $X^1$ is hydroxy; and Z is $CH_2CH_2NH(CHO)$.

* * * * *

UNITED STATES PATENT AND TRADEMARK OFFICE
CERTIFICATE OF CORRECTION

PATENT NO. : 4,056,538

DATED : November 1, 1977

INVENTOR(S) : Christopher A. Demerson et al

It is certified that error appears in the above-identified patent and that said Letters Patent are hereby corrected as shown below:

In the Abstract, fifth line, "position" should read -- portion --.

In the Abstract, line four from the bottom, "pyranoand" should read -- pyrano- and --.

Column 2, line 10, "$NU^8R^9$" should read -- $NR^8R^3$ --.

Column 4, line 31, "thipyra" should read -- thiopyra --.

Column 4, line 56, the extraneous Roman numeral "III" appearing on the right side of column 4 under formula IV should be deleted.

Column 6, line 25, "loer" should read -- lower --.

Column 7, line 35, "Vi → VI" should read -- VI → VII --.

Column 17, line 39, "ethanediol" should read -- ethanethiol --.

Column 27, line 42, "pyrrolidone" should read -- pyrrolidine --.

Column 34, Table VI, Example 286, fourth column, second line, "carbonyl] piperzine" -- should read -- carbonyl] piperazine --.

Column 34, Table VI, Example 295, fourth column, first line, "benzyloxyl" should read -- benzyloxy --.

UNITED STATES PATENT AND TRADEMARK OFFICE
CERTIFICATE OF CORRECTION

PATENT NO. : 4,056,538

DATED : November 1, 1977

INVENTOR(S) : Christopher A. Demerson et al

It is certified that error appears in the above-identified patent and that said Letters Patent are hereby corrected as shown below:

Column 36, line 47, "192° - 192°" should read -- 192° - 193° --.

Column 36, line 53, "$d_5$" should read -- $d_6$ --.

Column 45, line 10, "The" should read -- In --.

Column 47, Table IX (continued), Example 525, third column, last line, "propyl)piperazine" should read -- propyl)piperidine --.

Column 51, Table XIII, Example 649, third column, "$(C_2H_5)_2$" should read -- $(C_2H_5)_2NH$ --.

Column 52, Table XII, heading of fourth column, second line, "TETREHYDROPYRANO[3,4-b] -" should read -- TETRAHYDROPYRANO[3,4-b] --.

Column 53, Table XIV, Example 671, third column, second line, "pyrazine" should read -- piperazine --.

Column 57, line 68, "trifluoride-ethanole" should read -- trifluoride-etherate --.

Column 58, line 67, "hexene" should read -- hexane --.

Column 59, line 29, "10NaOH" should read -- 10N NaOH --.

UNITED STATES PATENT AND TRADEMARK OFFICE
CERTIFICATE OF CORRECTION

Page 3 of 3

PATENT NO. : 4,056,538
DATED : November 1, 1977
INVENTOR(S) : Christopher A. Demerson et al It is certified that error appears in the above-identified patent and that said Letters Patent are hereby corrected as shown below:

Column 59, line 68, "(dimethylamino)]" should read -- (dimethylamino)methyl] --.

Column 59, line 67, "1-[2-" should read -- 1-[- --

Column 60, line 53, "1METHYL" should read -- 1-METHYL --.

Column 60, line 2, "309" should read -- 317 --.

Column 61, line 60, "$CH_2NHCH_3$" should read -- $CH_2NHC_2H_5$ --.

Column 62, line 51, after "tone," insert -- 1- --.

Column 71, line 41, "aluinum" should read -- aluminum --.

Column 71, line 47, "VIII $R^1$ M $CH_3$" should read -- VIII, $R^1 = CH_3$ --.

Column 72, line 47, "$CH_2NH_2$" should read -- $CH_2CH_2NH_2$ --.

Column 73, line 15, after "H," insert -- $R^7 = C_2H_5$, --.

Claim 1, column 74, line 29, "Alk-$NR^8R^8$" should read -- Alk-$NR^8R^9$ --.

Signed and Sealed this

Thirtieth Day of October 1979

[SEAL]

Attest:

RUTH C. MASON
Attesting Officer

LUTRELLE F. PARKER
Acting Commissioner of Patents and Trademarks